US006635429B1

(12) United States Patent
Leid et al.

(10) Patent No.: US 6,635,429 B1
(45) Date of Patent: Oct. 21, 2003

(54) HETERODIMERIC NUCLEAR RECEPTORS PROTEINS, GENES ENCODING SAME, AND USAGE THEREOF

(75) Inventors: Mark Leid, Strasbourg (FR); Philippe Kastner, Strasbourg (FR); Pierre Chambon, Blaesheim (FR)

(73) Assignees: Institut National de la Sante et de la Recherche Medicale, Paris (FR); Centre National de la Recherche Scientifique, Paris (FR); Universite Louis Pasteur, Strasbourg (FR); Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 08/216,592

(22) Filed: Mar. 23, 1994

Related U.S. Application Data

(63) Continuation-in-part of application No. 08/119,186, filed as application No. PCT/US93/00639 on Jan. 25, 1993, now abandoned, which is a continuation-in-part of application No. 07/825,667, filed on Jan. 24, 1992, now abandoned.

(51) Int. Cl.$^7$ .......................... G01N 33/53; C12P 21/06; C07H 17/00; C07K 14/00
(52) U.S. Cl. ...................... 435/7.1; 435/69.1; 435/69.4; 435/320.1; 536/23.1; 536/23.51; 530/350
(58) Field of Search ................................ 435/7.1, 69.4, 435/69.1, 320.1, 240.1; 536/23.1, 23.51; 530/350

(56) References Cited

U.S. PATENT DOCUMENTS

| | | | | |
|---|---|---|---|---|
| 5,403,925 A | * | 4/1995 | Ozato | 536/23.5 |
| 5,466,861 A | | 11/1995 | Dawson et al. | 560/100 |
| 5,552,271 A | * | 9/1996 | Pfahl et al. | 435/6 |
| 5,712,093 A | | 1/1998 | Pfahl et al. | 435/6 |
| 5,824,484 A | | 10/1998 | Pfahl et al. | 435/7.1 |
| 5,837,725 A | | 11/1998 | Dawson et al. | 514/467 |

FOREIGN PATENT DOCUMENTS

| | | |
|---|---|---|
| WO | WO 93/13129 | 7/1993 |

OTHER PUBLICATIONS

Hallenbeck et al. 1992 PNAS 89:5572–5576.*
Leid et al 1992 Cell 68:377–395.*
Kliewer et al 1992 Nature 355:446–449.*
Kliewer et al 1992 PNAS 89:1448–1452.*
Glass et al 1989 Cell 59:697–708.*
Mangelsdorf et al 1990 Nature 345:224–229.*
Kumar, V. and P. Chambon, "The Estrogen Receptor Binds Tightly to Its Responsive Element as a Ligand–Induced Homodimer," *Cell* 55:145–156 (1988).
Allegretto, et al., "Transactivation properties of retinoic acid and retinoid X receptors in mammalian cells and yeast," *J. Biol. Chem.* 268(35):26625–26633 (Dec. 1993).
Allenby, et al., "Retinoic acid receptors and retinoid X receptors: Interactions with endogenous retinoic acids," *Proc. Natl. Acad. Sci. USA* 89:30–34 (Jan. 1993).
Au–Fliegner, et al., "The Conserved Ninth C–Terminal Heptad in Thyroid Hormone and Retinoic Acid Receptors Mediates Diverse Responses by Affecting Heterodimer but Not Homodimer Formation," *Molecular and Cellular Biology* 13(9):5725–5737 (Sep. 1993).
Barettino, et al., "Characterization of the ligand–dependent transactivation domain of thyroid hormone receptor," *EMBO J.* 13(13):3039–3049 (Jul. 1994).
Berrodin, et al., "Heterodimerization among thyroid hormone receptor, retinoic acid receptor, retinoid X receptor, chicken ovalbumin upstream promoter transcription factor, and an endogenous liver protein," *Molecular Endocrinology* 6(9):1468–1478 (1992).
Brockes, J. "Retinoids, Homeobox Genes, and Linb Morphogenesis," *Neuron* 2:1285–1294 (Apr. 1989).
Brockes, J. "Reading the retinoid signals," *Nature* 345:766–768 (Jun. 1990).
Bugge et al., "RXR–Alpha, a Promiscuous Partner of Retinoic Acid and Thyroid Hormone Receptors," *EMBO J.* 11(4):1409–1418 (Apr. 1992).
Burnside, et al., "A Nuclear Factor That Enhances Binding of Thyroid Hormone Receptors to Thyroid Hormone Response Elements," *The J. of Biological Chemistry* 265(5):2500–2504 (Feb. 1990).
Chambon, P., Retinoids: 10 Years On Basel, Karger, 1991, pp 10–27.
Chambon, P., et al., "The retinoic signaling pathway: molecular and genetic analysis," *Seminars in Cell Biology* 5:115–125 (May 1994).
Chen et al., "Pure and Functionally Homogeneous Recombinant Retinoid Receptor," *The Journal of Biological Chemistry* 269(41):25770–25776 (Oct. 1994).
Cosgrove, et al., "Mice Lacking Mhc Class II Molecules," *Cell* 66:1051–1066 (Sep. 1991).
Danielian, et al., "Identification of a conserved region required for hormone dependent trascriptional activation by steroid hormone receptors," *EMBO J.* 11(3):1025–1033 (1992).

(List continued on next page.)

*Primary Examiner*—Karen Cochrane Carlson
(74) *Attorney, Agent, or Firm*—Sterne, Kessler Goldstein & Fox PLLC

(57) ABSTRACT

The present invention is based in part on the novel observation that two different types of nuclear receptors, retinoic acid receptors (RAR) and thyroid receptors (TR) dimerize with a RX receptor (RXR) to form a heterodimer which is capable of binding to retinoic acid response elements (RARE) or thyroid receptor response elements (TRE) at physiological conditions. In addition, the present invention discloses that RXR homodimers are capable of binding to RARE's. Based on this observation, the present invention provides novel dimeric proteins, methods of identifying agents capable of binding the dimers of the present invention, methods of identifying DNA sequences capable of being bound by the dimers and methods to identify RA metabolic enzymes and proteins which are required for the activation function of nuclear receptors.

42 Claims, 26 Drawing Sheets

OTHER PUBLICATIONS

Darling, et al., "3,5,3'-Triiodothyronine (T₃) Receptor–Auxiliary Protein (TRAP) Binds DNA and Forms Heterodimers," *Molecular Endocrinology* 5(1):85–93 (Jan. 1991).

De Luca, et al., "Retinoids and their receptors in differentiation, embryogenesis, and neoplasia," *FASED J.* 5:2924–2933 (1991).

de Thé, et al., "Identification of a retinoic acid responsive element in the retinoic acid receptor β gene," *Nature* 343(11):177–179 (Jan. 1990).

Desbois, et al., "v–erbA oncogene abrogates growth inhibition of chicken embryo fibroblasts induced by Retinoic acid," *Oncogene* 6:2129–2135 (Jun. 1991).

Durand, et al., "Activation function 2 (AF–2) of Retinoic acid receptor and 9–cis Retinoic acid receptor: presence of a conserved autonomous constitutive activating domain and influence of the nature of the response element on AF–2 activity," *EMBO J.* 13(22):5370–5382 (Nov. 1994).

Durand, et al., "All–Trans and 9–Cis retinoic acid induction of CRABPII transcription is mediated by RAR–RXR heterodimers bound to DR1 and DR2 repeated motifs," *Cell* 71:73–85 (1992).

Evans, et al., "The steroid and thyroid hormone receptor superfamily," *Science* 240:889–895 (1988).

Fawell, et al., "Characterization and colocalization of steroid binding and dimerization activities in the mouse estrogen receptor," *Cell* 60:953–962 (1990).

Forman, Barry and Samuels, Herbert, "Interactions Among a Subfamily of Nuclear Hormone Receptors: The Regulatory Zipper Model," *Molecular Endocrinology* 4(9):1293–1301 (Jun. 1990).

Forman, Barry and Samuels, Herbert H., "pEXPRESS: A family of expression vectors containing a single transcription unit active in prokaryote, eukaryote and in vitro," *Gene* 105:9–15 (Nov. 1991).

Giguere, et al., "Identification of a receptor for the morphogen retinoic acid," *Nature* 30:624–629 (1987).

Glass, et al., "Positive and Negative Regulation of Gene Transcription by a Retinoic Acid–Thyroid Hormone Receptor Heterodimer," *Cell* 59:697–708 (Nov. 1989).

Glass, et al., "A c–erb–A binding site in rat growth hormone gene mediates trans–activation by thyroid hormone," *Nature* 329 (Oct. 1987).

Glass, et al., "Multiple Cell Type–Specific Proteins Differentially Regulate Target Sequence Recognition by the α Retinoic Acid Receptor," *Cell* 63:729–738 (Nov. 1990).

Graupner, et al., "Dual regulatory role for thyroid–hormone receptors allows control of retinoic–acid receptor activity," *Nature* 340:653–656 (Aug. 1989).

Green, et al., "Nuclear receptors enhance our understanding of transcription regulation," *Trends. Genet.* 4(11):309–314 (1988).

Gronemeyer, H., "Transcription activation by estrogen and progestrone receptors," *Annu. Rev. Genet.* 25:89–123 (1991).

Grusby, et al., "Depletion of CD4⁺ T Cells in Major Histocompatibility Complex Class II–Deficient Mice," *Science* 253:1417–1420 (Sep. 1991).

Hallenbeck, et al., "Heterodimerization of thyroid hormone (TH) receptor with H–2RIIBP (RXRβ) enhances DNA binding and TH–dependent transcriptional activation," *Proc. Natl. Acad. Sci. USA* 89:5572–5576 (Jun. 1992).

Hamada, et al., "H–2RIIBP, a member of the nuclear hormone receptor superfamily that binds to both the regulatory element of major histocompatibility class I genes and the estrogen response element," *Proc. Natl. Acad. Sci. USA* 86:8289–8293 (Nov. 1989).

Heery, et al., "Efficient transactivation by retinoic acid receptors in yeast requires retinoid X receptor," *Proc. Natl. Acad. Sci. USA* 90:4281–4285 (May 1993).

Heyman, et al., "9–Cis retinoic acid is a high affinity ligand for the retinoid X receptor," *Cell* 68:397–406 (1992).

Hodgson, John, "Carbohydrate–Based Therapeutics," *Bio/Technology* 9:609–613 (Jul. 1991).

Hodgson, John, "Protein Design: Rules, Empiricism, & Nature," *Bio/Technology* 8:1245–1247 (Dec. 1990).

Hudson, et al., "Ligand–Activated Thyroid Hormone and Retinoic Acid Receptors Inhibit Growth Factor Receptor Promoter Expression," *Cell* 62:1165–1175 (Sep. 1990).

Kakizuka, et al., "Chromosomal translocation t(15;17) in human acute promyelocytic leukemia fuses RARα with a novel putative transcription factor, PML," *Cell* 68:663–674 (1991).

Kastner, et al., "Murine isoforms of retinoic acid receptor γ with specific patterns of expression," *Proc. Natl. Acad. Sci. USA* 87:2700–2704 (1990).

Kliewer, et al., "Retinoid X interacts with nuclear receptors in retinoic acid, thyroid hormone and vitamin D₃ signalling," *Nature* 355:446–449 (Jan. 1992).

Kliewer, et al., "Retinoid X Receptor–COUP–TF interactions modulate retinoic acid signaling," *Proc. Natl. Acad. Sci. USA* 89:1448–1452 (Feb. 1992).

Koelle, et al., "The Drosophila EcR Gene Encodes an Ecdysone Receptor, a New Member of the Steroid Receptor Superfamily," *Cell* 67:59–77 (Oct. 1991).

Laudet, et al., "Evolution of the nuclear receptor gene superfamily," *EMBO J.* 11(3):1003–1013 (1992).

Lazar, et al., "Differential DNA Binding by Monomeric, Homodimeric, and Potentially Heterodimeric Forms of the Thyroid Hormone Receptor," *Molecular and Cellular Biology* 11(10):5005–5015 (Oct. 1991).

Lee, et al., "Structure of the Retinoid X Receptor α DNA Binding Domain: A Helix Required for Homodimeric DNA Binding," *Science* 260:1117–1121 (May 1993).

Lehmann, et al., "RARγ2 expression is regulated through a retinoic acid response element embedded in Sp1 sites," *Mol. Cell. Biol.* 12:2976–2985 (Jul. 1992).

Leid, et al., "Multiplicity generates diversity in the retinoic acid signaling pathways," *TIBS* 17:427–433 (Oct. 1992).

Leid, et al., "Purification, Cloning, and RXR Identity of the HeLa Cell Factor With Which RAR or TR Heterodimerizes to Bind Target Sequences Efficiently," *Cell* 68:377–395 (Jan. 1992).

Leng, et al., "Mouse Retinoid X Receptor Contains a Separable Ligand–Binding and Transactivation Domain in Its E Region," *Molecular and Cellular Biology* 15(1):255–263 (Jan. 1995).

Leroy, et al., "Multiple isoforms of the mouse retinoic acid receptor α are generated by alternative splicing and differential induction by retinoic acid," *EMBO J.* 10(1):59–69 (1991).

Leroy, et al., "Mouse retinoic acid receptor α 2 isoform is transcribed from a promoter that contains a retinoic acid response element," *Proc. Natl., Acad. Sci. USA* 88:10138–10142 (Nov. 1991).

Levine, et al., "9–Cis retinoic acid stereoisomer binds and activates the nuclear receptor RXRα," *Nature* 355:359–361 (Jan. 1992).

Liao, et al., "Vitamin D receptor interaction with specific DNA requires a nuclear protein and 1,25–dihyroxyvitamin $D_3$," *Proc. Natl. Acad. Sci. USA* 88:9751–9755 (1990).

Linney, et al., "Retinoic acid receptors: Transcription factors modulating gene regulation, development, and differentiation," *Curr. Topics in Develop. Biolo.* 27:309–350 (1992).

Luisi, et al., "Crystallographic analysis of the interaction of the glucocorticoid receptor with DNA," *Nature* 352:497–505 (1991).

Mader, et al., "Multiple parameters control the selectivity of nuclear receptors for their response elements," *J. Biol. Chem.* 268:591–600 (Jan. 1993).

Mangelsdorf, et al., "Nuclear receptor that identifies a novel retinoic acid response pathway," *Nature* 345:224–229 (May 1990).

Mangelsdorf, et al., "A Direct Repeat in the Cellular Retinol–Binding Protein Type II Gene Confers Differential Regulation by RXR and RAR," *Cell* 66:555–561 (Aug. 1991).

Mangelsdorf et al., "Characterization of Three RXR Genes that Mediate the Action 9–Cis Retinoic Acid," *Gene and Develop.* 6:329–344 (1992).

Marks, et al., "H–2RIIBP (RXRβ) heterodimerization provides a mechanism for combinatoral diversity in regulation mechanism for conbinatoral diversity in the regulation of retinoic acid and thyroid hormone responsive genes," *EMBO J.* 11(4):1419–1435 (1992).

Mendelsohn, et al., "Developmental analysis of the retinoic acid–inducible RAR–beta2 promoter in transgenic animals," *Development* 113:723–734 (1991).

Murray, Mary B. and Towle, Howard C., "Identification of Nuclear Factors that Enhance Binding of the Thyroid Hormone Receptor to a Thyroid Hormone Response Element," *Molecular Endocrinology* 3(9):1434–1442 (Jun. 1989).

Näär, et al., "The Orientation and Spacing of Core DNA–Binding Motifs Dictate Selective Transcriptional Response to Three Nuclear Receptors," *Cell* 65:1267–1279 (Jun. 1991).

Nagpal, et al., "RARs and RXRs: evidence for two autonomous transactivation functions (AF–1 and AF–2) and heterodimerization in vivo," *EMBO J.* 12(6):2349–2360 (Jun. 1993).

Nakshatri, et al., "The directly repeated RG(G/T)TCA motifs of the rat and mouse cellular retinol–binding protein II genes are promiscuous binding sites for RAR, RXR, HNF–4, and ARP–1 homo– and heterodimers," *J. Biol. Chem.* 269:890–902 (Jan. 1994).

Nicholson, et al., "Negative regulation of the rat stromelysin gene promoter to retinoic acid is mediated by an AP1 binding site," *EMBO J.* 9(13): 4443–4454 (1990).

Oro, et al., "Relationship between the product of the *Drosophila ultraspiracle* locus and the vertebrate retinoid X receptor," *Nature* 347:298–301 (1990).

Pandolfi, et al., "Structure and origin of the acute promyelocytic leukemia myl/RARα cDNA and characterization of its retinoid–binding and transactivation properties," *Oncogene* 6:1285–1292 (1991).

Rowe, et al., "A member of the RXR nuclear receptor family is expressed in neural–crest–derived cells of the developing chick peripheral nervous system," *Development* 111:771–778 (1991).

Ruberte, et al., "Retinoic acid receptors in the embryo," *Seminar in Developmental Biology* 2:153–159 (1991).

Ruberte, et al., "Retinoic acid receptors and cellular retinoid binding proteins," *Development* 111:45–60 (1991).

Schwabe, et al., "Beyond zinc fingers: steroid hormone receptors have a novel structural motif for DNA recognition," *Trends in Biochem. Sci.* 116:291–296 (Aug. 1991).

Sharif, et al., "v–erbA Oncogene Function in Neoplasia Correlates with Its Ability to Repress Retinoic Acid Receptor Action," *Cell* 66:885–893 (Sep. 1991).

Sherman, Michael I., "Retinoids and Cell Differentiation," CRC Press (1986), pp. 61–186.

Smith, et al., "A retinoic acid response element is present in the mouse cellular retinol binding protein I (mCRBPI) promoter," *EMBO J.* 10(8):2223–2230 (1991).

Spanjaard, et al., "Ligand–binding and heterodimerization activities of a conserved region in the ligand–binding domain of the thyroid hormone receptor," *Proc. Natl. Acad. Sci. USA* 88:8587–8591 (1991).

Sucov, et al., "Characterization of an autoregulated response element in the mouse retinoic acid receptor type β gene," *Proc. Natl. Acad. Sci. USA* 87:5392–5396 (Jul. 1990).

Summerbell, D. and Maden, M., "Retinoic acid, a developmental signaling molecule," *TINS* 13(4):142–146 (1990).

Tasset, et al., "Distinct Classes of Transcriptional Activating Domains Function by Different Mechanisms," *Cell* 62:1177–1187 (Sep. 1990).

Umesono, et al., "Direct Repeats as Selective Response Elements for the Thyroid Hormone, Retinoic Acid, and Vitamin $D_3$ Receptors," *Cell* 65:1255–1266 (Jun. 1991).

Vasios, et al., "A retinoic acid–responsive element is present in the 5' flanking region of the laminin B1 gene," *Proc. Natl. Acad. Sci. USA* 86:9099–9103 (Dec. 1989).

Vasios, et al., "The late retinoic acid induction of laminin B1 gene transcription involves RAR binding to the responsive element," *EMBO J.* 10(5):1149–1158 (1991).

Yang et al., "Characterization of DNA binding and retinoic acid binding properties of retinoic acid receptor," *Proc. Natl. Acad. Sci. USA* 88:3559–3563 (May 1991).

Yaoita, et al., "*Xenopus laevis* α and β thyroid hormone receptors," *Proc. Natl. Acad. Sci. USA* 87:7090–7094 (1990).

Yu, et al., "RXRβ: A coregulation that enhances binding of retinoic acid, thyroid hormone, and vitamin D receptors to their cognate response elements," *Cell* 67:1251–1266 (1991).

Zechel, et al., "The Dimerization interfaces formed between the DNA binding domains of RXR, RAR and TR determine the binding specificity and polarity of the full–length receptors to direct repeats," *EMBO J.* 13(6):1425–1433 (1994).

Zelent, et al., "Differentially expressed isoform of the mouse retinoic acid receptor β are generated by usage of two promoters and alternative splicing," *EMBO J.* 10(1):71–81 (1991).

Zhang, et al., "Mutations That Alter Ligand–Induced Switches and Dimerization Activities in the Retinoid X Receptor," *Molecular and Cellular Biology* 14(6):4311–4323 (Jun. 1994).

Zhang et al., "Retinoid X Receptor is an Auxillary Protein for Thyroid Hormone and Retinoic Acid Receptors," *Nature* 355:441–446 (1992).

Fleischhauer, K., et al., "Isolation of a full–length cDNA clone encoding a N–terminally variant form of the human retinoid X receptor β," *Nucleic Acids Research* 20(7):1801 (Apr. 1992).

Erratum to Leid, M., et al., "Purification, Cloning and RXR Identity of the HeLa Cell Factor with which RAR or TR Heterodimerizes to Bind Target Sequences Efficiently," *Cell* 71(5):886a (Nov. 1992).

* cited by examiner

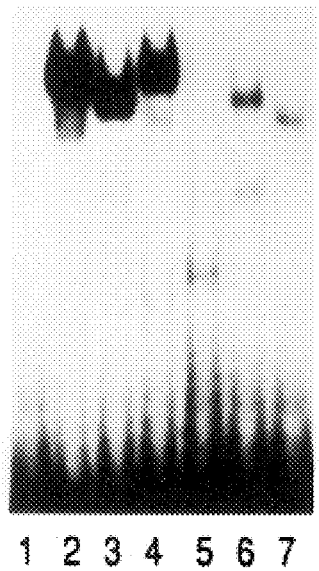
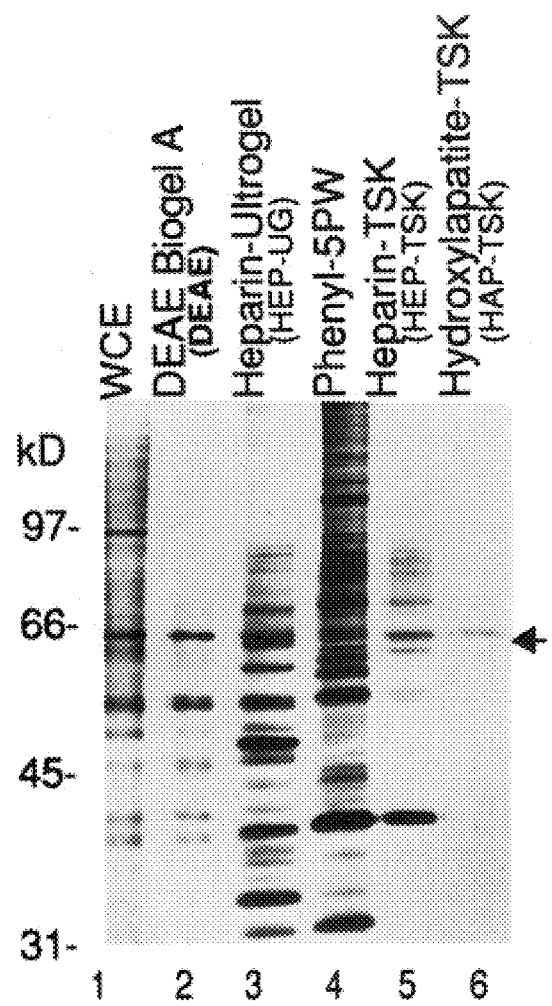
FIG. 1C
FIG. 1D

```
                              hRXR-β  1 MSWAARPPFLPQRHAEGSVGRWGAKECIVGSATALAGSRSGG
                                        ............................

hRXR-β 43 GGGGGRRRTTNPGAGARGWTGRDGRHGRDSRSPDSSSPNPLPQGVPPPSPPGPPLPPSTAPTLGGSGA
mRXR-β        1                             LGPDSRSPDSSSPNPLSQGIRPSSPPGPPLTPSA---------
mRXR-α  1 M--DTKHFLPLDFSTQVNSSSLNSPTGRGSMAVPSLHPS-LGPGIGSP--LGSPGQLHSPI-------
mRXR-γ  1 MYGNYSHFM--KFPTGFGGSP--GHTGSTSMSPSVALPT-GKPMDSHPSYTDTPVSAPRTL-------
              *  *        *              *
```

```
                                                                              A/B
          ..................................................................
112  PPPPPMPPPPLGSPFPVISSSMGSPGLPPPAPPGFSGPVSSPQINSTVSLPGGGSGPPEDVKPPVLGV
 35  -PPPPMPPPPLGSPFPVISSSMGSPGLPPPAPPGFSGPVSSPQINSTVSLPGGGSGPPEDVKPPVLGV
 57  -STLSSPINGMGPPFSVISSPMGPHSMSVPTTPTLGFGTGSPQLNSPMN----PVSSTEDIKPP-LGL
 57  -SAVGTPLNALGSPYRVITSAMGPPSGALAAPPGINLVAPPSSQLNVVN----SVSSSEDIKPL-PGL
      *    * *  ** * **            *                      ** **    *
```

```
          ........       ..........    .................................
180  RGLHCPP---PPGGPGA-GKRL|CAICGDRSSGKHYGVYSCEGCKGFFKRTIRKDLTYSCRDNKDCTVDK
102  RGLHCPP---PPGGPGA-GKRL|CAICGDRSSGKHYGVYSCEGCKGFFKRTIRKDLTYSCRDNKDCTVDK   C
119  NGVLKVPAHPSGNMASFTKHI|CAICGDRSSGKHYGVYSCEGCKGFFKRTVRKDLTYTCRDNKDCLIDK
119  PGIGNM-NYPSTSPGSLVKHI|CAICGDRSSGKHYGVYSCEGCKGFFKRTIRKDLIYTCRDNKDCLIDK
      *     *       *     ***************************** **** * ******* **
                              p6                p24
          .............. .......  ..........    .....................
245  |RQRNRCQYCRYQKCLATGM|KR|EAVQ|EERQRGKDK-DGDGEGAGGAPEEMPVDR|ILEAELAV|EQKSDQG
167  |RQRNRCQYCRYQKCLATGM|KREAVQEERQRGKDK-DGDGDGAGGAPEEMPVDRILEAELAVEQKSDQG
187  |RQRNRCQYCRYQKCLAMGM|KREAVQEERQRGKDRNENEVESTSSANEDMPVEKILEAELAVEPKTETY   D
186  |RQRNRCQYCRYQKCLVMGM|KREAVQEERQRSRERAESEAECASSSHEDMPVERILEAELAVEPKTESY
      ****************** ************           *  ***  ********* *
```

FIG.2A

```
312  VEGPGGTGGGSGSSPNDPVTNICQAADKQLFTLVEWAKRIPHFSSLPLDDQVILLRAGWNELLIASFSH
234  VEGPGATGGGGSSPNDPVTNICQAADKQLFTLVEWAKRIPHFSSLPLDDQVILLRAGWNELLIASFSH
255  VEA--NMGLNPSSPNDPVTNICQAADKQLFTLVEWAKRIPHFSELPLDDQVILLRAGWNELLIASFSH
254  GDM--NVE---NSTNDPVTNICHAADKQLFTLVEWAKRIPHFSDLTLEDQVILLRAGWNELLIASFSH
     *  ******** ***************** * * ********************
```

```
              ←—p27—→
                    ←p25→      p21              p28
380  RSIDVRDGILLATGLHVHRNSAHSAGVGAIFDRVLTELVSKMRDMRMDKTELGCLRAIILFNPDAKGL
302  RSIDVRDGILLATGLHVHRNSAHSAGVGAIFDRVLTELVSKMRDMRMDKTELGCLRAIILFNPDAKGL     E
321  RSIAVKDGILLATGLHVHRNSAHSAGVGAIFDRVLTELVSKMRDMQMDKTELGCLRAIVLFNPDSKGL
317  RSVSVQDGILLATGLHVHRSSAHSAGVGSIFDRVLTELVSKMKDMQMDKSELGCLRAIVLFNPDAKGL
     **  * ************** ******* ************* ** *** ******** ***** ***
```

```
                                 p17
448  SNPSEVEVLREKVYASLETYCKQKYPEQQGRFAKLLLRLPALRSIGLKCLEHLFFFKLIGDTPIDTFL
370  SNPGEVEILREKVYASLETYCKQKYPEQQGRFAKLLLRLPALRSIGLKCLEHLFFFKLIGDTPIDTFL
389  SNPAEVEALREKVYASLEAYCKHKYPEQPGRFAKLLLRLPALRSIGLKCLEHLFFFKLIGDTPIDTFL
385  SNPSEVETLREKVYATLEAYTKQKYPEQPGRFAKLLLRLPALRSIGLKCLEHLFFFKLIGDTPIDSFL
     *** *** ****** ** * * ***** **************************************** **
```

```
516  MEMLEAPHQLA
438  MEMLEAPHQLA
457  MEMLEAPHQ-A
453  MEMLETPLQIT
     ***** * *
```

FIG.2B

|       |     |                          *              *                              |     |
|-------|-----|--------------------------------------------------------------------------|-----|
| mER   | 501 | LQQQHRRLAQ LLLILSHI RHMSNKGMEHLYNMCCKN                                   | 536 |
| hRAR-γ | 369 | RP SQ PYMFP RMLMKTTD RGISTKGAERAITLKMEI                                  | 404 |
| cTR-α1 | 355 | KHN IPH FWPK LLMKVTDL RMIGACHASRFLHMKVEC                                 | 390 |
| hVDR  | 373 | PPGSHLLYAK MIQKLAD LSILTEL RTLGNQNAEMCFSLKLKN (misaligned—see image)    | 408 |
| EcR   | 604 | DSMSLVFYAK LSILTEL RTLGNQNAEMCFSLKLKN                                    | 639 |
| mRXR-α | 413 | YPEQ P GRF AKLLLRL PALRSIGLKCLEHLFFFKLIG                                 | 448 |
| usp   | 448 | HPGDD GRF AQLLIRL PALRSISLKCDDHLFLFRITS                                  | 483 |
| E75A  | 550 | RPDQ PEF LAKLIETMP DLRTLSTLHTEKLVVFRTEH                                  | 585 |
| svp   | 482 | YPNQ PTRF GKLLIRLP SLRTVSSQVIEQLFFVRLVG                                  | 517 |
| rNGFl-B | 507 | DPQ PASCL SRLLGKL PELRTLCTQGLQRIFCLKLED                                 | 542 |
| hear-1 | 579 | RPLETSRF TKLLIKL PDLRTTLNNMHSEKLLSFRVD                                   | 615 |

FIG. 9

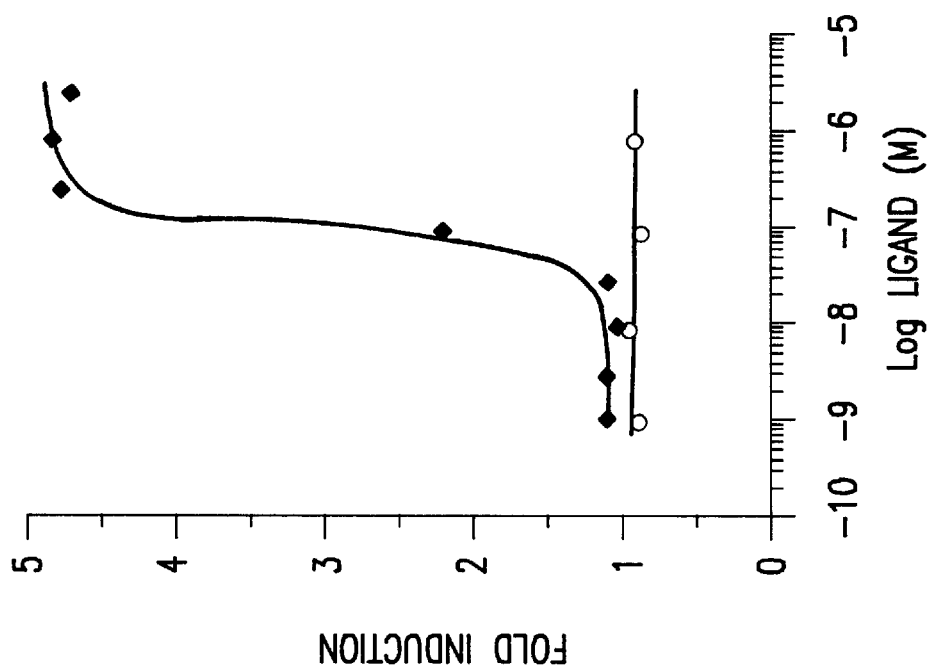
FIG.10B2
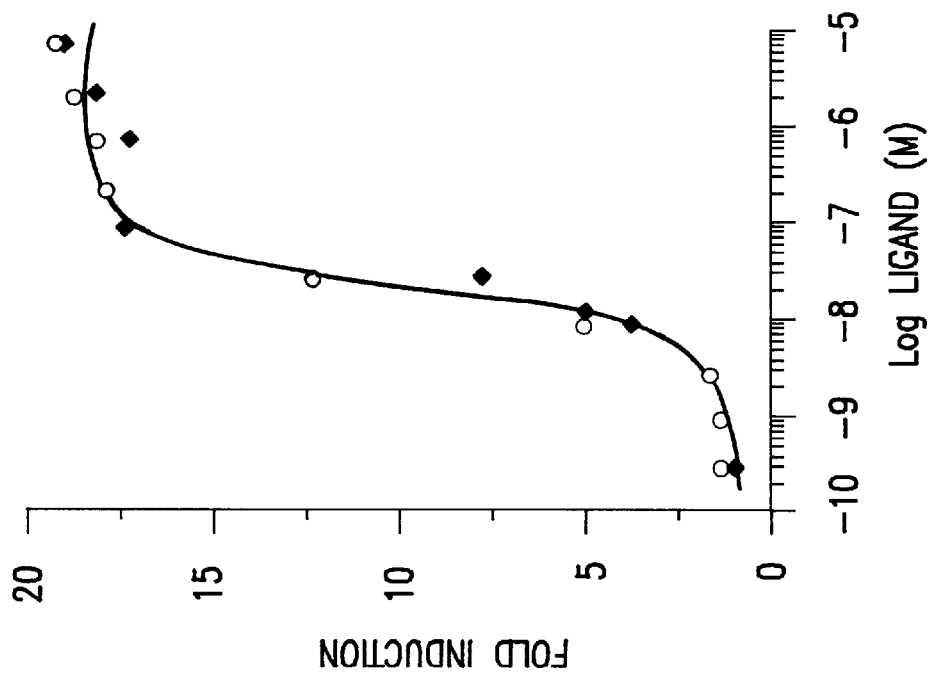
FIG.10B1

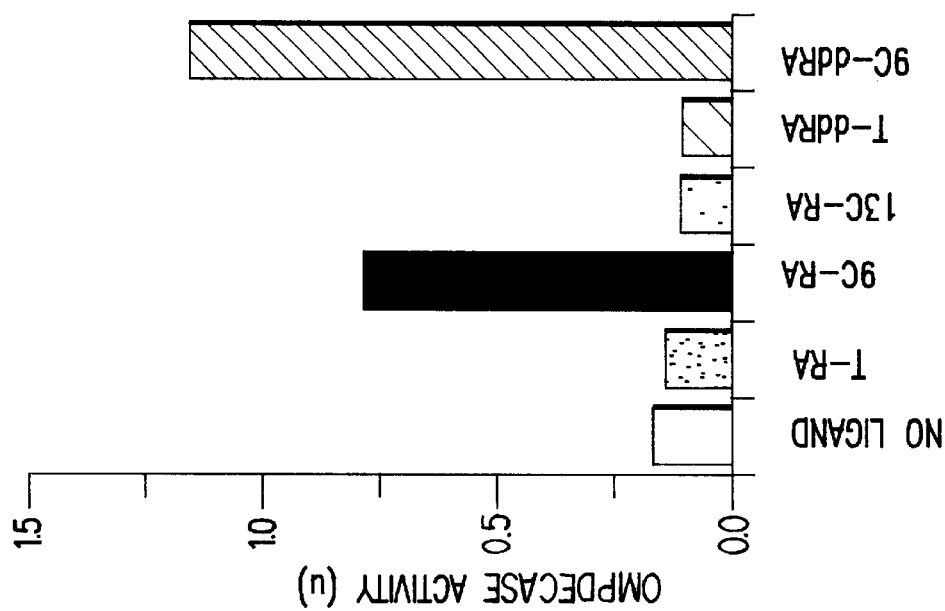
FIG.10C2
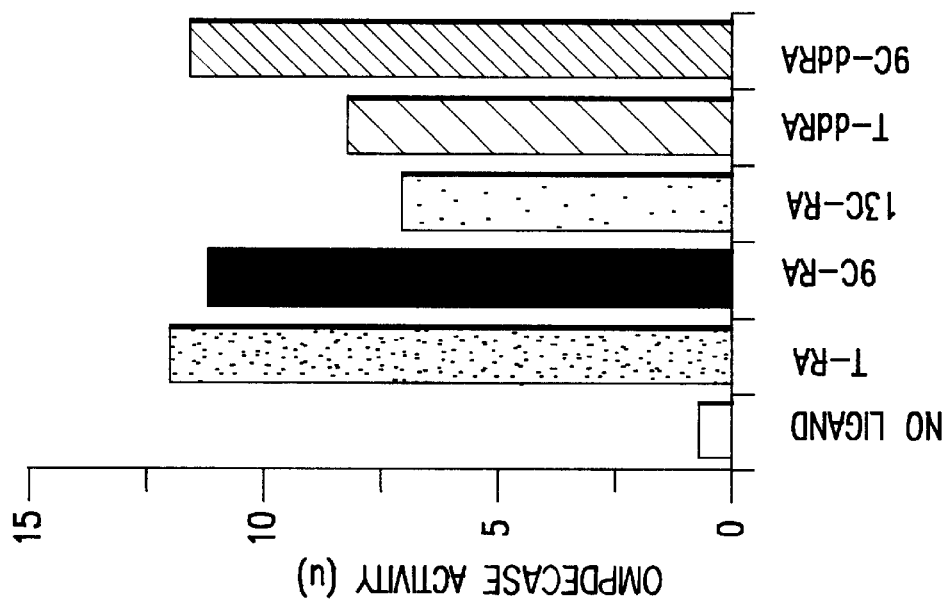
FIG.10C1

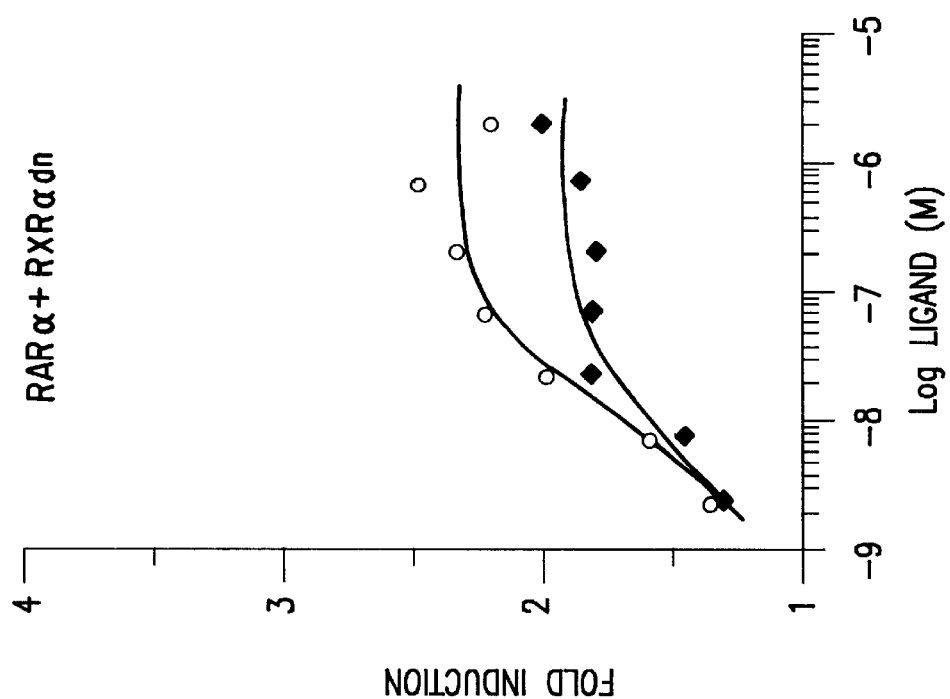
FIG.11C2
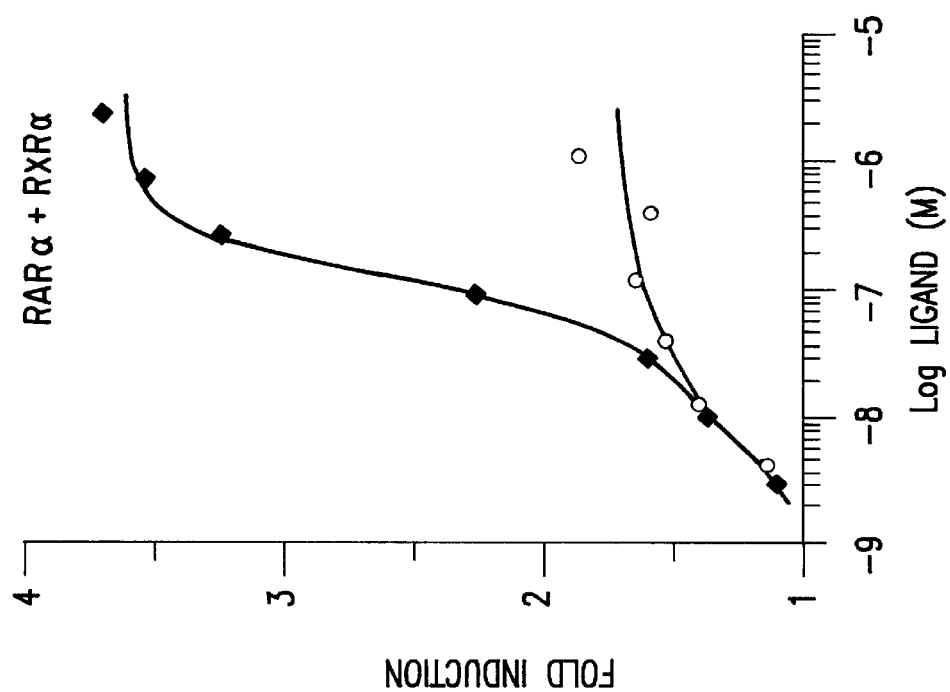
FIG.11C1

| | | |
|---|---|---|
| Seq ID No 25 | DR1 | AGGTCAgAGGTCA |
| Seq ID No 26 | DR2 | AGGTCAgcAGGTCA |
| Seq ID No 27 | DR3 | AGGTCAgcgAGGTCA |
| Seq ID No 28 | DR4 | AGGTCAgcgaAGGTCA |
| Seq ID No 24 | DR5 | AGGTCAgcgagAGGTCA |
| Seq ID No 29 | IR0 | AGGTCATGACCT |

SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
      (A) LENGTH: 2285 base pairs
      (B) TYPE: nucleic acid
      (C) STRANDEDNESS: both
      (D) TOPOLOGY: linear (ii) MOLECULE TYPE: DNA (ix) FEATURE:
      (A) NAME/KEY: CDS
      (B) LOCATION: 76..1420

(xi) SEQUENCE DESCRIPTION: SEQ ID NO:1:

```
GGGTCTCGGG CGTGGGAAGG ACACCGTTCC CCTTGGGCTG GAGGACTCTG GGCATTCGAA        60

GGCTGAGCTT ACGCT CTG GGA CCG GAT TCC CGA AGC CCA GAC AGC TCC TCC       111
              Leu Gly Pro Asp Ser Arg Ser Pro Asp Ser Ser Ser
                1               5                  10

CCA AAT CCC CTT TCT CAG GGG ATC CGT CCG TCT TCT CCT CCT GGC CCA        159
Pro Asn Pro Leu Ser Gln Gly Ile Arg Pro Ser Ser Pro Pro Gly Pro
            15                  20                  25

CCT CTT ACC CCT TCA GCA CCT CCA CCT CCA ATG CCA CCC CCG CCA CTG        207
Pro Leu Thr Pro Ser Ala Pro Pro Pro Pro Met Pro Pro Pro Pro Leu
 30                  35                  40

GGC TCC CCC TTC CCA GTC ATC AGT TCT TCC ATG GGG TCC CCT GGT CTG        255
Gly Ser Pro Phe Pro Val Ile Ser Ser Ser Met Gly Ser Pro Gly Leu
 45                  50                  55                  60

CCC CCT CCG GCT CCC CCA GGA TTC TCC GGG CCT GTC AGC AGC CCT CAG        303
Pro Pro Pro Ala Pro Pro Gly Phe Ser Gly Pro Val Ser Ser Pro Gln
                 65                  70                  75

ATC AAC TCC ACA GTG TCG CTC CCT GGG GGT GGG TCT GGC CCC CCT GAA        351
Ile Asn Ser Thr Val Ser Leu Pro Gly Gly Gly Ser Gly Pro Pro Glu
             80                  85                  90

GAT GTG AAG CCA CCG GTC TTA GGG GTC CGG GGC CTG CAC TGT CCA CCC        399
Asp Val Lys Pro Pro Val Leu Gly Val Arg Gly Leu His Cys Pro Pro
             95                 100                 105

CCT CCA GGT GGT CCT GGG GCT GGC AAA CGG CTC TGT GCA ATC TGC GGG        447
Pro Pro Gly Gly Pro Gly Ala Gly Lys Arg Leu Cys Ala Ile Cys Gly
        110                 115                 120

GAC CGA AGC TCA GGC AAG CAC TAT GGG GTT TAC AGC TGC GAG GGC TGC        495
Asp Arg Ser Ser Gly Lys His Tyr Gly Val Tyr Ser Cys Glu Gly Cys
125                 130                 135                 140

AAG GGT TTC TTC AAG CGC ACC ATT CGG AAG GAC CTG ACC TAC TCG TGT        543
Lys Gly Phe Phe Lys Arg Thr Ile Arg Lys Asp Leu Thr Tyr Ser Cys
                145                 150                 155

CGT GAT AAC AAA GAC TGT ACA GTG GAC AAG CGC CAG CGG AAT CGC TGT        591
Arg Asp Asn Lys Asp Cys Thr Val Asp Lys Arg Gln Arg Asn Arg Cys
                160                 165                 170

CAG TAC TGT CGC TAT CAG AAG TGC CTG GCC ACT GGC ATG AAA AGG GAG        639
Gln Tyr Cys Arg Tyr Gln Lys Cys Leu Ala Thr Gly Met Lys Arg Glu
            175                 180                 185

GCG GTT CAG GAG GAG CGT CAA CGG GGG AAG GAC AAA GAC GGG GAT GGA        687
Ala Val Gln Glu Glu Arg Gln Arg Gly Lys Asp Lys Asp Gly Asp Gly
        190                 195                 200

GAT GGG GCT GGG GGA GCC CCT GAG GAG ATG CCT GTG GAC AGG ATC CTG        735
```

```
Asp Gly Ala Gly Gly Ala Pro Glu Glu Met Pro Val Asp Arg Ile Leu
205                 210                 215                 220

GAG GCA GAG CTT GCT GTG GAG CAG AAG AGT GAC CAA GGC GTT GAG GGT      783
Glu Ala Glu Leu Ala Val Glu Gln Lys Ser Asp Gln Gly Val Glu Gly
                    225                 230                 235

CCT GGG GCC ACC GGG GGT GGT GGC AGC AGC CCA AAT GAC CCA GTG ACT      831
Pro Gly Ala Thr Gly Gly Gly Gly Ser Ser Pro Asn Asp Pro Val Thr
                240                 245                 250

AAC ATC TGC CAG GCA GCT GAC AAA CAG CTG TTC ACA CTC GTT GAG TGG      879
Asn Ile Cys Gln Ala Ala Asp Lys Gln Leu Phe Thr Leu Val Glu Trp
            255                 260                 265

GCA AAG AGG ATC CCG CAC TTC TCC TCC CTA CCT CTG GAC GAT CAG GTC      927
Ala Lys Arg Ile Pro His Phe Ser Ser Leu Pro Leu Asp Asp Gln Val
        270                 275                 280

ATA CTG CTG CGG GCA GGC TGG AAC GAG CTC CTC ATT GCG TCC TTC TCC      975
Ile Leu Leu Arg Ala Gly Trp Asn Glu Leu Leu Ile Ala Ser Phe Ser
285                 290                 295                 300

CAT CGG TCC ATT GAT GTC CGA GAT GGC ATC CTC CTG GCC ACG GGT CTT     1023
His Arg Ser Ile Asp Val Arg Asp Gly Ile Leu Leu Ala Thr Gly Leu
                305                 310                 315

CAT GTG CAC AGA AAC TCA GCC CAT TCC GCA GGC GTG GGA GCC ATC TTT     1071
His Val His Arg Asn Ser Ala His Ser Ala Gly Val Gly Ala Ile Phe
                320                 325                 330

GAT CGG GTG CTG ACA GAG CTA GTG TCC AAA ATG CGT GAC ATG AGG ATG     1119
Asp Arg Val Leu Thr Glu Leu Val Ser Lys Met Arg Asp Met Arg Met
            335                 340                 345

GAC AAG ACA GAG CTT GGC TGC CTG CGG GCA ATC ATC ATG TTT AAT CCA     1167
Asp Lys Thr Glu Leu Gly Cys Leu Arg Ala Ile Ile Met Phe Asn Pro
        350                 355                 360

GAC GCC AAG GGC CTC TCC AAC CCT GGA GAG GTG GAG ATC CTT CGG GAG     1215
Asp Ala Lys Gly Leu Ser Asn Pro Gly Glu Val Glu Ile Leu Arg Glu
365                 370                 375                 380

AAG GTG TAC GCC TCA CTG GAG ACC TAT TGC AAG CAG AAG TAC CCT GAG     1263
Lys Val Tyr Ala Ser Leu Glu Thr Tyr Cys Lys Gln Lys Tyr Pro Glu
                385                 390                 395

CAG CAG GGC CGG TTT GCC AAG CTG CTG TTA CGT CTT CCT GCC CTC CGC     1311
Gln Gln Gly Arg Phe Ala Lys Leu Leu Leu Arg Leu Pro Ala Leu Arg
                400                 405                 410

TCC ATC GGC CTC AAG TGT CTG GAG CAC CTG TTC TTC TTC AAG CTC ATT     1359
Ser Ile Gly Leu Lys Cys Leu Glu His Leu Phe Phe Phe Lys Leu Ile
            415                 420                 425

GGC GAC ACC CCC ATT GAC ACC TTC CTC ATG GAG ATG CTT GAG GCT CCC     1407
Gly Asp Thr Pro Ile Asp Thr Phe Leu Met Glu Met Leu Glu Ala Pro
        430                 435                 440

CAC CAG CTA GCC TGAGCCCAGA TGCACACCGA GTGTCACTGA GGAGGACTTG         1459
His Gln Leu Ala
445

AGCCTGGGCA GGGGGCAGAG CCATGGGACA GGTGCAGACG AGGAGGGGAC TTGCCCAGCC   1519

TGCCAGGGAT CTGGCAACAC TTAGCAGGGT TCGCTTGGTC TCCAAGTCGA AGGGGACCCC   1579

AGATCCCTGT GAGGACTTTA TGTCTACCTT CAGTGGCCTT GAGTCTCTGA ATTTGTCGGG   1639

GTCTCCCATG GTGCAGGTGA TTCTTCATCC TGGCTCCCCA GCACAAAGCA CTGCCCTGCT   1699

TCCTTCTCAT TTGGCCTCAC TCCCTTCTGA AGAGTGGAAC AGAGCTCCCC CAGAAAGGGG   1759

TGTTGTGGGG CAGGCCCCCC AAGCTGATGA TCATGGGAGC AGGGCTCTGA CAGCCTTTAT   1819

CCTCTCAGAC TTGACAGATG GGGGCAGAGG AGGGACCTGC CTCTGTCTCC TGTCAGCCCC   1879

ATTTCACAGT CCCTCCTGCA GTCAGACTGA AGAATAAAGG GGTAGTGAAG GGGCTGCTGG   1939
```

-continued

```
AGGTGGAGGA ACCCATTGCT CTTTTAATTT CCTGTGAGGA GAGACTGGGA GTTAGACTCA    1999

AAGAAGTACT GTACATCCCC AGGTTGACTT AAATGTCAGG GCTGGAGATG GCATGTGGGC    2059

AAGGAGGCCC CTCAGGTGGG CTGTCCCAAA GCTCCCTGGG CTCTGCCTCG GGTGGCCCTA    2119

CAGCTCTTCC CTAGTCTTAA GCACAGCTAG GCCTGGGAGC AAGTGGGGAC ATTGATGGGG    2179

GTGGCCAGCC TGCAGAGTTG GGTGCTGGGC TGCATGGTTT TTGCCCTGGA CCTCTTTTGG    2239

GGGTTCCCTC CCATCTTTCA CTTGCACATA AAGTTGCTTT CCAGTT                  2285
```

(2) INFORMATION FOR SEQ ID NO:2:

(i) SEQUENCE CHARACTERISTICS:
        (A) LENGTH: 448 amino acids
        (B) TYPE: amino acid
        (D) TOPOLOGY: linear (ii) MOLECULE TYPE: protein (xi) SEQUENCE DESCRIPTION: SEQ ID NO:2:

```
Leu Gly Pro Asp Ser Arg Ser Pro Asp Ser Ser Pro Asn Pro Leu
 1               5                  10                  15

Ser Gln Gly Ile Arg Pro Ser Pro Pro Gly Pro Pro Leu Thr Pro
                20                  25                  30

Ser Ala Pro Pro Pro Met Pro Pro Pro Leu Gly Ser Pro Phe
            35                  40                  45

Pro Val Ile Ser Ser Ser Met Gly Ser Pro Gly Leu Pro Pro Ala
        50                  55                  60

Pro Pro Gly Phe Ser Gly Pro Val Ser Ser Pro Gln Ile Asn Ser Thr
 65                  70                  75                  80

Val Ser Leu Pro Gly Gly Gly Ser Gly Pro Glu Asp Val Lys Pro
                85                  90                  95

Pro Val Leu Gly Val Arg Gly Leu His Cys Pro Pro Pro Gly Gly
                100                 105                 110

Pro Gly Ala Gly Lys Arg Leu Cys Ala Ile Cys Gly Asp Arg Ser Ser
            115                 120                 125

Gly Lys His Tyr Gly Val Tyr Ser Cys Glu Gly Cys Lys Gly Phe Phe
    130                 135                 140

Lys Arg Thr Ile Arg Lys Asp Leu Thr Tyr Ser Cys Arg Asp Asn Lys
145                 150                 155                 160

Asp Cys Thr Val Asp Lys Arg Gln Arg Asn Arg Cys Gln Tyr Cys Arg
                165                 170                 175

Tyr Gln Lys Cys Leu Ala Thr Gly Met Lys Arg Glu Ala Val Gln Glu
            180                 185                 190

Glu Arg Gln Arg Gly Lys Asp Lys Asp Gly Asp Gly Asp Gly Ala Gly
        195                 200                 205

Gly Ala Pro Glu Glu Met Pro Val Asp Arg Ile Leu Glu Ala Glu Leu
    210                 215                 220

Ala Val Glu Gln Lys Ser Asp Gln Gly Val Glu Gly Pro Gly Ala Thr
225                 230                 235                 240

Gly Gly Gly Gly Ser Ser Pro Asn Asp Pro Val Thr Asn Ile Cys Gln
                245                 250                 255

Ala Ala Asp Lys Gln Leu Phe Thr Leu Val Glu Trp Ala Lys Arg Ile
            260                 265                 270

Pro His Phe Ser Ser Leu Pro Leu Asp Asp Gln Val Ile Leu Leu Arg
        275                 280                 285

Ala Gly Trp Asn Glu Leu Leu Ile Ala Ser Phe Ser His Arg Ser Ile
```

```
        290              295              300
Asp Val Arg Asp Gly Ile Leu Leu Ala Thr Gly Leu His Val His Arg
305              310              315              320

Asn Ser Ala His Ser Ala Gly Val Gly Ala Ile Phe Asp Arg Val Leu
                325              330              335

Thr Glu Leu Val Ser Lys Met Arg Asp Met Arg Met Asp Lys Thr Glu
                340              345              350

Leu Gly Cys Leu Arg Ala Ile Ile Met Phe Asn Pro Asp Ala Lys Gly
                355              360              365

Leu Ser Asn Pro Gly Glu Val Glu Ile Leu Arg Glu Lys Val Tyr Ala
    370              375              380

Ser Leu Glu Thr Tyr Cys Lys Gln Lys Tyr Pro Glu Gln Gln Gly Arg
385              390              395              400

Phe Ala Lys Leu Leu Leu Arg Leu Pro Ala Leu Arg Ser Ile Gly Leu
                405              410              415

Lys Cys Leu Glu His Leu Phe Phe Lys Leu Ile Gly Asp Thr Pro
                420              425              430

Ile Asp Thr Phe Leu Met Glu Met Leu Glu Ala Pro His Gln Leu Ala
                435              440              445
```

(2) INFORMATION FOR SEQ ID NO:3:

(i) SEQUENCE CHARACTERISTICS:
        (A) LENGTH: 1757 base pairs
        (B) TYPE: nucleic acid
        (C) STRANDEDNESS: both
        (D) TOPOLOGY: linear (ii) MOLECULE TYPE: DNA (ix) FEATURE:
        (A) NAME/KEY: CDS
        (B) LOCATION: 117..1718

(xi) SEQUENCE DESCRIPTION: SEQ ID NO:3:

```
GACCCAATCC AGGCCAGAGT CTTTCTCTCA GGGGCTTCCT CGTGCTCAGC TAATCCTCCG      60

ATCATCCTTG GGAATCCCTG GGACCTCTTC GGTATCCCTA CTCTCAGCCA GGGATC         116

ATG TCT TGG GCC GCT CGC CCG CCC TTC CTC CCT CAG CGG CAT GCC GCA       164
Met Ser Trp Ala Ala Arg Pro Pro Phe Leu Pro Gln Arg His Ala Ala
 1               5                  10                  15

GGG CAG TGT GGG CCG GTG GGG GTG CGA AAA GAA ATG CAT TGT GGG GTC       212
Gly Gln Cys Gly Pro Val Gly Val Arg Lys Glu Met His Cys Gly Val
                20                  25                  30

GCG TCC CGG TGG CGG CGG CGA CGG CCC TGG CTG GAT CCC GCA GCG GCG       260
Ala Ser Arg Trp Arg Arg Arg Arg Pro Trp Leu Asp Pro Ala Ala Ala
            35                  40                  45

GCG GCG GCG GCG GTG GCA GGC GGA GAA CAA CAA ACC CCG GAG CCG GAG       308
Ala Ala Ala Ala Val Ala Gly Gly Glu Gln Gln Thr Pro Glu Pro Glu
    50                  55                  60

CCA GGG GAG GCT GGA CGG GAC GGG ATG GGC GAC AGC GGG CGG GAC TCC       356
Pro Gly Glu Ala Gly Arg Asp Gly Met Gly Asp Ser Gly Arg Asp Ser
65                  70                  75                  80

CGA AGC CCA GAC AGC TCC TCC CCA AAT CCC CTT CCC CAG GGA GTC CCT       404
Arg Ser Pro Asp Ser Ser Ser Pro Asn Pro Leu Pro Gln Gly Val Pro
                85                  90                  95

CCC CCT TCT CCT CCT GGG CCA CCC CTA CCC CCT TCA ACA GCT CCT ACC       452
Pro Pro Ser Pro Pro Gly Pro Pro Leu Pro Pro Ser Thr Ala Pro Thr
                100                 105                 110

CTT GGA GGC TCT GGG GCC CCA CCC CCA CCC CCG ATG CCA CCA CCC CCA       500
```

-continued

| | | | | | | | | | | | | | |
|---|---|---|---|---|---|---|---|---|---|---|---|---|---|
|Leu|Gly|Gly|Ser|Gly|Ala|Pro|Pro|Pro|Pro|Met|Pro|Pro|Pro|
| |   |115|   |   |   |120|   |   |   |125|   |   |   |

```
CTG GGC TCT CCC TTT CCA GTC ATC AGT TCT TCC ATG GGG TCC CCT GGT       548
Leu Gly Ser Pro Phe Pro Val Ile Ser Ser Ser Met Gly Ser Pro Gly
    130             135             140

CTG CCC CCT CCA GCT CCC CCA GGA TTC TCC GGG CCT GTC AGC AGC CCC       596
Leu Pro Pro Pro Ala Pro Pro Gly Phe Ser Gly Pro Val Ser Ser Pro
145             150             155             160

CAG ATT AAC TCA ACA GTG TCA CTC CCT GGG GGT GGG TCT GGC CCC CCT       644
Gln Ile Asn Ser Thr Val Ser Leu Pro Gly Gly Gly Ser Gly Pro Pro
            165             170             175

GAA GAT GTG AAG CCA CCA GTC TTA GGG GTC CGG GGC CTG CAC TGT CCA       692
Glu Asp Val Lys Pro Pro Val Leu Gly Val Arg Gly Leu His Cys Pro
        180             185             190

CCC CCT CCA GGT GGC CCT GGG GCT GGC AAA CGG CTA TGT GCA ATC TGC       740
Pro Pro Pro Gly Gly Pro Gly Ala Gly Lys Arg Leu Cys Ala Ile Cys
            195             200             205

GGG GAC AGA AGC TCA GGC AAA CAC TAC GGG GTT TAC AGC TGT GAG GGT       788
Gly Asp Arg Ser Ser Gly Lys His Tyr Gly Val Tyr Ser Cys Glu Gly
210             215             220

TGC AAG GGC TTC TTC AAA CGC ACC ATC CGC AAA GAC CTT ACA TAC TCT       836
Cys Lys Gly Phe Phe Lys Arg Thr Ile Arg Lys Asp Leu Thr Tyr Ser
225             230             235             240

TGC CGG GAC AAC AAA GAC TGC ACA GTG GAC AAG CGC CAG CGG AAC CGC       884
Cys Arg Asp Asn Lys Asp Cys Thr Val Asp Lys Arg Gln Arg Asn Arg
            245             250             255

TGT CAG TAC TGC CGC TAT CAG AAG TGC CTG GCC ACT GGC ATG AAG AGG       932
Cys Gln Tyr Cys Arg Tyr Gln Lys Cys Leu Ala Thr Gly Met Lys Arg
            260             265             270

GAG GCG GTA CAG GAG GAG CGT CAG CGG GGA AAG GAC AAG GAT GGG GAT       980
Glu Ala Val Gln Glu Glu Arg Gln Arg Gly Lys Asp Lys Asp Gly Asp
        275             280             285

GGG GAG GGG GCT GGG GGA GCC CCC GAG GAG ATG CCT GTG GAC AGG ATC      1028
Gly Glu Gly Ala Gly Gly Ala Pro Glu Glu Met Pro Val Asp Arg Ile
290             295             300

CTG GAG GCA GAG CTT GCT GTG GAA CAG AAG AGT GAC CAG GGC GTT GAG      1076
Leu Glu Ala Glu Leu Ala Val Glu Gln Lys Ser Asp Gln Gly Val Glu
305             310             315             320

GGT CCT GGG GGA ACC GGG GGT AGC GGC AGC AGC CCA AAT GAC CCT GTG      1124
Gly Pro Gly Gly Thr Gly Gly Ser Gly Ser Ser Pro Asn Asp Pro Val
            325             330             335

ACT AAC ATC TGT CAG GCA GCT GAC AAA CAG CTA TTC ACG CTT GTT GAG      1172
Thr Asn Ile Cys Gln Ala Ala Asp Lys Gln Leu Phe Thr Leu Val Glu
            340             345             350

TGG GCG AAG AGG ATC CCA CAC TTT TCC TCC TTG CCT CTG GAT GAT CAG      1220
Trp Ala Lys Arg Ile Pro His Phe Ser Ser Leu Pro Leu Asp Asp Gln
            355             360             365

GTC ATA TTG CTG CGG GCA GGC TGG AAT GAA CTC CTC ATT GCC TCC TTT      1268
Val Ile Leu Leu Arg Ala Gly Trp Asn Glu Leu Leu Ile Ala Ser Phe
370             375             380

TCA CAC CGA TCC ATT GAT GTT CGA GAT GGC ATC CTC CTT GCC ACA GGT      1316
Ser His Arg Ser Ile Asp Val Arg Asp Gly Ile Leu Leu Ala Thr Gly
385             390             395             400

CTT CAC GTG CAC CGC AAC TCA GCC CAT TCA GCA GGA GTA GGA GCC ATC      1364
Leu His Val His Arg Asn Ser Ala His Ser Ala Gly Val Gly Ala Ile
                405             410             415

TTT GAT CGG GTG CTG ACA GAG CTA GTG TCC AAA ATG CGT GAC ATG AGG      1412
Phe Asp Arg Val Leu Thr Glu Leu Val Ser Lys Met Arg Asp Met Arg
            420             425             430
```

-continued

```
ATG GAC AAG ACA GAG CTT GGC TGC CTG AGG GCA ATC ATT CTG TTT AAT         1460
Met Asp Lys Thr Glu Leu Gly Cys Leu Arg Ala Ile Ile Leu Phe Asn
            435                 440                 445

CCA GAT GCC AAG GGC CTC TCC AAC CCT AGT GAG GTG GAG GTC CTG CGG         1508
Pro Asp Ala Lys Gly Leu Ser Asn Pro Ser Glu Val Glu Val Leu Arg
    450                 455                 460

GAG AAA GTG TAT GCA TCA CTG GAG ACC TAC TGC AAA CAG AAG TAC CCT         1556
Glu Lys Val Tyr Ala Ser Leu Glu Thr Tyr Cys Lys Gln Lys Tyr Pro
465                 470                 475                 480

GAG CAG CAG GGA CGG TTT GCC AAG CTG CTG CTA CGT CTT CCT GCC CTC         1604
Glu Gln Gln Gly Arg Phe Ala Lys Leu Leu Leu Arg Leu Pro Ala Leu
                485                 490                 495

CGG TCC ATT GGC CTT AAG TGT CTA GAG CAT CTG TTT TTC TTC AAG CTC         1652
Arg Ser Ile Gly Leu Lys Cys Leu Glu His Leu Phe Phe Phe Lys Leu
            500                 505                 510

ATT GGT GAC ACC CCC ATC GAC ACC TTC CTC ATG GAG ATG CTT GAG GCT         1700
Ile Gly Asp Thr Pro Ile Asp Thr Phe Leu Met Glu Met Leu Glu Ala
    515                 520                 525

CCC CAT CAA CTG GCC TGAGCTCAGA CCCAGACGTG GTGCTTCTCA CACTGGAGGA         1755
Pro His Gln Leu Ala
        530

GC                                                                      1757
```

(2) INFORMATION FOR SEQ ID NO:4:

(i) SEQUENCE CHARACTERISTICS:
        (A) LENGTH: 533 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ser Trp Ala Ala Arg Pro Pro Phe Leu Pro Gln Arg His Ala Ala
 1               5                  10                  15

Gly Gln Cys Gly Pro Val Gly Val Arg Lys Glu Met His Cys Gly Val
                20                  25                  30

Ala Ser Arg Trp Arg Arg Arg Pro Trp Leu Asp Pro Ala Ala Ala
            35                  40                  45

Ala Ala Ala Val Ala Gly Gly Glu Gln Gln Thr Pro Glu Pro Glu
    50                  55                  60

Pro Gly Glu Ala Gly Arg Asp Gly Met Gly Asp Ser Gly Arg Asp Ser
65                  70                  75                  80

Arg Ser Pro Asp Ser Ser Pro Asn Pro Leu Pro Gln Gly Val Pro
                85                  90                  95

Pro Pro Ser Pro Pro Gly Pro Pro Leu Pro Pro Ser Thr Ala Pro Thr
                100                 105                 110

Leu Gly Gly Ser Gly Ala Pro Pro Pro Pro Met Pro Pro Pro
            115                 120                 125

Leu Gly Ser Pro Phe Pro Val Ile Ser Ser Ser Met Gly Ser Pro Gly
    130                 135                 140

Leu Pro Pro Pro Ala Pro Pro Gly Phe Ser Gly Pro Val Ser Ser Pro
145                 150                 155                 160

Gln Ile Asn Ser Thr Val Ser Leu Pro Gly Gly Ser Gly Pro Pro
                165                 170                 175

Glu Asp Val Lys Pro Pro Val Leu Gly Val Arg Gly Leu His Cys Pro
                180                 185                 190

Pro Pro Pro Gly Gly Pro Gly Ala Gly Lys Arg Leu Cys Ala Ile Cys
```

```
                    195                 200                 205
Gly Asp Arg Ser Ser Gly Lys His Tyr Gly Val Tyr Ser Cys Glu Gly
    210                 215                 220
Cys Lys Gly Phe Phe Lys Arg Thr Ile Arg Lys Asp Leu Thr Tyr Ser
225                 230                 235                 240
Cys Arg Asp Asn Lys Asp Cys Thr Val Asp Lys Arg Gln Arg Asn Arg
                245                 250                 255
Cys Gln Tyr Cys Arg Tyr Gln Lys Cys Leu Ala Thr Gly Met Lys Arg
            260                 265                 270
Glu Ala Val Gln Glu Glu Arg Gln Arg Gly Lys Asp Lys Asp Gly Asp
        275                 280                 285
Gly Glu Gly Ala Gly Gly Ala Pro Glu Glu Met Pro Val Asp Arg Ile
    290                 295                 300
Leu Glu Ala Glu Leu Ala Val Glu Gln Lys Ser Asp Gln Gly Val Glu
305                 310                 315                 320
Gly Pro Gly Gly Thr Gly Gly Ser Gly Ser Ser Pro Asn Asp Pro Val
                325                 330                 335
Thr Asn Ile Cys Gln Ala Ala Asp Lys Gln Leu Phe Thr Leu Val Glu
            340                 345                 350
Trp Ala Lys Arg Ile Pro His Phe Ser Ser Leu Pro Leu Asp Asp Gln
        355                 360                 365
Val Ile Leu Leu Arg Ala Gly Trp Asn Glu Leu Leu Ile Ala Ser Phe
    370                 375                 380
Ser His Arg Ser Ile Asp Val Arg Asp Gly Ile Leu Leu Ala Thr Gly
385                 390                 395                 400
Leu His Val His Arg Asn Ser Ala His Ser Ala Gly Val Gly Ala Ile
                405                 410                 415
Phe Asp Arg Val Leu Thr Glu Leu Val Ser Lys Met Arg Asp Met Arg
            420                 425                 430
Met Asp Lys Thr Glu Leu Gly Cys Leu Arg Ala Ile Ile Leu Phe Asn
        435                 440                 445
Pro Asp Ala Lys Gly Leu Ser Asn Pro Ser Glu Val Glu Val Leu Arg
    450                 455                 460
Glu Lys Val Tyr Ala Ser Leu Glu Thr Tyr Cys Lys Gln Lys Tyr Pro
465                 470                 475                 480
Glu Gln Gln Gly Arg Phe Ala Lys Leu Leu Leu Arg Leu Pro Ala Leu
                485                 490                 495
Arg Ser Ile Gly Leu Lys Cys Leu Glu His Leu Phe Phe Phe Lys Leu
            500                 505                 510
Ile Gly Asp Thr Pro Ile Asp Thr Phe Leu Met Glu Met Leu Glu Ala
        515                 520                 525
Pro His Gln Leu Ala
    530

(2) INFORMATION FOR SEQ ID NO:5:

(i) SEQUENCE CHARACTERISTICS:
        (A) LENGTH: 1883 base pairs
        (B) TYPE: nucleic acid
        (C) STRANDEDNESS: both
        (D) TOPOLOGY: linear (ii) MOLECULE TYPE: DNA (ix) FEATURE:
        (A) NAME/KEY: CDS
        (B) LOCATION: 96..1497
```

(xi) SEQUENCE DESCRIPTION: SEQ ID NO:5:

```
ACAAGTAGTT TACATTGTTG GGCGACTTTT GCAACAACTC GCCGCGCTGC CGCCCTGCTG        60

CTCCGCCGCC GGCTGGGCAT GAGTTAGTCG CAGAC ATG GAC ACC AAA CAT TTC         113
                                        Met Asp Thr Lys His Phe
                                          1               5

CTG CCG CTC GAC TTC TCT ACC CAG GTG AAC TCT TCG TCC CTC AAC TCT        161
Leu Pro Leu Asp Phe Ser Thr Gln Val Asn Ser Ser Ser Leu Asn Ser
             10                  15                  20

CCA ACG GGT CGA GGC TCC ATG GCT GTC CCC TCG CTG CAC CCC TCC TTG        209
Pro Thr Gly Arg Gly Ser Met Ala Val Pro Ser Leu His Pro Ser Leu
         25                  30                  35

GGT CCG GGA ATC GGC TCT CCA CTG GGC TCG CCT GGG CAG CTG CAC TCT        257
Gly Pro Gly Ile Gly Ser Pro Leu Gly Ser Pro Gly Gln Leu His Ser
     40                  45                  50

CCT ATC AGC ACC CTG AGC TCC CCC ATC AAT GGC ATG GGT CCG CCC TTC        305
Pro Ile Ser Thr Leu Ser Ser Pro Ile Asn Gly Met Gly Pro Pro Phe
 55                  60                  65                  70

TCT GTC ATC AGC TCC CCC ATG GGC CCG CAC TCC ATG TCG GTA CCC ACC        353
Ser Val Ile Ser Ser Pro Met Gly Pro His Ser Met Ser Val Pro Thr
                 75                  80                  85

ACA CCC ACA TTG GGC TTC GGG ACT GGT AGC CCC CAG CTC AAT TCA CCC        401
Thr Pro Thr Leu Gly Phe Gly Thr Gly Ser Pro Gln Leu Asn Ser Pro
             90                  95                 100

ATG AAC CCT GTG AGC AGC ACT GAG GAT ATC AAG CCG CCA CTA GGC CTC        449
Met Asn Pro Val Ser Ser Thr Glu Asp Ile Lys Pro Pro Leu Gly Leu
        105                 110                 115

AAT GGC GTC CTC AAG GTT CCT GCC CAT CCC TCA GGA AAT ATG GCC TCC        497
Asn Gly Val Leu Lys Val Pro Ala His Pro Ser Gly Asn Met Ala Ser
120                 125                 130

TTC ACC AAG CAC ATC TGT GCT ATC TGT GGG GAC CGC TCC TCA GGC AAA        545
Phe Thr Lys His Ile Cys Ala Ile Cys Gly Asp Arg Ser Ser Gly Lys
    135                 140                 145                 150

CAC TAT GGG GTA TAC AGT TGT GAG GGC TGC AAG GGC TTC TTC AAG AGG        593
His Tyr Gly Val Tyr Ser Cys Glu Gly Cys Lys Gly Phe Phe Lys Arg
                155                 160                 165

ACA GTA CGC AAA GAC CTG ACC TAC ACC TGC CGA GAC AAC AAG GAC TGC        641
Thr Val Arg Lys Asp Leu Thr Tyr Thr Cys Arg Asp Asn Lys Asp Cys
            170                 175                 180

CTG ATC GAC AAG AGA CAG CGG AAC CGG TGT CAG TAC TGC CGC TAC CAG        689
Leu Ile Asp Lys Arg Gln Arg Asn Arg Cys Gln Tyr Cys Arg Tyr Gln
        185                 190                 195

AAG TGC CTG GCC ATG GGC ATG AAG CGG GAA GCT GTG CAG GAG GAG CGG        737
Lys Cys Leu Ala Met Gly Met Lys Arg Glu Ala Val Gln Glu Glu Arg
    200                 205                 210

CAG CGG GGC AAG GAC CGG AAT GAG AAC GAG GTG GAG TCC ACC AGC AGT        785
Gln Arg Gly Lys Asp Arg Asn Glu Asn Glu Val Glu Ser Thr Ser Ser
215                 220                 225                 230

GCC AAC GAG GAC ATG CCT GTA GAG AAG ATT CTG GAA GCC GAG CTT GCT        833
Ala Asn Glu Asp Met Pro Val Glu Lys Ile Leu Glu Ala Glu Leu Ala
                235                 240                 245

GTC GAG CCC AAG ACT GAG ACA TAC GTG GAG GCA AAC ATG GGG CTG AAC        881
Val Glu Pro Lys Thr Glu Thr Tyr Val Glu Ala Asn Met Gly Leu Asn
            250                 255                 260

CCC AGC TCA CCA AAT GAC CCT GTT ACC AAC ATC TGT CAA GCA GCA GAC        929
Pro Ser Ser Pro Asn Asp Pro Val Thr Asn Ile Cys Gln Ala Ala Asp
        265                 270                 275

AAG CAG CTC TTC ACT CTT GTG GAG TGG GCC AAG AGG ATC CCA CAC TTT        977
Lys Gln Leu Phe Thr Leu Val Glu Trp Ala Lys Arg Ile Pro His Phe
```

```
      280                 285                 290
TCT GAG CTG CCC CTA GAC GAC CAG GTC ATC CTG CTA CGG GCA GGC TGG    1025
Ser Glu Leu Pro Leu Asp Asp Gln Val Ile Leu Leu Arg Ala Gly Trp
295                 300                 305                 310

AAC GAG CTG CTG ATC GCC TCC TTC TCC CAC CGC TCC ATA GCT GTG AAA    1073
Asn Glu Leu Leu Ile Ala Ser Phe Ser His Arg Ser Ile Ala Val Lys
                315                 320                 325

GAT GGG ATT CTC CTG GCC ACC GGC CTG CAC GTA CAC CGG AAC AGC GCT    1121
Asp Gly Ile Leu Leu Ala Thr Gly Leu His Val His Arg Asn Ser Ala
            330                 335                 340

CAC AGT GCT GGG GTG GGC GCC ATC TTT GAC AGG GTG CTA ACA GAG CTG    1169
His Ser Ala Gly Val Gly Ala Ile Phe Asp Arg Val Leu Thr Glu Leu
        345                 350                 355

GTG TCT AAG ATG CGT GAC ATG CAG ATG GAC AAG ACG GAG CTG GGC TGC    1217
Val Ser Lys Met Arg Asp Met Gln Met Asp Lys Thr Glu Leu Gly Cys
    360                 365                 370

CTG CGA GCC ATT GTC CTG TTC AAC CCT GAC TCT AAG GGG CTC TCA AAC    1265
Leu Arg Ala Ile Val Leu Phe Asn Pro Asp Ser Lys Gly Leu Ser Asn
375                 380                 385                 390

CCT GCT GAG GTG GAG GCG TTG AGG GAG AAG GTG TAT GCG TCA CTA GAA    1313
Pro Ala Glu Val Glu Ala Leu Arg Glu Lys Val Tyr Ala Ser Leu Glu
                395                 400                 405

GCG TAC TGC AAA CAC AAG TAC CCT GAG CAG CCG GGC AGG TTT GCC AAG    1361
Ala Tyr Cys Lys His Lys Tyr Pro Glu Gln Pro Gly Arg Phe Ala Lys
            410                 415                 420

CTG CTG CTC CGC CTG CCT GCA CTG CGT TCC ATC GGG CTC AAG TGC CTG    1409
Leu Leu Leu Arg Leu Pro Ala Leu Arg Ser Ile Gly Leu Lys Cys Leu
        425                 430                 435

GAG CAC CTG TTC TTC TTC AAG CTC ATC GGG GAC ACG CCC ATC GAC ACC    1457
Glu His Leu Phe Phe Phe Lys Leu Ile Gly Asp Thr Pro Ile Asp Thr
    440                 445                 450

TTC CTC ATG GAG ATG CTG GAG GCA CCA CAT CAA GCC ACC TAG GCC CCC    1505
Phe Leu Met Glu Met Leu Glu Ala Pro His Gln Ala Thr  *
455                 460                 465

GCC GCC GTG TGC CGG TCC CGT GCC CTG CCT GGA CAC AGC TGC TCA GCT    1553

CCA GCC CTG CCC CTG CCC TTT CTG ATG GCC CGT GTG GAT CTT TGG GGT    1601

GCA GTG TCC TTA TGG GCC CAA AAG ATG CAT CAC CAC TCT CGC CAT CTT    1649

TAC TCA TGC TTG CCT TTG GCC CAG GGC ATA GCA GAG CTG GTG TGA CAC    1697

CTG GCC AGC TCC TGC CCT ACA TCA GGC TCT AAG GCT ATG CTG CTG TCA    1745

CCC CGA GGG TCG TGG GGT TCG TCA TGG GGC CTT CAG TAC CTG GAG CTG    1793

CAA GAG CTG GGA AAA GGG CTT GTT CTG GTT GCT GGT TGC TGT CGC TGG    1841

TTC TCG ACA TCC CAC ATG GCA CCT CTG TTT GGA GTG CCC ATC            1883
```

(2) INFORMATION FOR SEQ ID NO:6:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO:6:

```
Met Asp Thr Lys His Phe Leu Pro Leu Asp Phe Ser Thr Gln Val Asn
1               5                   10                  15

Ser Ser Ser Leu Asn Ser Pro Thr Gly Arg Gly Ser Met Ala Val Pro
            20                  25                  30
```

-continued

```
Ser Leu His Pro Ser Leu Gly Pro Gly Ile Ser Pro Leu Gly Ser
        35                  40                  45

Pro Gly Gln Leu His Ser Pro Ile Ser Thr Leu Ser Ser Pro Ile Asn
    50                  55                  60

Gly Met Gly Pro Pro Phe Ser Val Ile Ser Ser Pro Met Gly Pro His
65                  70                  75                  80

Ser Met Ser Val Pro Thr Thr Pro Thr Leu Gly Phe Gly Thr Gly Ser
                85                  90                  95

Pro Gln Leu Asn Ser Pro Met Asn Pro Val Ser Ser Thr Glu Asp Ile
                100                 105                 110

Lys Pro Pro Leu Gly Leu Asn Gly Val Leu Lys Val Pro Ala His Pro
            115                 120                 125

Ser Gly Asn Met Ala Ser Phe Thr Lys His Ile Cys Ala Ile Cys Gly
130                 135                 140

Asp Arg Ser Ser Gly Lys His Tyr Gly Val Tyr Ser Cys Glu Gly Cys
145                 150                 155                 160

Lys Gly Phe Phe Lys Arg Thr Val Arg Lys Asp Leu Thr Tyr Thr Cys
                165                 170                 175

Arg Asp Asn Lys Asp Cys Leu Ile Asp Lys Arg Gln Arg Asn Arg Cys
            180                 185                 190

Gln Tyr Cys Arg Tyr Gln Lys Cys Leu Ala Met Gly Met Lys Arg Glu
        195                 200                 205

Ala Val Gln Glu Glu Arg Gln Arg Gly Lys Asp Arg Asn Glu Asn Glu
    210                 215                 220

Val Glu Ser Thr Ser Ser Ala Asn Glu Asp Met Pro Val Glu Lys Ile
225                 230                 235                 240

Leu Glu Ala Glu Leu Ala Val Glu Pro Lys Thr Glu Thr Tyr Val Glu
                245                 250                 255

Ala Asn Met Gly Leu Asn Pro Ser Pro Asn Asp Pro Val Thr Asn
                260                 265                 270

Ile Cys Gln Ala Ala Asp Lys Gln Leu Phe Thr Leu Val Glu Trp Ala
            275                 280                 285

Lys Arg Ile Pro His Phe Ser Glu Leu Pro Leu Asp Asp Gln Val Ile
        290                 295                 300

Leu Leu Arg Ala Gly Trp Asn Glu Leu Leu Ile Ala Ser Phe Ser His
305                 310                 315                 320

Arg Ser Ile Ala Val Lys Asp Gly Ile Leu Leu Ala Thr Gly Leu His
                325                 330                 335

Val His Arg Asn Ser Ala His Ser Ala Gly Val Gly Ala Ile Phe Asp
            340                 345                 350

Arg Val Leu Thr Glu Leu Val Ser Lys Met Arg Asp Met Gln Met Asp
        355                 360                 365

Lys Thr Glu Leu Gly Cys Leu Arg Ala Ile Val Leu Phe Asn Pro Asp
    370                 375                 380

Ser Lys Gly Leu Ser Asn Pro Ala Glu Val Glu Ala Leu Arg Glu Lys
385                 390                 395                 400

Val Tyr Ala Ser Leu Glu Ala Tyr Cys Lys His Lys Tyr Pro Glu Gln
                405                 410                 415

Pro Gly Arg Phe Ala Lys Leu Leu Leu Arg Leu Pro Ala Leu Arg Ser
            420                 425                 430

Ile Gly Leu Lys Cys Leu Glu His Leu Phe Phe Lys Leu Ile Gly
        435                 440                 445
```

```
Asp Thr Pro Ile Asp Thr Phe Leu Met Glu Met Leu Glu Ala Pro His
    450                 455                 460
Gln Ala Thr
465

(2) INFORMATION FOR SEQ ID NO:7:

(i) SEQUENCE CHARACTERISTICS:
        (A) LENGTH: 1488 base pairs
        (B) TYPE: nucleic acid
        (C) STRANDEDNESS: both
        (D) TOPOLOGY: linear (ii) MOLECULE TYPE: DNA (ix) FEATURE:
        (A) NAME/KEY: CDS
        (B) LOCATION: 36..1427

(xi) SEQUENCE DESCRIPTION: SEQ ID NO:7:

GAAGCGCAGT AGAGGAATGA ACTGAGCAGC CCAAC ATG TAT GGA AAT TAT TCC                53
                                       Met Tyr Gly Asn Tyr Ser
                                         1               5

CAC TTC ATG AAG TTT CCC ACC GGC TTT GGT GGC TCC CCT GGT CAC ACT             101
His Phe Met Lys Phe Pro Thr Gly Phe Gly Gly Ser Pro Gly His Thr
             10                  15                  20

GGC TCG ACG TCC ATG AGC CCT TCA GTA GCC TTG CCC ACG GGG AAG CCA             149
Gly Ser Thr Ser Met Ser Pro Ser Val Ala Leu Pro Thr Gly Lys Pro
         25                  30                  35

ATG GAC AGC CAC CCC AGC TAC ACA GAC ACC CCA GTG AGT GCC CCT CGG             197
Met Asp Ser His Pro Ser Tyr Thr Asp Thr Pro Val Ser Ala Pro Arg
     40                  45                  50

ACG CTG AGT GCT GTG GGA ACC CCC CTC AAT GCT CTT GGC TCT CCG TAT             245
Thr Leu Ser Ala Val Gly Thr Pro Leu Asn Ala Leu Gly Ser Pro Tyr
 55                  60                  65                  70

AGA GTC ATC ACT TCT GCC ATG GGT CCA CCC TCA GGA GCA CTG GCA GCT             293
Arg Val Ile Thr Ser Ala Met Gly Pro Pro Ser Gly Ala Leu Ala Ala
                 75                  80                  85

CCT CCA GGA ATC AAC TTG GTG GCT CCA CCC AGC TCC CAG CTA AAT GTG             341
Pro Pro Gly Ile Asn Leu Val Ala Pro Pro Ser Ser Gln Leu Asn Val
             90                  95                 100

GTC AAC AGT GTC AGC AGC TCT GAG GAC ATC AAG CCC TTA CCA GGT CTG             389
Val Asn Ser Val Ser Ser Ser Glu Asp Ile Lys Pro Leu Pro Gly Leu
         105                 110                 115

CCT GGG ATT GGA AAT ATG AAC TAC CCA TCC ACC AGT CCT GGG TCT CTG             437
Pro Gly Ile Gly Asn Met Asn Tyr Pro Ser Thr Ser Pro Gly Ser Leu
     120                 125                 130

GTG AAA CAC ATC TGT GCC ATC TGT GGG GAC AGA TCC TCA GGG AAG CAC             485
Val Lys His Ile Cys Ala Ile Cys Gly Asp Arg Ser Ser Gly Lys His
135                 140                 145                 150

TAC GGT GTG TAC AGC TGT GAA GGT TGC AAA GGC TTC TTC AAA AGG ACC             533
Tyr Gly Val Tyr Ser Cys Glu Gly Cys Lys Gly Phe Phe Lys Arg Thr
                155                 160                 165

ATC AGG AAA GAT CTC ATC TAT ACC TGT CGG GAT AAC AAA GAT TGT CTC             581
Ile Arg Lys Asp Leu Ile Tyr Thr Cys Arg Asp Asn Lys Asp Cys Leu
            170                 175                 180

ATC GAC AAG CGC CAG CGC AAC CGC TGC CAG TAC TGT CGC TAC CAG AAG             629
Ile Asp Lys Arg Gln Arg Asn Arg Cys Gln Tyr Cys Arg Tyr Gln Lys
        185                 190                 195

TGC CTG GTC ATG GGC ATG AAG CGG GAA GCT GTG CAA GAA GAA AGG CAG             677
Cys Leu Val Met Gly Met Lys Arg Glu Ala Val Gln Glu Glu Arg Gln
    200                 205                 210
```

```
AGG AGC CGA GAG CGA GCA GAG AGT GAG GCA GAA TGT GCC AGT AGT AGC    725
Arg Ser Arg Glu Arg Ala Glu Ser Glu Ala Glu Cys Ala Ser Ser Ser
215             220                 225                 230

CAC GAA GAC ATG CCC GTG GAG AGG ATT CTA GAA GCC GAA CTT GCT GTG    773
His Glu Asp Met Pro Val Glu Arg Ile Leu Glu Ala Glu Leu Ala Val
                235                 240                 245

GAA CCA AAG ACA GAA TCC TAC GGT GAC ATG AAC GTG GAG AAC TCA ACA    821
Glu Pro Lys Thr Glu Ser Tyr Gly Asp Met Asn Val Glu Asn Ser Thr
            250                 255                 260

AAT GAC CCT GTT ACC AAC ATA TGT CAT GCT GCA GAT AAG CAA CTT TTC    869
Asn Asp Pro Val Thr Asn Ile Cys His Ala Ala Asp Lys Gln Leu Phe
        265                 270                 275

ACC CTC GTT GAG TGG GCC AAA CGC ATC CCC CAC TTC TCA GAT CTC ACC    917
Thr Leu Val Glu Trp Ala Lys Arg Ile Pro His Phe Ser Asp Leu Thr
280                 285                 290

CTG GAG GAC CAG GTC ATT CTA CTC CGG GCA GGG TGG AAT GAA CTG CTC    965
Leu Glu Asp Gln Val Ile Leu Leu Arg Ala Gly Trp Asn Glu Leu Leu
295                 300                 305                 310

ATT GCC TCC TTC TCC CAC CGC TCG GTT TCC GTC CAG GAT GGC ATC CTG   1013
Ile Ala Ser Phe Ser His Arg Ser Val Ser Val Gln Asp Gly Ile Leu
                315                 320                 325

CTG GCC ACG GGC CTC CAC GTG CAC AGG AGC AGC GCT CAC AGC GCG GGA   1061
Leu Ala Thr Gly Leu His Val His Arg Ser Ser Ala His Ser Ala Gly
            330                 335                 340

GTC GGC TCC ATC TTC GAC AGA GTC CTT ACA GAG TTG GTG TCC AAG ATG   1109
Val Gly Ser Ile Phe Asp Arg Val Leu Thr Glu Leu Val Ser Lys Met
        345                 350                 355

AAA GAC ATG CAG ATG GAT AAG TCA GAG CTG GGG TGC CTA CGG GCC ATC   1157
Lys Asp Met Gln Met Asp Lys Ser Glu Leu Gly Cys Leu Arg Ala Ile
360                 365                 370

GTG CTG TTT AAC CCA GAT GCC AAG GGT TTA TCC AAC CCC TCT GAG GTG   1205
Val Leu Phe Asn Pro Asp Ala Lys Gly Leu Ser Asn Pro Ser Glu Val
375                 380                 385                 390

GAG ACT CTT CGA GAG AAG GTT TAT GCC ACC CTG GAG GCC TAT ACC AAG   1253
Glu Thr Leu Arg Glu Lys Val Tyr Ala Thr Leu Glu Ala Tyr Thr Lys
                395                 400                 405

CAG AAG TAT CCG GAA CAG CCA GGC AGG TTT GCC AAG CTT CTG CTG CGT   1301
Gln Lys Tyr Pro Glu Gln Pro Gly Arg Phe Ala Lys Leu Leu Leu Arg
            410                 415                 420

CTC CCT GCT CTG CGC TCC ATC GGC TTG AAA TGC CTG GAA CAC CTC TTC   1349
Leu Pro Ala Leu Arg Ser Ile Gly Leu Lys Cys Leu Glu His Leu Phe
        425                 430                 435

TTC TTC AAG CTC ATT GGA GAC ACT CCC ATC GAC AGC TTC CTC ATG GAG   1397
Phe Phe Lys Leu Ile Gly Asp Thr Pro Ile Asp Ser Phe Leu Met Glu
440                 445                 450

ATG TTG GAG ACC CCA CTG CAG ATC ACC TGA ACC TCC TCA GCT GCA GCT   1445
Met Leu Glu Thr Pro Leu Gln Ile Thr  *
455                 460

TCC CCA CCC AGG GTG ACC CTG GGC GGG CGG GTG TGT GTG TGTG          1488
```

(2) INFORMATION FOR SEQ ID NO:8:

(i) SEQUENCE CHARACTERISTICS:
        (A) LENGTH: 463 amino acids
        (B) TYPE: amino acid
        (D) TOPOLOGY: linear (ii) MOLECULE TYPE: protein (xi) SEQUENCE DESCRIPTION: SEQ ID NO:8:

Met Tyr Gly Asn Tyr Ser His Phe Met Lys Phe Pro Thr Gly Phe Gly

-continued

```
  1               5                  10                 15
Gly Ser Pro Gly His Thr Gly Ser Thr Ser Met Ser Pro Ser Val Ala
                20                 25                 30

Leu Pro Thr Gly Lys Pro Met Asp Ser His Pro Ser Tyr Thr Asp Thr
                35                 40                 45

Pro Val Ser Ala Pro Arg Thr Leu Ser Ala Val Gly Thr Pro Leu Asn
                50                 55                 60

Ala Leu Gly Ser Pro Tyr Arg Val Ile Thr Ser Ala Met Gly Pro Pro
 65                 70                 75                 80

Ser Gly Ala Leu Ala Pro Pro Gly Ile Asn Leu Val Ala Pro Pro
                85                 90                 95

Ser Ser Gln Leu Asn Val Val Asn Ser Val Ser Ser Glu Asp Ile
                100                105                110

Lys Pro Leu Pro Gly Leu Pro Gly Ile Gly Asn Met Asn Tyr Pro Ser
                115                120                125

Thr Ser Pro Gly Ser Leu Val Lys His Ile Cys Ala Ile Cys Gly Asp
                130                135                140

Arg Ser Ser Gly Lys His Tyr Gly Val Tyr Ser Cys Glu Gly Cys Lys
145                 150                155                160

Gly Phe Phe Lys Arg Thr Ile Arg Lys Asp Leu Ile Tyr Thr Cys Arg
                165                170                175

Asp Asn Lys Asp Cys Leu Ile Asp Lys Arg Gln Arg Asn Arg Cys Gln
                180                185                190

Tyr Cys Arg Tyr Gln Lys Cys Leu Val Met Gly Met Lys Arg Glu Ala
                195                200                205

Val Gln Glu Glu Arg Gln Arg Ser Arg Glu Arg Ala Glu Ser Glu Ala
                210                215                220

Glu Cys Ala Ser Ser Ser His Glu Asp Met Pro Val Glu Arg Ile Leu
225                 230                235                240

Glu Ala Glu Leu Ala Val Glu Pro Lys Thr Glu Ser Tyr Gly Asp Met
                245                250                255

Asn Val Glu Asn Ser Thr Asn Asp Pro Val Thr Asn Ile Cys His Ala
                260                265                270

Ala Asp Lys Gln Leu Phe Thr Leu Val Glu Trp Ala Lys Arg Ile Pro
                275                280                285

His Phe Ser Asp Leu Thr Leu Glu Asp Gln Val Ile Leu Leu Arg Ala
                290                295                300

Gly Trp Asn Glu Leu Leu Ile Ala Ser Phe Ser His Arg Ser Val Ser
305                 310                315                320

Val Gln Asp Gly Ile Leu Leu Ala Thr Gly Leu His Val His Arg Ser
                325                330                335

Ser Ala His Ser Ala Gly Val Gly Ser Ile Phe Asp Arg Val Leu Thr
                340                345                350

Glu Leu Val Ser Lys Met Lys Asp Met Gln Met Asp Lys Ser Glu Leu
                355                360                365

Gly Cys Leu Arg Ala Ile Val Leu Phe Asn Pro Asp Ala Lys Gly Leu
                370                375                380

Ser Asn Pro Ser Glu Val Glu Thr Leu Arg Glu Lys Val Tyr Ala Thr
385                 390                395                400

Leu Glu Ala Tyr Thr Lys Gln Lys Tyr Pro Glu Gln Pro Gly Arg Phe
                405                410                415

Ala Lys Leu Leu Leu Arg Leu Pro Ala Leu Arg Ser Ile Gly Leu Lys
                420                425                430
```

```
Cys Leu Glu His Leu Phe Phe Phe Lys Leu Ile Gly Asp Thr Pro Ile
    435                 440                 445

Asp Ser Phe Leu Met Glu Met Leu Glu Thr Pro Leu Gln Ile Thr
    450                 455                 460
```

(2) INFORMATION FOR SEQ ID NO:9:

(i) SEQUENCE CHARACTERISTICS:
        (A) LENGTH: 15 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:9:

```
GGATCCACCA TGTGC                                              15
```

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:10:

```
GCCACCCCTT CTAGAACTAG C                                       21
```

(2) INFORMATION FOR SEQ ID NO:11:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:11:

```
Ala Thr Pro Ser Arg Thr Ser
1               5
```

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:12:

```
GAATTCCACC ATGGGACCGG AT                                      22
```

(2) INFORMATION FOR SEQ ID NO:13:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (xi) SEQUENCE DESCRIPTION: SEQ ID NO:13:

```
Leu Gln Gln Gln His Arg Arg Leu Ala Gln Leu Leu Leu Ile Leu Ser
1               5                   10                  15

His Ile Arg His Met Ser Asn Lys Gly Met Glu His Leu Tyr Asn Met
            20                  25                  30

Lys Cys Lys Asn
            35
```

(2) INFORMATION FOR SEQ ID NO:14:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (xi) SEQUENCE DESCRIPTION: SEQ ID NO:14:

```
Arg Pro Ser Gln Pro Tyr Met Phe Pro Arg Met Leu Met Lys Ile Thr
1               5                   10                  15

Asp Leu Arg Gly Ile Ser Thr Lys Gly Ala Glu Arg Ala Ile Thr Leu
            20                  25                  30

Lys Met Glu Ile
            35
```

(2) INFORMATION FOR SEQ ID NO:15:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (xi) SEQUENCE DESCRIPTION: SEQ ID NO:15:

```
Lys His Asn Ile Pro His Phe Trp Pro Lys Leu Leu Met Lys Val Thr
1               5                   10                  15

Asp Leu Arg Met Ile Gly Ala Cys His Ala Ser Arg Phe Leu His Met
            20                  25                  30

Lys Val Glu Cys
            35
```

(2) INFORMATION FOR SEQ ID NO:16:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (xi) SEQUENCE DESCRIPTION: SEQ ID NO:16:

```
Pro Pro Gly Ser His Leu Leu Tyr Ala Lys Met Ile Gln Lys Leu Ala
1               5                   10                  15

Asp Leu Arg Ser Leu Asn Glu Glu His Ser Lys Gln Tyr Arg Cys Leu
            20                  25                  30

Ser Phe Gln Pro
            35
```

(2) INFORMATION FOR SEQ ID NO:17:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (xi) SEQUENCE DESCRIPTION: SEQ ID NO:17:

Asp Ser Met Ser Leu Val Phe Tyr Ala Lys Leu Leu Ser Ile Leu Thr
 1               5                  10                  15

Glu Leu Arg Thr Leu Gly Asn Gln Asn Ala Glu Met Cys Phe Ser Leu
            20                  25                  30

Lys Leu Lys Asn
        35

(2) INFORMATION FOR SEQ ID NO:18:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (xi) SEQUENCE DESCRIPTION: SEQ ID NO:18:

Tyr Pro Glu Gln Pro Gly Arg Phe Ala Lys Leu Leu Leu Arg Leu Pro
 1               5                  10                  15

Ala Leu Arg Ser Ile Gly Leu Lys Cys Leu Glu His Leu Phe Phe Phe
            20                  25                  30

Lys Leu Ile Gly
        35

(2) INFORMATION FOR SEQ ID NO:19:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (xi) SEQUENCE DESCRIPTION: SEQ ID NO:19:

His Pro Gly Asp Asp Gly Arg Phe Ala Gln Leu Leu Ile Arg Leu Pro
 1               5                  10                  15

Ala Leu Arg Ser Ile Ser Leu Lys Cys Asp His Leu Phe Leu Phe Arg
            20                  25                  30

Ile Thr Ser
        35

(2) INFORMATION FOR SEQ ID NO:20:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (xi) SEQUENCE DESCRIPTION: SEQ ID NO:20:

Arg Pro Asp Gln Pro Glu Phe Leu Ala Lys Leu Ile Glu Thr Met Pro
 1               5                  10                  15

Asp Leu Arg Thr Leu Ser Thr Leu His Thr Glu Lys Leu Val Val Phe
            20                  25                  30

Arg Thr Glu His
        35

(2) INFORMATION FOR SEQ ID NO:21:

(i) SEQUENCE CHARACTERISTICS:
     (A) LENGTH: 36 amino acids
     (B) TYPE: amino acid
     (D) TOPOLOGY: linear (ii) MOLECULE TYPE: peptide (xi) SEQUENCE DESCRIPTION: SEQ ID NO:21:

```
Tyr Pro Asn Gln Pro Thr Arg Phe Gly Lys Leu Leu Ile Arg Leu Pro
1               5                   10                  15
Ser Leu Arg Thr Val Ser Ser Gln Val Ile Glu Gln Leu Phe Phe Val
            20                  25                  30
Arg Leu Val Gly
        35
```

(2) INFORMATION FOR SEQ ID NO:22:

(i) SEQUENCE CHARACTERISTICS:
       (A) LENGTH: 36 amino acids
       (B) TYPE: amino acid
       (D) TOPOLOGY: linear (ii) MOLECULE TYPE: peptide (xi) SEQUENCE DESCRIPTION: SEQ ID NO:22:

```
Asp Pro Gln Pro Ala Ser Cys Leu Ser Arg Leu Leu Gly Lys Leu Pro
1               5                   10                  15
Glu Leu Arg Thr Leu Cys Thr Gln Gly Leu Gln Arg Ile Phe Cys Leu
            20                  25                  30
Lys Leu Glu Asp
        35
```

(2) INFORMATION FOR SEQ ID NO:23:

(i) SEQUENCE CHARACTERISTICS:
       (A) LENGTH: 36 amino acids
       (B) TYPE: amino acid
       (D) TOPOLOGY: linear (ii) MOLECULE TYPE: peptide (xi) SEQUENCE DESCRIPTION: SEQ ID NO:23:

```
Arg Pro Leu Glu Thr Ser Arg Phe Thr Lys Leu Leu Ile Lys Leu Pro
1               5                   10                  15
Asp Leu Arg Thr Thr Leu Asn Asn Met His Ser Glu Lys Leu Leu Ser
            20                  25                  30
Phe Arg Val Asp
        35
```

(2) INFORMATION FOR SEQ ID NO:24:

(i) SEQUENCE CHARACTERISTICS:
       (A) LENGTH: 17 base pairs
       (B) TYPE: nucleic acid
       (C) STRANDEDNESS: both
       (D) TOPOLOGY: linear (ii) MOLECULE TYPE: DNA (xi) SEQUENCE DESCRIPTION: SEQ ID NO:24:

AGGTCAGCGA GAGGTCA                                              17

(2) INFORMATION FOR SEQ ID NO:25:

```
        (i) SEQUENCE CHARACTERISTICS:
            (A) LENGTH: 13 base pairs
            (B) TYPE: nucleic acid
            (C) STRANDEDNESS: both
            (D) TOPOLOGY: linear (ii) MOLECULE TYPE: DNA (xi) SEQUENCE DESCRIPTION: SEQ ID NO:25:

AGGTCAGAGG TCA                                                              13

(2) INFORMATION FOR SEQ ID NO:26:

(i) SEQUENCE CHARACTERISTICS:
            (A) LENGTH: 14 base pairs
            (B) TYPE: nucleic acid
            (C) STRANDEDNESS: both
            (D) TOPOLOGY: linear (ii) MOLECULE TYPE: DNA (xi) SEQUENCE DESCRIPTION: SEQ ID NO:26:

AGGTCAGCAG GTCA                                                             14

(2) INFORMATION FOR SEQ ID NO:27:

(i) SEQUENCE CHARACTERISTICS:
            (A) LENGTH: 15 base pairs
            (B) TYPE: nucleic acid
            (C) STRANDEDNESS: both
            (D) TOPOLOGY: linear (ii) MOLECULE TYPE: DNA (xi) SEQUENCE DESCRIPTION: SEQ ID NO:27:

AGGTCAGCGA GGTCA                                                            15

(2) INFORMATION FOR SEQ ID NO:28:

(i) SEQUENCE CHARACTERISTICS:
            (A) LENGTH: 16 base pairs
            (B) TYPE: nucleic acid
            (C) STRANDEDNESS: both
            (D) TOPOLOGY: linear (ii) MOLECULE TYPE: DNA (xi) SEQUENCE DESCRIPTION: SEQ ID NO:28:

AGGTCAGCGA AGGTCA                                                           16

(2) INFORMATION FOR SEQ ID NO:29:

(i) SEQUENCE CHARACTERISTICS:
            (A) LENGTH: 12 base pairs
            (B) TYPE: nucleic acid
            (C) STRANDEDNESS: both
            (D) TOPOLOGY: linear (ii) MOLECULE TYPE: DNA (xi) SEQUENCE DESCRIPTION: SEQ ID NO:29:

AGGTCATGAC CT                                                               12
```

HETERODIMERIC NUCLEAR RECEPTORS PROTEINS, GENES ENCODING SAME, AND USAGE THEREOF

The present application is a continuation-in-part of U.S. application Ser. No. 08/119,186, now abandoned, which was granted a filing date of Feb. 22, 1994, as the national phase entry of PCT/US93/00639, filed Jan. 25, 1993, which is a continuation-in-part of U.S. application Ser. No. 07/825,667, filed Jan. 24, 1992, now abandoned, all of which are herein incorporated by reference.

FIELD OF THE INVENTION

The present invention relates to the field of nuclear receptors. Specifically, the present invention is based in part on the isolation of DNA encoding RX receptors and on the novel observation that two different types of nuclear receptors, retinoic acid receptors (RAR) and thyroid receptors (TR) dimerize with RX receptor (RXR) to form a heterodimer. The heterodimer is capable of binding to retinoic acid response elements (RARE), thyroid receptor response elements (TRE), or RX response elements (RXRE) at physiological conditions. Based on this observation, the present invention provides methods of identifying agents capable of binding the disclosed heterodimers, as well as identifying DNA sequences capable of being bound by the heterodimers. In addition, the present invention describes a method to identify mammalian-specific enzymes involved in RA metabolism, novel heteromeric partners of RXR and co-factors involved in the activation function of retinoic acid receptors.

BACKGROUND OF THE INVENTION

Retinoids are metabolites of vitamin A (retinol) which are thought to be important signaling molecules during vertebrate development and for controlling the differentiation state of several adult tissues (for reviews see Brockes, *Neuron* 2:1285–1294 (1989) and Brockes, *Nature* 345:766–768 (1990); Sherman, *Retinoids and Cell Differentiation,* Sherman, M. I. (ed). CRC Press (1986); Summerbell et al., *Trends in Neurosci.* 13:142–147 (1990)). Two families of nuclear retinoid receptors have been characterized. Retinoic acid receptors, which include RAR-α, RAR-β and RAR-γ (for reviews see Ruberte et al., *Development* 111:45–60 (1991b) and Chambon et al., *Seminars in Dev. Biol.* 2:153–159 (1991a)), have a high affinity for all-trans retinoic acid (RA) and belong to the same class of nuclear receptors as thyroid hormone (TRs), vitamin D3 (VDR) and ecdysone (EcR) receptors (see Koelle et al., *Cell* 67:59–77 (1991)). Members of the RXR family, RXR-α (Mangelsdorf et al., *Nature* 345:224–229 (1990) herein incorporated by reference), RXR-β (Hamada et al., *Proc. Natl. Acad. Sci. USA* 86:8289–8293 (1989) herein incorporated by reference) and RXR-γ respond to much higher concentrations of RA, and the natural ligand for RXRs appears to be a new stereoisomer of RA. RXRs belong to a different class of nuclear receptors which includes the Drosophila ultraspiracle (usp) gene product (Oro et al., *Nature* 347:298–301 (1990)).

Synthetic and natural DNA response elements (REs) have been characterized for TRs (Glass et al., *Nature* 329:738–741 (1987); Umesono et al., *Cell* 65:1255–1266 (1991) and see refs therein), RARs (Vasios et al., *Proc. Natl. Acad. Sci. USA* 86:9099–9103 (1989) and Vasios et al., *EMBO J.* 10:1149–1158 (1991); de Thé et al., *Nature* 343:177–180 (1990); Leroy et al., *Proc. Natl. Acad. Sci. USA* 88:10138–10142 (1991a) and refs therein), and RXRs (Mangelsdorf et al., *Cell* 66:555–561 (1991)). All of these REs consist of the repetition of a core motif, PuG$_T^G$TCA (Pu=purine) (or a related sequence), in different configurations with respect to both the orientation (direct or inverse repetition) and the spacing of the two motifs. The recognition of REs by a given receptor appears to be dependent on the actual sequence, orientation and spacing of the repeated motifs. Systematic studies of the influence of the spacing between directly repeated motifs have shown that RARs have a preference for 5 bp spaced motifs (Umesono et al., *Cell* 65:1255–1266 (1991)), whereas TRs and RXRs preferentially recognize motifs separated by 4 bp (Umesono et al., *Cell* 65:1255–1266 (1991)) and 1 bp (Mangelsdorf et al., *Cell* 66:555–561 (1991)), respectively. The presence of repeated motifs in these REs, and the demonstration that the glucocorticoid and oestrogen receptors bind as dimers to palindromic REs made up of similar motifs (Schwabe et al., *Trends Biochem. Sci.* 116:291–296 (1991); Luisi et al., *Nature* 352:497–505 (1991); and references therein) have suggested that RARs, TRs and RXRs also bind as dimers to REs. This possibility has been directly supported by in vitro binding evidence in the case of TRs and RARs (Glass et al., *Cell* 59:697–708 (1989); Glass et al., *Cell* 63:729–738 (1990); Lazar et al., *Mol. Cell. Biol.* 11:5005–5015 (1991); Forman et al., *Gene* 105:9–15 (1991)). However, it has also been reported that the in vitro binding of RAR (Glass et al., *Cell* 63:729–738 (1990)) and TR (Murray et al., *Mol. Endocrinol.* 3:1434–1442 (1989); Burnside et al., *J. Biol. Chem.* 265:2500–2504 (1990)) to REs can be greatly stimulated by the addition of, as yet, uncharacterized factor(s) present in nuclear extracts of a variety of cells. Furthermore, evidence has been presented indicating that these factors may form heterodimers with RAR (Glass et al., *Cell* 63:729–738 (1990)) and TR (Lazar et al., *Mol. Cell. Biol.* 11:5005–5015 (1991); Naär et al., *Cell* 65:1267–1279 (1991)), which bind with greater affinity to REs than the isolated receptors.

In the course of purification of RARs overexpressed in a variety of host-vector systems, these receptors lose the capability to bind the RA response element (RARE) of the RAR-β2 promoter (β-RARE) (de Thé et al., *Nature* 343:177–180 (1990); Sucov et al., *Proc. Natl. Acad. Sci. USA* 87:5392–5398 (1990); Mendelsohn et al., *Development* 113:723–734 (1991)), which could be recovered by addition of HeLa cell nuclear extracts, irrespective of the source of over expressed RARs.

Retinoids have been used in the treatment of actinally aged skin (Ellis et al., *Pharmacol. Skin.* 3:249–253 (1989)), various types of dermatoses (Gollnick, *Dermatological* 175 (1): 182–195 (1987)), disorders of keratinization (Happle et al., *Dermatological* 175(1):107–124 (1987)), rheumatoid arthritis (Brinckerhoff et al., 1985 *Retinoids, Differentiation and Disease,* Pitman, London (Ciba Foundation Symposium 113) p. 191–211), basal cell carcinoma (Peck, *Dernatological* 175(1):138–144 (1987)), and systemic sclerosis (Maurice et al., *Pharmacol. Skin.* 3:235–239 (1989)). In addition, retinoids have been demonstrated to possess immunostimulating activity (Dennert, 1985 *Retinoids, Differentiation and Disease,* Pitman, London (Ciba Foundation Symposium 113) p. 117–131), inhibit epidermal terminal differentiation (Lichti et al., 1985 *Retinoids, Differentiation and Disease,* Pitman, London (Ciba Foundation Symposium 113) p. 77–89), modulate carcinogenesis in the urinary bladder (Hicks et al., 1985 *Retinoids, Differentiation and Disease,* Pitman, London (Ciba Foundation Symposium 113) p. 168–190), regulate differentiation in embryonal carcinoma cells (Sherman et al., 1985 *Retinoids, Differentiation and Disease,* Pitman, London (Ciba Foundation Symposium 113) p. 42–60), regulate differentiation in tracheal epithelial cells (Jetten et al., 1985 *Retinoids, Differentiation and Disease,* Pitman, London (Ciba Foundation Symposium 113) p. 61–76), inhibit neoplastic transformation (Bertram et al., 1985 *Retinoids, Differentiation and Disease,* Pitman, London (Ciba Foundation Symposium 113) p. 29–41), possess anti-inflammatory activity (Ney et al., *Dermatological* 175(1):93–99 (1987)), modulate melanoma growth (Amos et al., *Pharmacol. Skin.* 3:29–36 (1989)), and may play an important role in cholesterol metabolism (Rottman et al., *Mol. Cell. Biol.* 11:3814–3820 (1991)).

It is unknown what the molecular basis is for the various effects retinoids are able to regulate. One possibility is that the various effects regulated by retinoids are caused by the interactions of the retinoid ligand with a tissue specific RAR receptor. Alternatively, the various receptors may bind to different RE motifs with differing affinities.

Using the observations disclosed in the present invention, it is now possible to examine the interactions of retinoids, or derivatives thereof, with specific RAR/RXR, and TR/RXR heterodimeric combinations. Additionally, each of the heterodimeric combinations can be examined for it's affinity for different RARE, TRE or RXRE sequences. Such a system will lead to a better understanding of the biological effects stimulated by retinoids and lead to the identification of the next generation of retinoids.

SUMMARY OF THE INVENTION

The present invention is based in part on the novel observation that three types of nuclear receptors, RAR, RXR and TR, can form heterodimers at physiological conditions which possess a greater affinity for binding to the various RE motifs than each of the respective homodimers.

Based on this observation the present invention provides heterodimeric proteins which are comprised of two subunits, one of the subunits is either a RAR or TR, and the other subunit is a RXR.

The present invention further provides highly purified subtypes of RXR. The highly purified forms of RXR have a specific activity from about 1461 to 7,750,000 cpm/µg. Examples of the amino acid sequences of various RXR's of the present invention are depicted in Sequence ID No. 2 (mRXR-β), Sequence ID No. 4 (hRXR-β), Sequence ID No. 6 (mRXR-α), and Sequence ID No. 8 (mRXR-γ). The RXR's of the present invention includes monomers and multimers (such as homodimers) of each of the isoforms and subtypes of RXR.

The present invention further provides methods of purifying subtypes and isoforms of RXR. In detail, RXR's can be purified by:

a) contacting a sample containing a RXR protein with a DEAE chromatography column in the presence of a buffer containing from about 50 mM KCl;

b) retrieving the RXR in the flow through fraction from the column;

c) contacting the flow through fraction (b) with a HEP-UG column;

d) eluting the RXR from the column using from about 290 mM KCl;

e) contacting the KCl eluted RXR (d) with a phenyl-5PW column;

f) eluting the RXR from the column using from about 250 mM ammonium sulfate;

g) contacting the ammonium sulfate eluted RXR (f) with a HEP-TSK column;

h) eluting the RXR from the column using from about 250 mM KCl;

i) contacting the KCl eluted RXR (h) with a HAP-TSK column; and j) eluting the RXR from the column using from about 150 mM potassium phosphate.

The present invention further provides DNA sequences which are capable of binding to any one of the above heterodimers or homodimers.

The present invention further provides antibodies which are capable of binding to any one of the above heterodimers or homodimers.

The present invention further provides methods of identifying agents capable of binding to the heterodimers of the present invention comprising the steps of:

1) incubating an agent with one of the heterodimers of the present invention; and 2) determining whether the agent bound to the heterodimer.

The present invention further provides methods of identifying agents capable of inducing transcription of a sequence operably linked to an RARE, TRE, or RXRE. These methods comprise the steps of:

1) incubating a cell, organism, or extract thereof, which has been altered to express one or more of the dimers described herein, with an agent, wherein said cell or organism contains a reporter sequence operably linked to an RARE; and 2) assaying for the expression of the reporter sequence.

The present invention also provides methods of directing the expression of a DNA sequence in response to a specific agent by first identifying a dimer/RE/agent combination which is capable of inducing transcription in the above described assay and then altering a cell or organism such that it will express the heterodimer and contains a DNA sequence, operably linked to the RE.

The present invention further provides DNA sequences which encode members of RXR family of receptors. Specifically, sequences encoding 1 isoform of mRXR-β (Sequence ID No. 1), 1 isoform of hRXR-β (Sequence ID No. 3), 1 isoform of mRXR-α (Sequence ID No. 5), and 1 isoform of mRXR-γ (Sequence ID No. 7), are described.

BRIEF DESCRIPTION OF THE DRAWINGS

FIGS. 2A–2B. Amino acid alignment of hRXR-β with mRXR-α, -β and -γ.

Figure 3A:
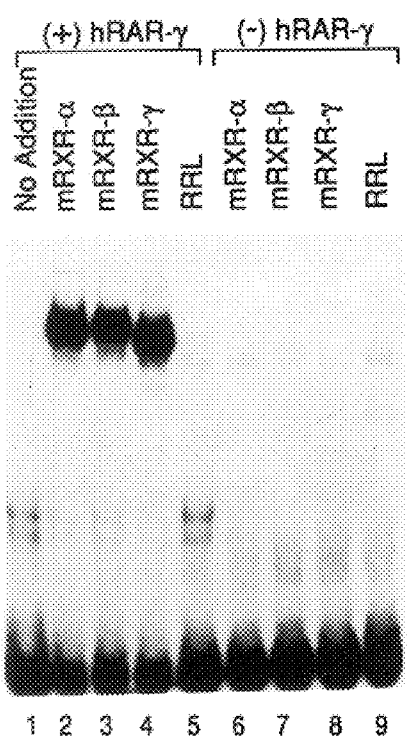

Amino acid identity is indicated by a star (between all RXRs) and/or a dot (between human and mouse RXR-β). Based on homology with other nuclear receptors, the DNA (region C) and ligand binding (region E) domains are indicated. The amino acid sequences of seven peptides obtained by tryptic digestion of purified HeLa cell RBF are indicated in shaded boxes. Open headed arrows on p24 and p27 indicate amino acids from which PCR primers were deduced (see text). Note that p25 and p28 were the only peptides obtained which could discriminate between members of the RXR family. Genbank accession numbers for the nucleotide M84817, M84818, M84819, M84820 sequence of mRXR-α, -β and -γ and hRXR-β are respectively:

FIGS. 3A and B. Cloned RXRs stimulate binding of hRARs to the β-RARE

FIG. 3A. Approximately 10 fmols of bacterially-expressed hRAR-γ were incubated with the β-RARE in the absence (lane 1) or presence of equal molar amounts of in vitro translated mRXRs as indicated. As a control, a volume of rabbit reticulocyte lysate (RRL) corresponding to that which contained mRXRs (2 µl) was also mixed with hRAR-γ (lane 5). Binding of RXRs and RRL to the β-RARE in the absence of hRAR-γ is shown in lanes 6–9.

Figure 3B:
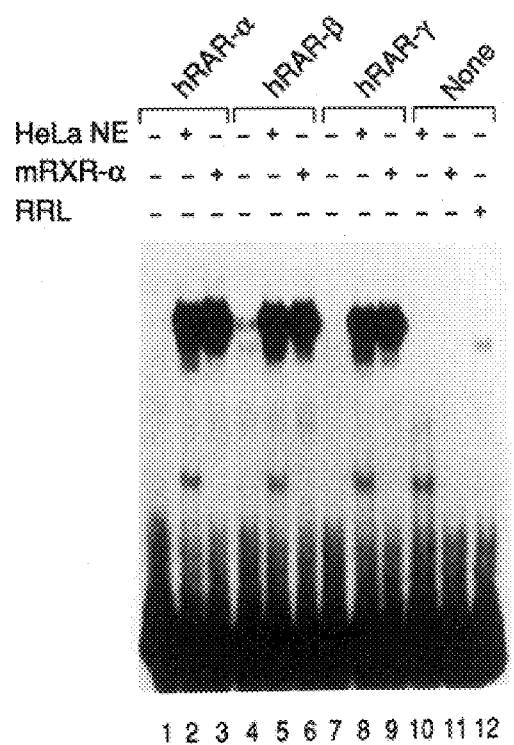

FIG. 3B. RARs (~10 fmols of each receptor) were prepared by in vitro translation and incubated with the β-RARE in the absence or presence of either HeLa nuclear extract (3 µg of protein) or mRXR-α (~10 fmols, translated in vitro). Control lanes 10–12 correspond to incubation of HeLa NE, mRXR-α and RRL, respectively, with the β-RARE in the absence of RARs.

Figure 4A:
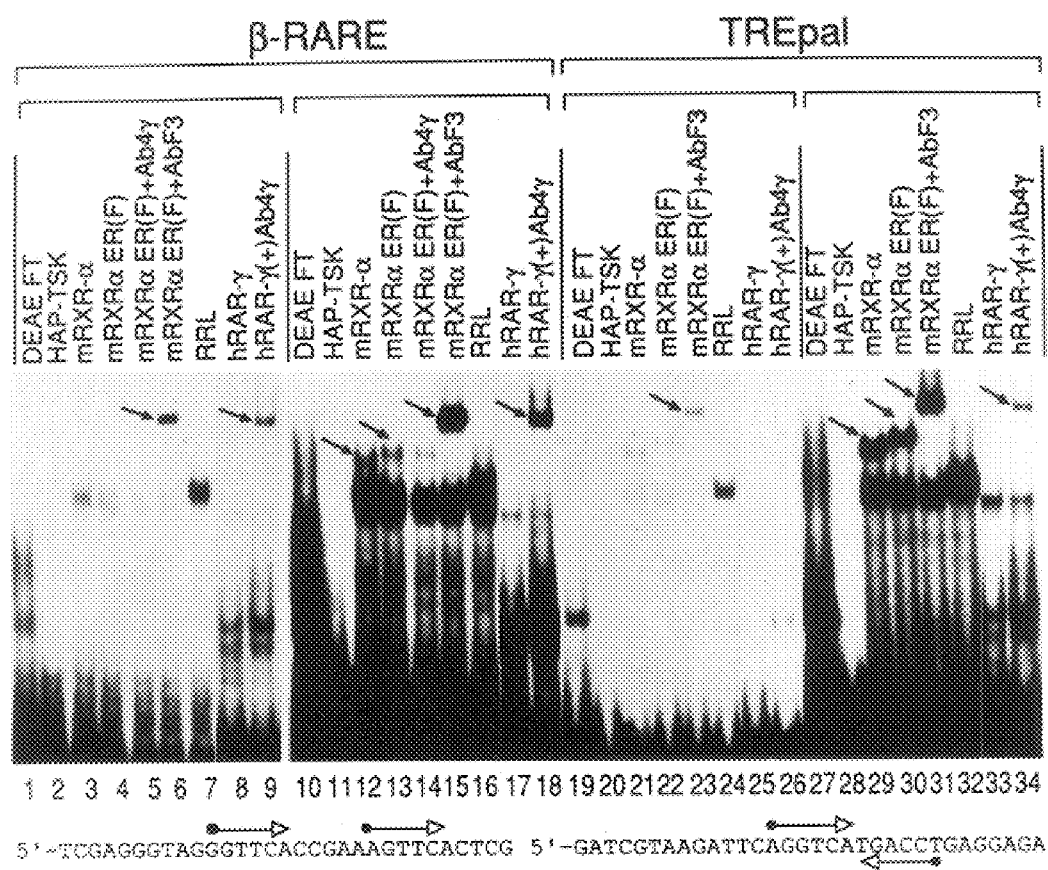

FIGS. 4A and B. Binding of hRAR-γ, mRXR-α and chicken TRα1 to the β-RARE and TREpal.

FIG. 4A. Binding of isolated RAR and RXR to β-RARE and TREpal probes. Lanes 1–9 and 10–18 (β-RARE binding) are derived from the same gel; however, the latter lanes have been exposed for a longer period of time to visualize weak complexes. Similarly, lanes 19–26 and 27–34 (TREpal binding) are identical except that the latter lanes were exposed longer for the same purpose. Gel retardation assays in which partially purified (DEAE FT, 2 µg), or purified (HAP-TSK,1 ng) HeLa cell RBF, mRXR-α (~10 fmols translated in vitro), mRXRαER(F) (~10 fmols translated in vitro) and bacterially-expressed hRAR-γ (~10 fmols) were incubated with the β-RARE (the sequence of the upper strand of this probe is given) as indicated. In the presence of specific antibodies, mRXRαER(F) (lanes 6 and 15) and hRAR-γ (lanes 9 and 18) supershifted complexes were observed, whereas no mRXRαER(F) complex was supershifted with a non-specific antibody (Ab4γ, lanes 5 and 14). Lanes 19–34 correspond exactly to lanes 1–18 with regard to sample contents but the former lanes represent binding to a TREpal (the sequence of the upper strand of this probe is given). Arrows denote specific complexes.

Figure 4B:
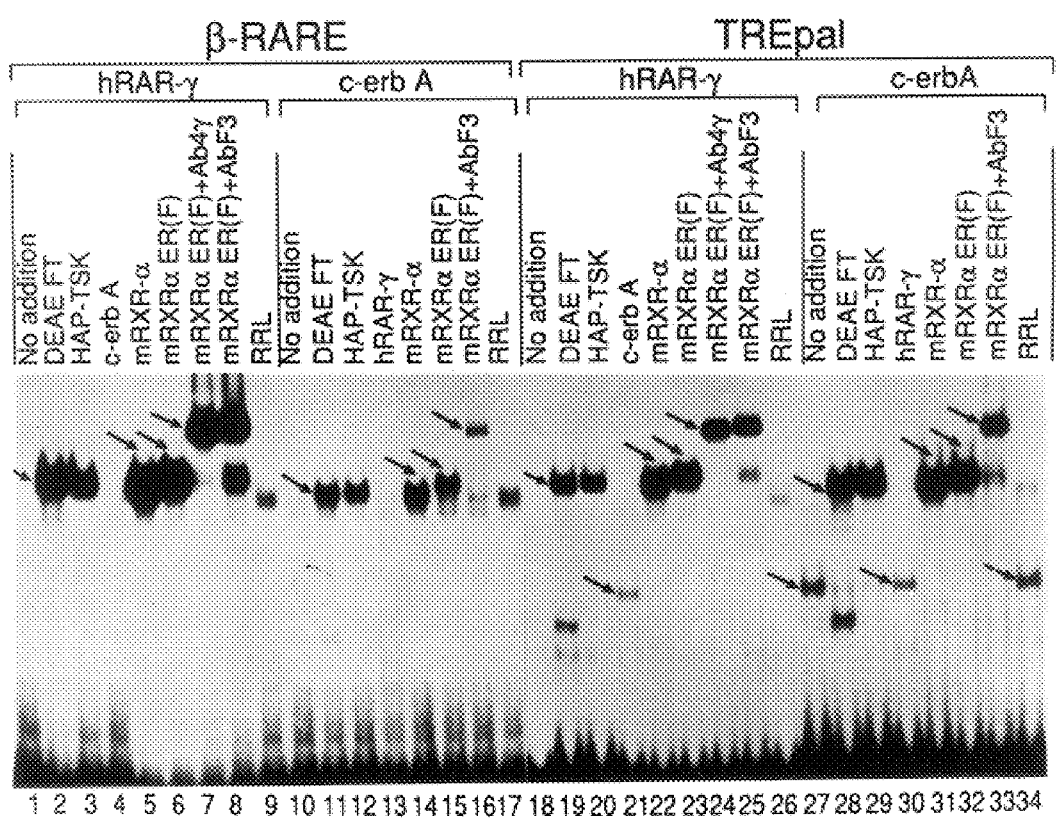

FIG. 4B. Cooperative binding of RXR and either RAR or c-erbA to β-RARE and TREpal probes. Note that the exposure time of these gels was identical to that of lanes 1–9 and 19–26 in part A. Lanes 1–9 represent bacterially-expressed hRAR-γ (~10 fmols) binding to the β-RARE alone (lane 1) or in the presence of DEAE-FT or HAP-TSK preparations of HeLa cell R0F, c-erbA (~10 fmols translated in vitro), mRXR-α, mRXRαER(F) or RRL as indicated. The hRAR-γ/mRXRαER(F)/β-RARE complex (lane 6) was supershifted by both Ab4-γ (lane 7) and AbF3 (lane 8). Lanes 10–17 depict c-erbA (~10 fmols, translated in vitro) binding to the β-RARE alone (lane 10) or in the presence of DEAE FT or HAP-TSK preparations of HeLa cell RBF, hRAR-γ, mRXR-α, mRXRαER(F) or RRL as indicated. A c-erbA/mRXRαER(F)/β-RARE supershifted complex was observed with addition of AbF3 (lane 16). Lanes 18–34 correspond exactly to lanes 1–17 except the former lanes represent cooperative binding interactions on the TREpal. Arrows denote specific complex formation. Amounts of receptors were as indicated in part A.

FIG. 5. Chemical crosslinking and co-immunoprecipitation of RAR and RXR

Figure 5A:
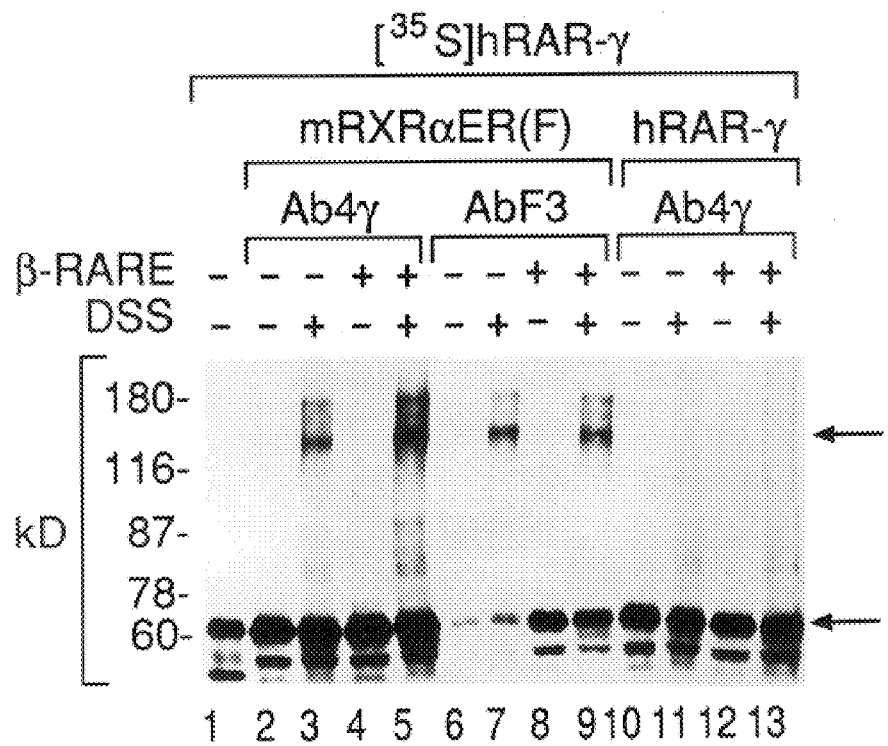

FIG. 5A. [$^{35}$S]hRAR-γ (~50 fmols) was incubated with an equal molar amount of either unlabeled hRAR-γ or mRXRαER(F) as indicated. Incubations were carried out in the absence or presence of 500 fmols of β-RAREwt and DSS (final concentration of 1 mM) as indicated. The upper arrow denotes the cross-linked product observed in lanes 3, 5, 7 and 9 and the lower arrow corresponds to the [$^{35}$S]hRAR-γ monomer. Lane 1 is a reference lane for the migration of [$^{35}$S]hRAR-γ.

Figure 5B:
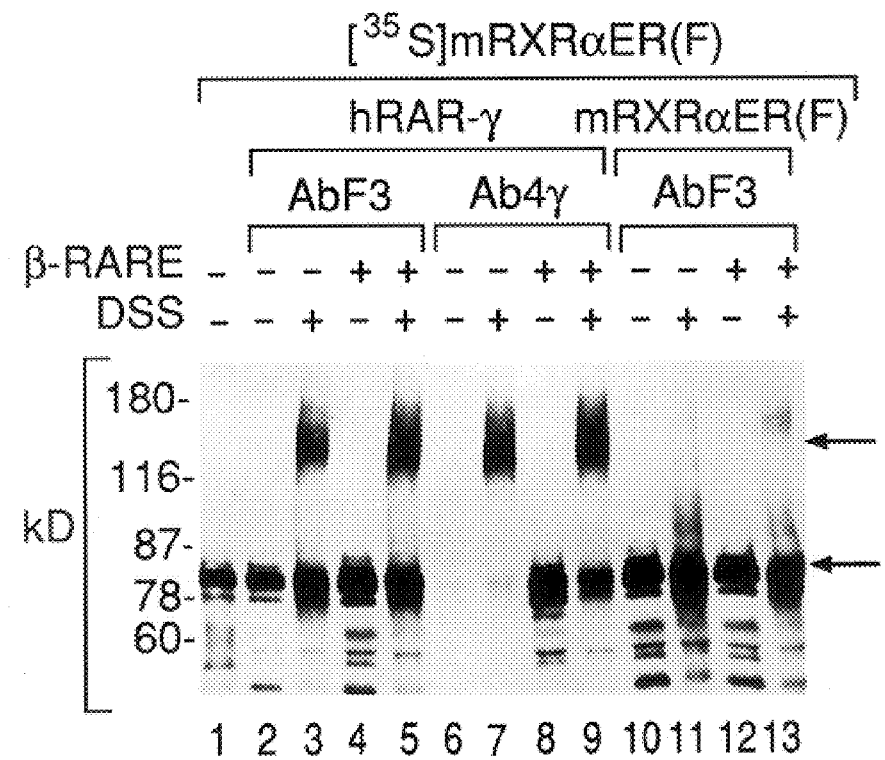

FIG. 5B. Part B, is similar to A, except that the labeled receptor is [$^{35}$S]mRXRαER(F). Crosslinked complexes and [$^{35}$S]mRXRαER(F) monomers are indicated by the upper and lower arrows, respectively. Additions of unlabeled receptors, β-RARE, DSS and precipitating antibody are as indicated. Lane 1 is a reference lane for migration of [$^{35}$S]mRXRαER(F).

Figure 6A:
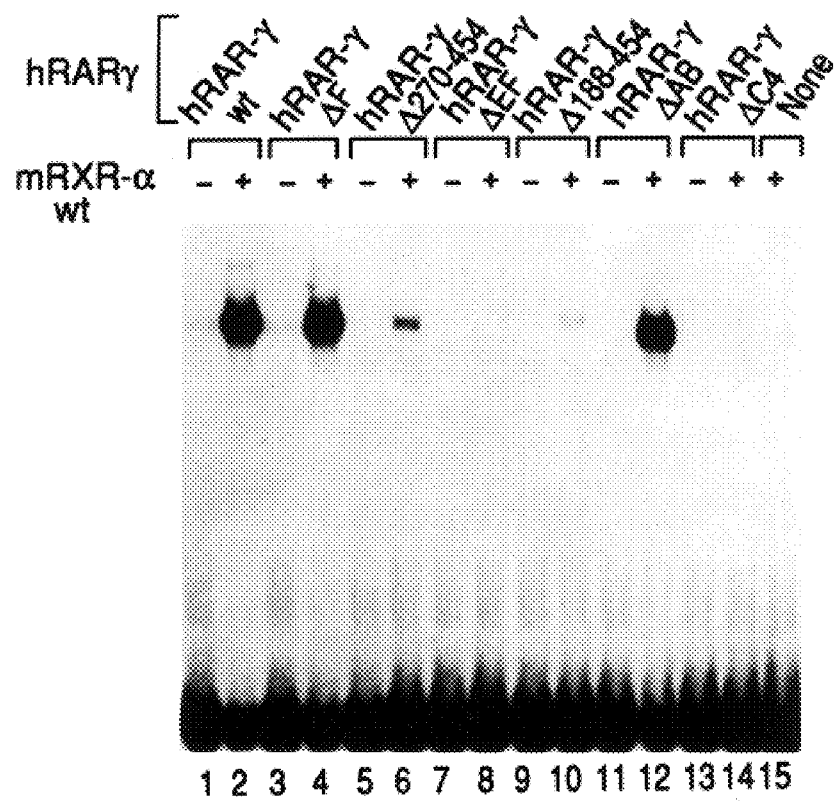

FIGS. 6A and B. Characterization of RAR/RXR interaction by deletion and mutational analysis of each protein FIG. 6A. DNA binding of hRAR-γ mutants to the β-RARE. hRAR-γ mutants were translated in vitro (using RRL) and the amount of translated protein normalized (~10 fmol/assay) as described (see experimental procedures). Gel retardation assays were carried out in the presence or absence of an equal molar amount of mRXR-α as indicated. After autoradiography, specific complexes were excised and counted in a scintillation counter to quantify the extent of complex formation by each mutant. Shown is a schematic diagram of the mutants and the corresponding activity relative to hRAR-γ wt.

Figure 6B:
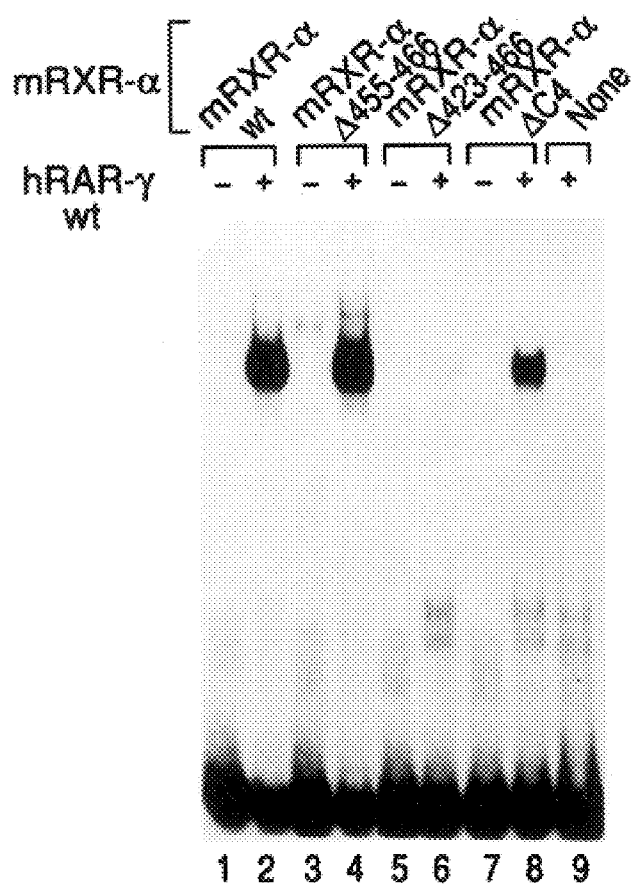

FIG. 6B. Binding of mRXR-α mutants to the β-RARE was similarly assessed. mRXR-α mutants were translated in vitro and the gel retardation assay carried out in the presence or absence of an equal molar amount (~10 fmols) of bacterially-expressed hRAR-γ. The experiment was quantified as described in part A. Note that the DNA binding properties of one mutant, mRXR-αΔ449–466, are not shown in the gel but the complex formed in the presence of this mutant and hRAR-γ was indistinguishable from that of mRXR-α or mRXRαΔ455–466.

Figure 7:
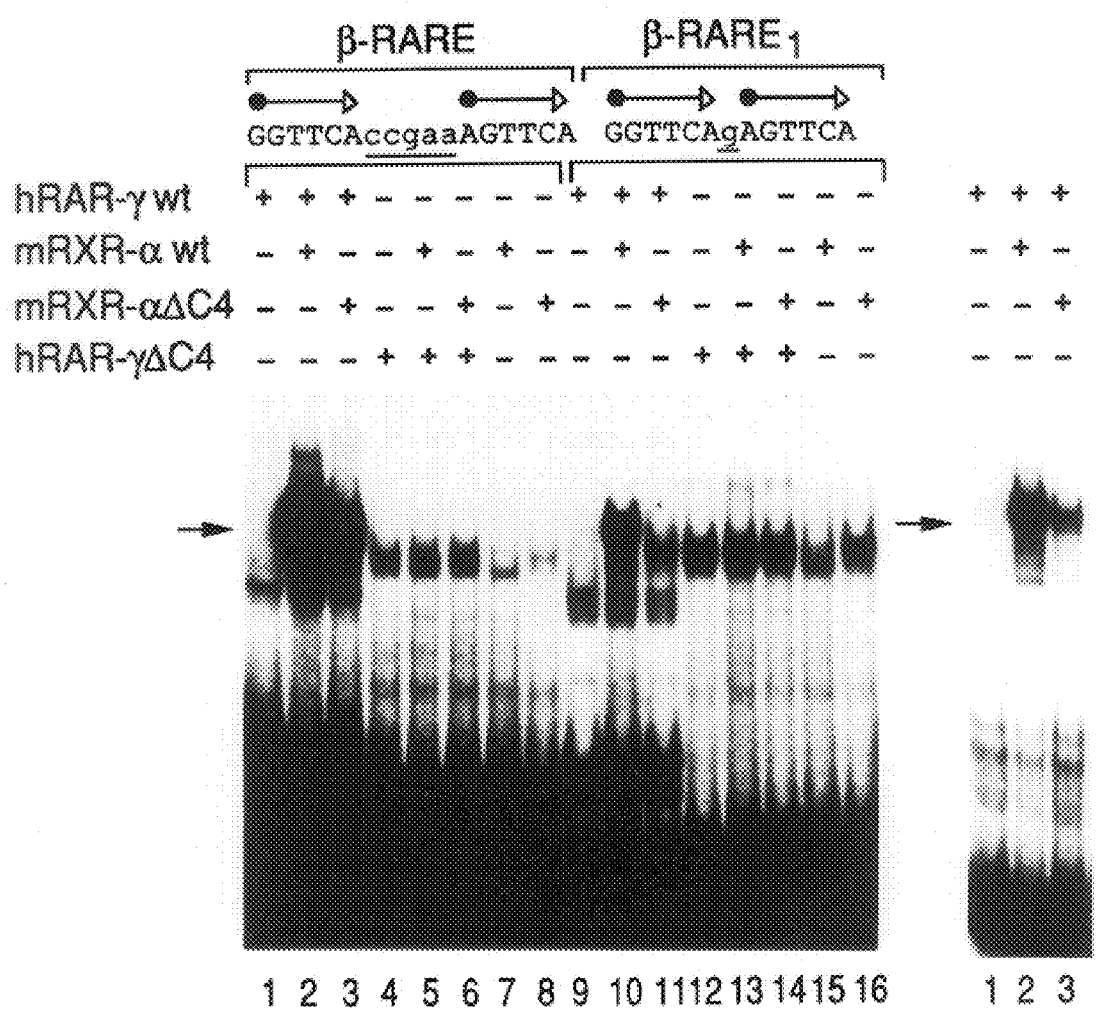

FIG. 7. Comparison of RAR/RXR complex formation on direct repeats of different inter-repeat spacing ~10 fmols of bacterially-expressed hRAR-γ, in vitro translated hRAR-γ-ΔC4, mRXR-αwt or mRXR-αΔC4 were incubated in various combinations as indicated with the β-RARE (lanes 1–8) or β-RARE1 (lanes 9–16) probes (the repeated motifs of each are given). The right panel shows a lesser exposure of lanes 1–3. Specific complexes are indicated by the arrow. Other bands present are due to non-specific *E. coli* or RRL proteins (data not shown).

Figure 8:
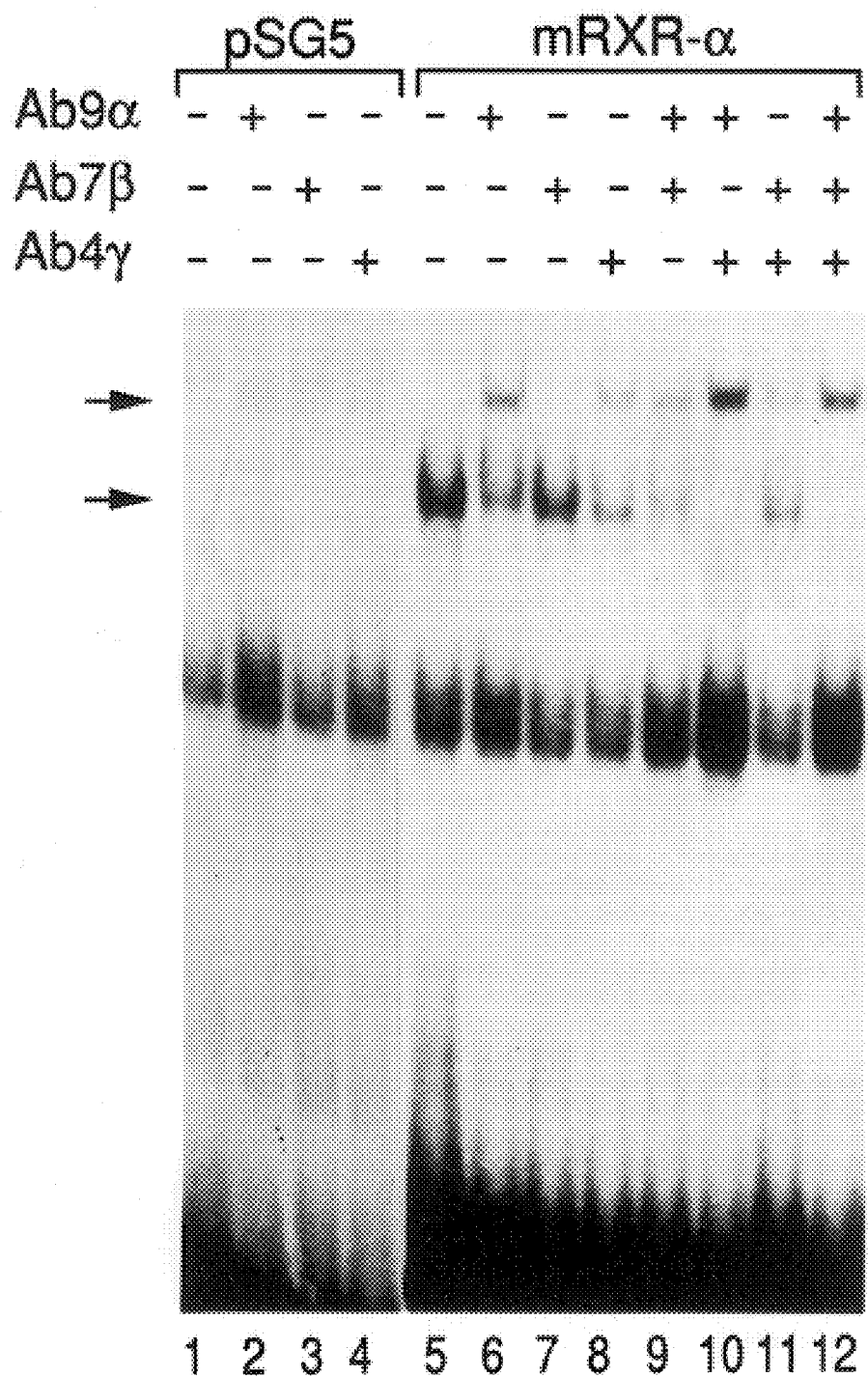

FIG. 8. Binding of Cos cell-expressed mRXR-α to the β-RARE

Gel retardation assays in which an aliquot (10 μg of protein) of Cos cell WCE, prepared from cells transfected with mRXR-α (lanes 5–12) or the parental expression vector (pSG5, lanes 1–4) was incubated with the β-RARE in the presence or absence of anti-RAR monoclonal antibodies Ab9α, Ab7β and Ab4γ as indicated. The upper and lower arrows denote positions of supershifted and non-supershifted complexes, respectively.

FIG. 9. Amino acid sequence alignment of a subdomain implicated in the dimerization potential of selected nuclear receptors Region of the mouse estrogen receptor (MER) which is critical for (homo)dimerization (Fawell et al., *Cell* 60:953–962, stars indicate residues which when mutated destroyed the homodimerization potential of the receptor). Residues contained in shaded boxes correspond to heptad repeat 9 proposed by Forman et al., *Mol. Endocrinol.* 4:1293–1301 (1990). In the case of mRXR-α, usp and E75A, another heptad (underlined) repeat is possible. Proline residues, which may impart flexibility to this region are also indicated. The sequences shown are from the following references: mER, (White et al., *Mol. Endocrinol.* 1:735–744 (1987) (see also Fawell et al., *Cell* 60:953–962 (1990)); hRAR-γ, Krust et al., *Proc. Natl. Acad. Sci. USA* 86:5310–5314 (1989); cTR-α1, Sap et al., *Nature* 34:635–640 (1986); hVDR, Baker et al., *Proc. Natl. Acad. Sci. USA* 85:3294–3298 (1988); EcR, Koelle et al., *Cell* 67:59–77 (1991); mRXR-α, the current report; usp, Oro et al., *Nature* 347:298–301 (1990); E75A, Segraves et al., *Genes and Dev.* 4:204–219 (1990); svp, Mlodzik et al., *Cell* 60:211–224 (1990); rNGFI-B, Milbrandt, *Neuron* 1:183–188 (1988); hear-1, Miyajima et al., *Cell* 57:31–39 (1989).

Figure 10A:
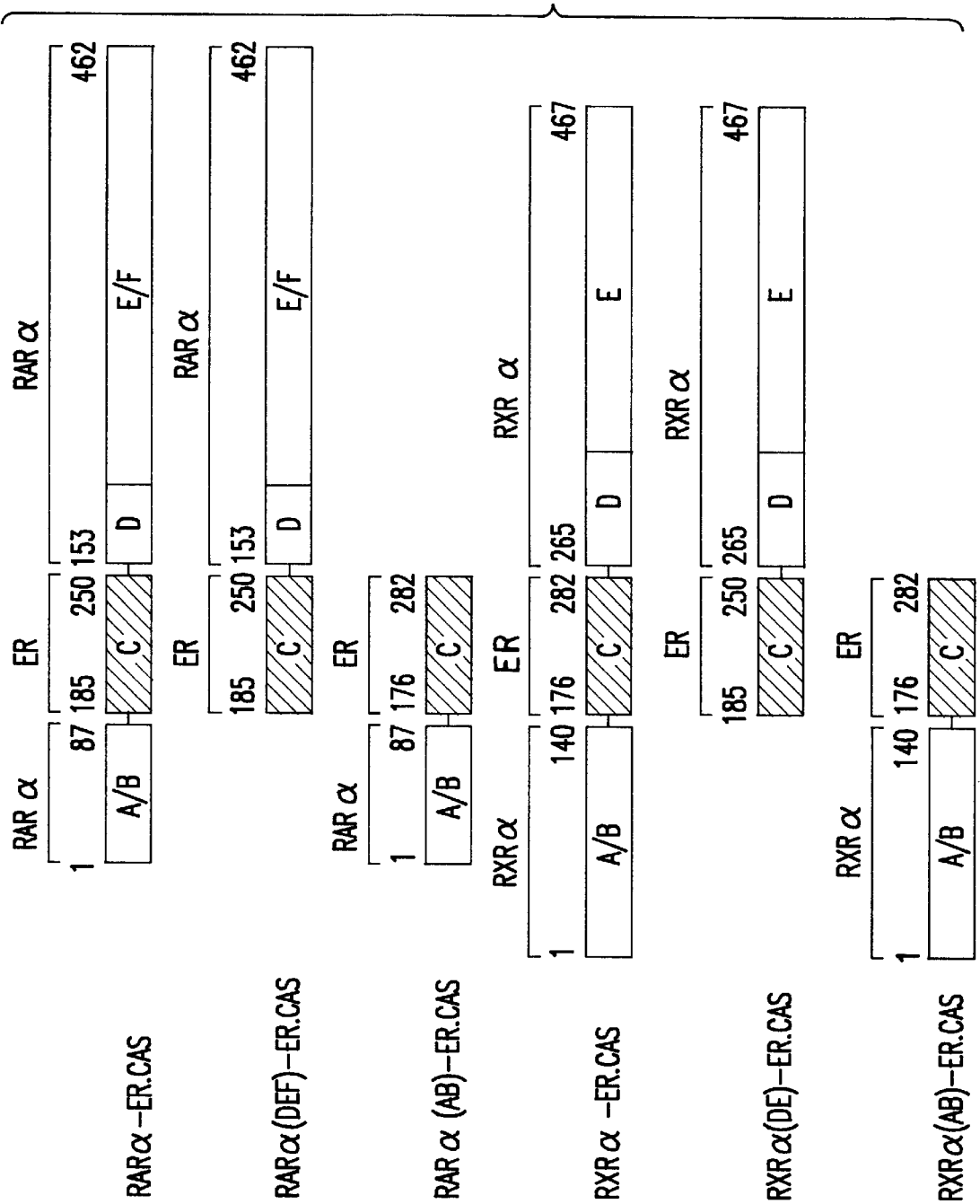

FIGS. 10A, B, and C. Chimeric RARα and RXRα activate transcription autonomously in yeast FIG. 10A, Schematic representation of chimeric RARα1-ER.CAS and RXRα-ER(C) receptors and their truncated derivatives. Numbers refer to amino acid positions. The chimeric receptors contain the DBD of human ER (hatched box) and were expressed from the constitutive yeast PGK (phosphoglycerate kinase) gene promoter in the 2μ-derived yeast multicopy plasmids YEp10 and YEp90 (Pierrat, B. et al., *Gene* 119:237–245 (1992)). FIGS. 10B1 and 10B2, Dose responses of RARα1-ER.CAS and RXRα-ER(C) to all-trans retinoic acid (T-RA) and 9-cis retinoic acid (9C-RA). The chimeric receptors RARα1-ER.CAS and RXRα-ER(C) were expressed in a reporter strain (PL3) which contains a chromosomally integrated 3ERE-URA3 reporter gene (Pierrat, B. et al., *Gene* 119:237–245 (1992)), in the presence of T-RA or 9C-RA at the concentrations indicated. Transcription of the reporter gene was determined by measuring the specific activity of the URA3 gene product OMPdecase (orotidine-5'-monophosphate decarboxylase), and is represented as fold induction above the level of OMPdecase activity observed in the absence of ligand. FIGS. 10C1 and 10C2, Retinoic acid derivatives differentially induce transactivation by RARα1-ER.CAS and RXRαER(C). Induction of reporter activity in the yeast strain PL3 expressing RARα1-ER.CAS or RXRα-ER(C) in the presence of the following ligands; T-RA, 9C-RA, T-ddRA (all-trans 3,4-didehydroretinoic acid), 9C-ddRA (9-cis 3,4-didehydroretinoic acid). The final concentration of ligand was $10^{-6}$ M. The level of transactivation of the reporter gene is given as units of OMPdecase activity (nmoles of substrate transformed/min/mg protein).

Figure 11A:
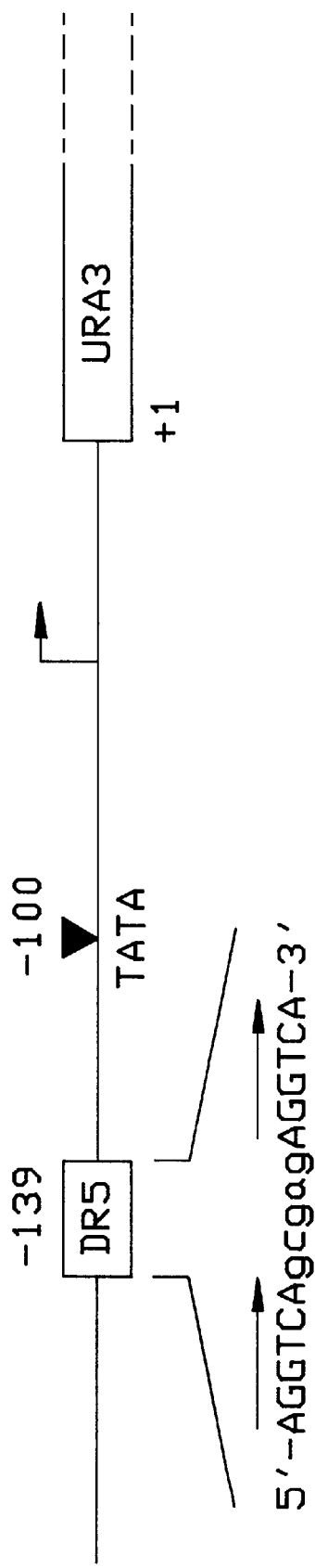

FIGS. 11A and B. RARα and RXRα cooperate to activate a RARE reporter gene in yeast.

Figure 11B:
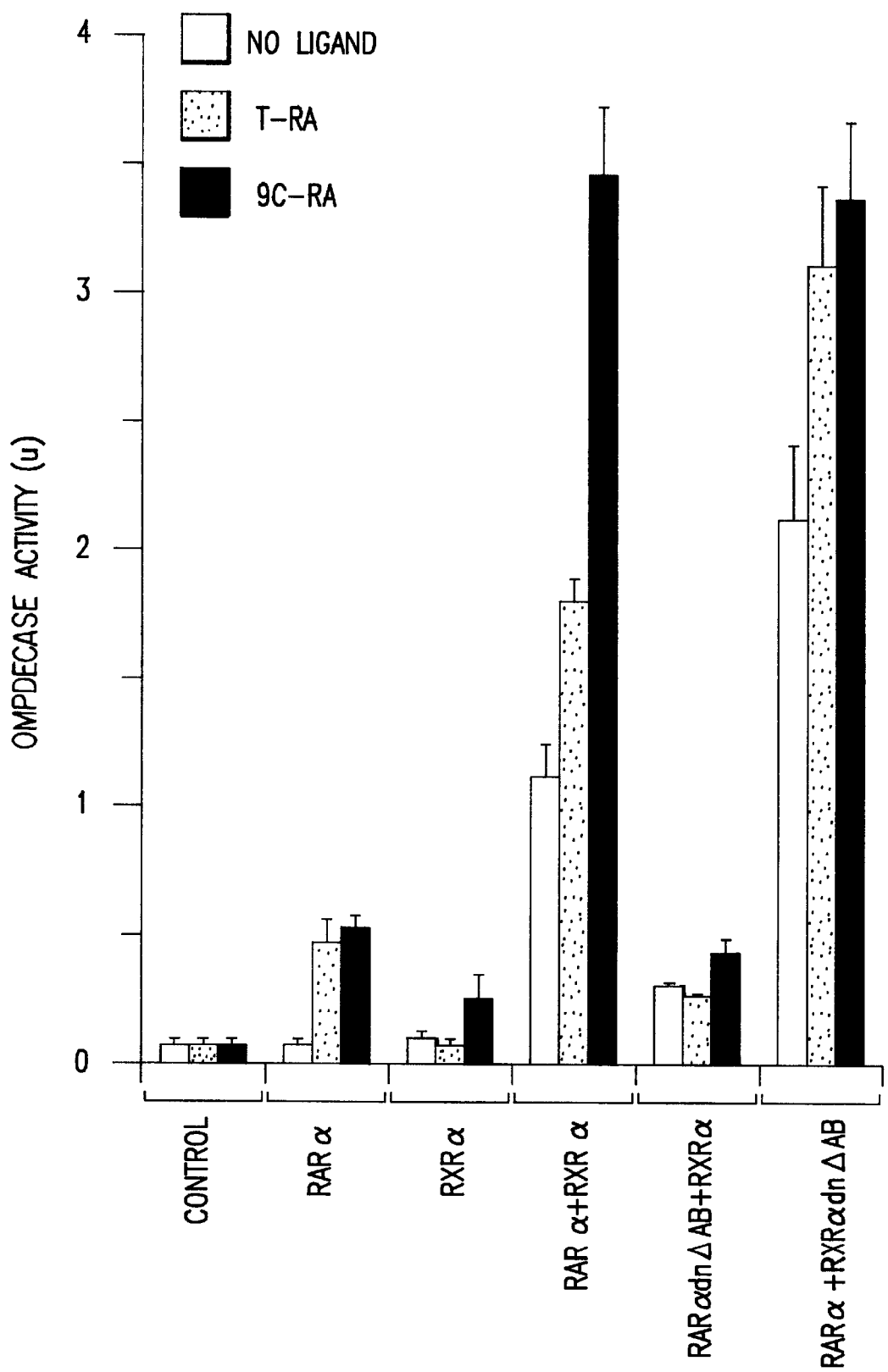

FIG. 11A, Schematic representation of the promoter region of the DR5-URA3 reporter used in transactivation experiments. URA3 promoter sequences required for both basal and activated transcription were deleted and replaced with a RARE sequence. This element consists of a direct repeat of the motif 5'-AGGTCA-3' separated by five base pairs (DR5; the sequence of which is shown). The position of the DR5 and the TATA box relative to the ATG start codon (+1) are also shown, and the bent arrow indicates the approximate site of initiation of transcription of the URA3 mRNA. The reporter gene was maintained in yeast strain YPH250 on a centromeric plasmid. FIG. 11B, RXRα enhances RARE activity on a DR5 element in yeast. OMP-decase activities measured in extracts of transformants containing the DR5-URA3 reporter plasmid and multicopy plasmids (see FIG. 10) expressing RARα, RARαdnΔAB, RXRα, RXRαdnΔAB in the combinations indicated, or parental vectors (control), in the presence or absence of ligand (T-RA or 9C-RA; final concentration 5×$10^{-7}$ M). In RARαdnΔAB and RXRαdnΔAB, the A/B regions and part of the C-terminus of RARα and RXRα, respectively, have been deleted, resulting in transcriptionally inactive mutant derivatives (data not shown). The mean values and standard deviations presented are derived from at least two experiments using three separate transformants for each clone. FIGS. 11C1 and 11C2, 9C-RA induces RXRα activity on a DR5-reporter gene in yeast. Dose responses to T-RA and 9C-RA in transformants containing the DR5-URA3 reporter plasmid, and coexpressing RARα with RXRα or RXRαdn as shown. RXRαdn is a dominant negative receptor in mammalian cells and contains a C-terminal deletion (Durand, B. et al., *Cell* 71:73–85 (1992)). Transactivation is represented as fold induction of reporter activity above the value obtained in the absence of ligand.

Figure 12:
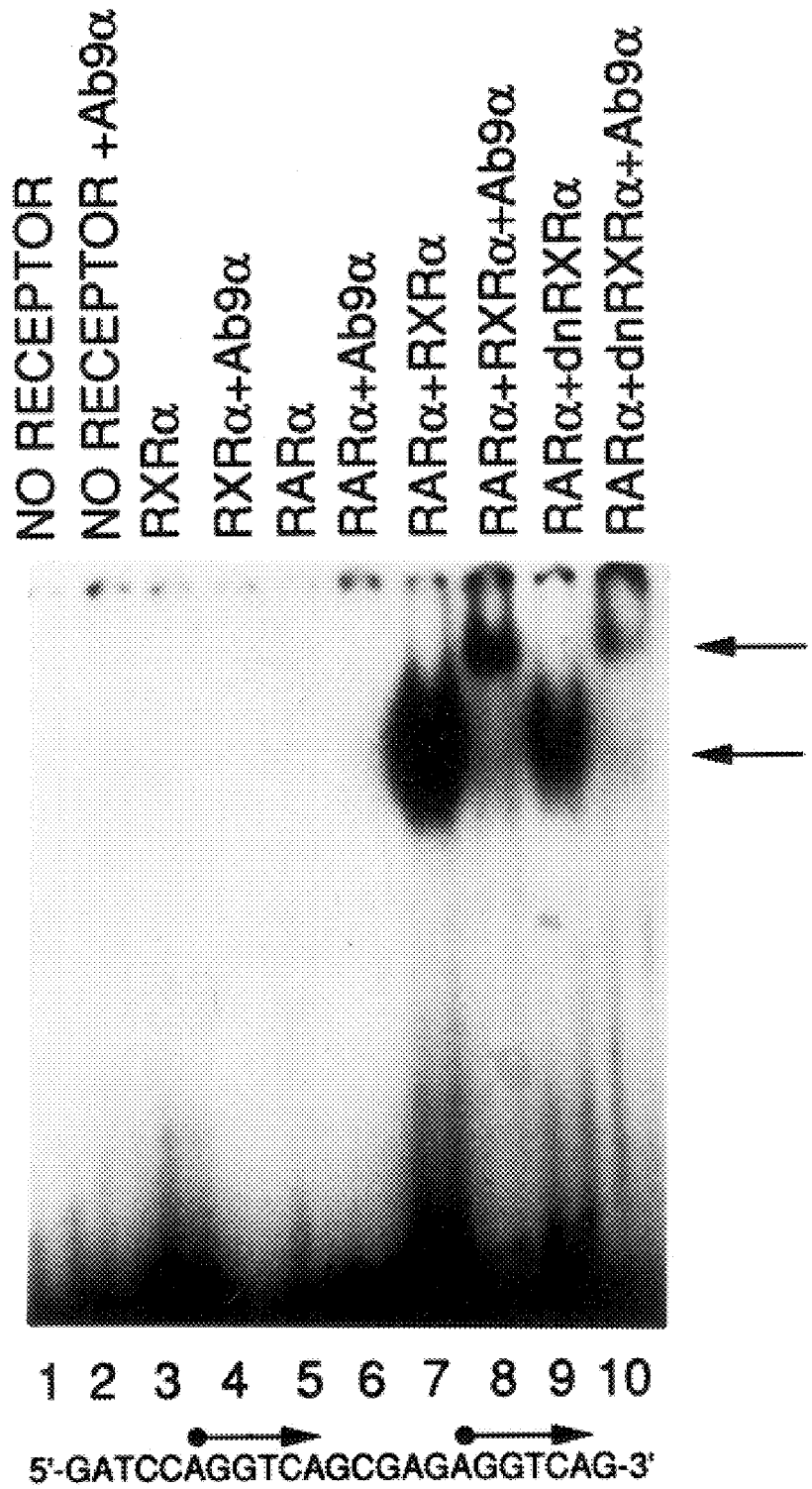

FIG. 12. RARα and RXRα produced in yeast cooperate for DNA-binding to a RARE in vitro.

Gel retardation assays were performed using a labelled DR5 probe (the sequence of which is indicated below the figure) and cell-free extracts prepared from yeast transformants expressing no receptor (lane 1), mRXRα (mouse RXRα receptor) (lane 3), hRARα (human RARα1 receptor) (lane 5), hRARα and mRXRα (lane 7), hRARα and mRXRαdn (mouse RXRαdn receptor) (lane 9). Specificity of binding was verified by supershifting retarded complexes with the RARα-specific monoclonal antibody Ab9a (Gaub, M. P. et al., *Exp. Cell Res.* 201:8:335–346 (1992)). Lanes 2, 4, 6, 8 and 10 contain identical samples as lanes 1, 3, 5, 7 and 9 respectively, but the samples were incubated with antibody immediately before electrophoresis. Arrows indicate the specific and supershifted complexes.

FIGS. 13A, B, and C. Direct Repeats of a Half Site Motif with Different Spacings and an Inverted Repeat of the Same Sequence with No Spacing, Function as RAREs in Yeast.

Figure 13B:
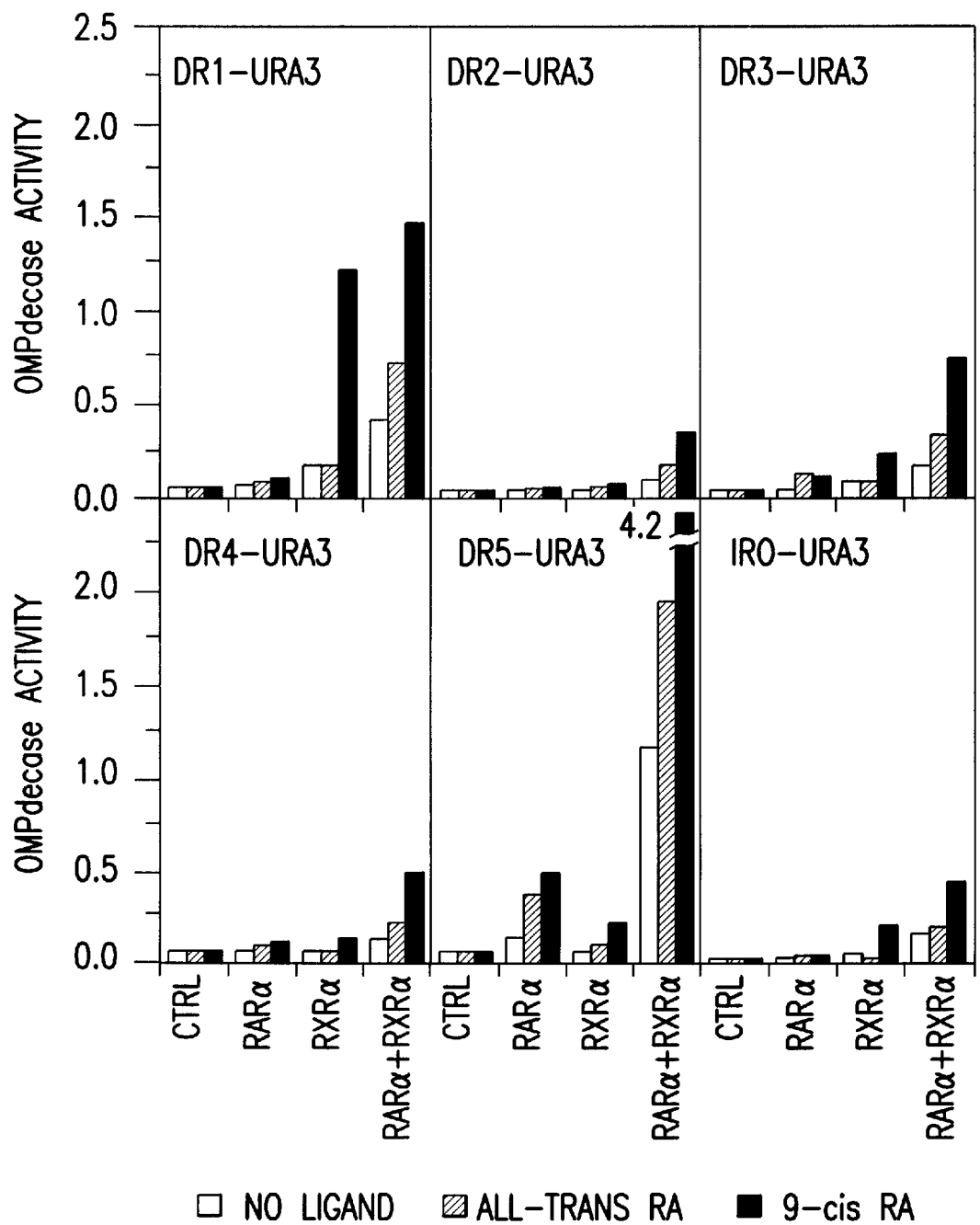
Figure 13C:
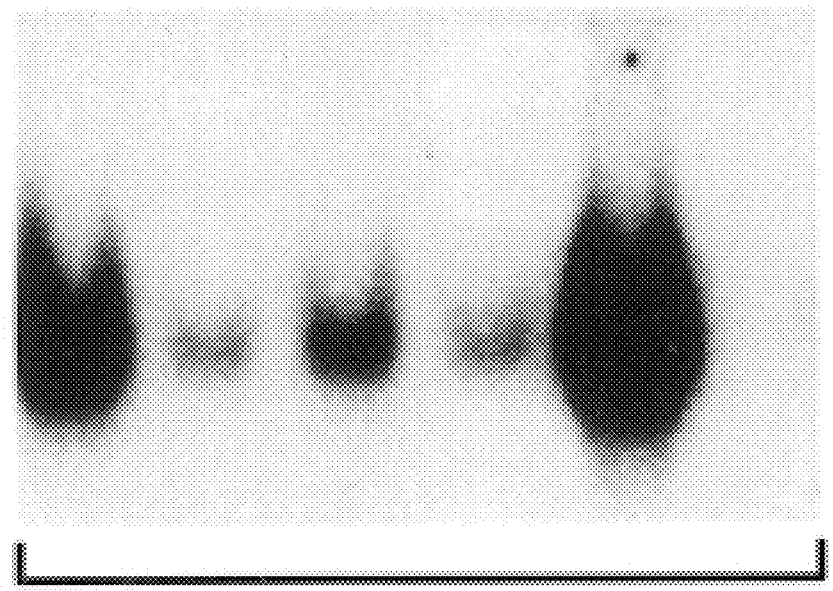

FIG. 13A, Sequences of the response elements used in this study consisting of a direct repeat of a hexamer sequence spaced by one to five base pairs (DR1–DR5), or an inverted repeat of the same hexamer with no spacing (IR0). The hexamer repeats are indicated by arrows and the spacer sequences are presented in lower case. FIG. 13B, Transactivation of URA3 reporter genes containing the different elements by homodimers and heterodimers of RARα and RXRα. The sequences represented in FIG. 13A were cloned into the promoter of a URA3 reporter gene carried on a centromeric plasmid to generate the DRn-URA3 reporter series and IR0-URA3. The reporters were introduced into a yeast strain containing multicopy vectors expressing RARα, RXRα or no receptor. Reporter activities in the presence or absence of ligand (500 nM) were determined by measuring the OMPdecase activity (Loison, G. et al., *Yeast* 5:497–507 (1989)). "Control" indicates the basal reporter activity in the absence of receptors (using "empty" expression vectors), and the experiments using only one receptor were performed in the presence of the corresponding "empty" vector. The white, hatched and black columns indicate the reporter activity in the presence of no ligand, all-trans RA and 9-cis RA, respectively. The reporter activities are given as units of OMPdecase activity per minute per mg protein, and the values represent the average of at least 2 experiments using at least 2 different clones per experiment. Deviation of values was less than 10%. FIG. 13C, Gel retardation assays using radiolabelled probes (containing the sequences described in 13A) and cell-free extracts from yeast coexpressing RARα and RXRα were performed as described previously (Heery, D. M. et al., *Proc. Natl. Acad. Sci. USA* 90:4281–4285 (1993)). Similar amounts of each probe (50, 000 cpm) were used in the assays.

Figure 14A:
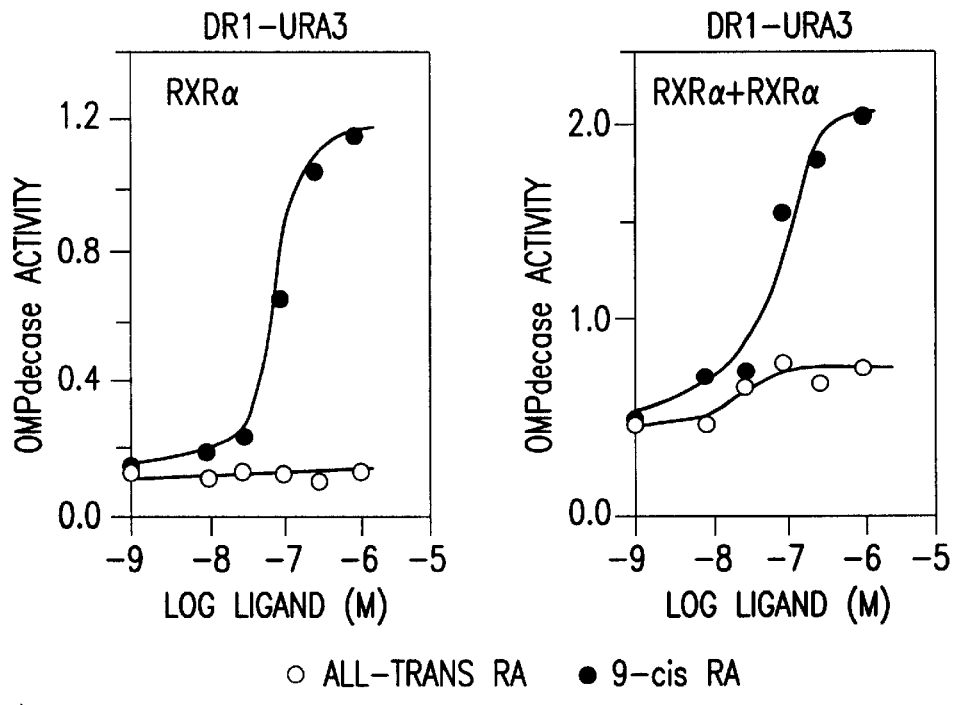

FIGS. 14A and B. Transactivation of the DR1-URA3 Reporter Gene by RXRα and RARα/RXRα Heterodimers, Synergistic activation of the CRBPII RXRE-URA3 by RXRα, and Effect of Deletions in RXRα on Reporter Activation.

Figure 14B:
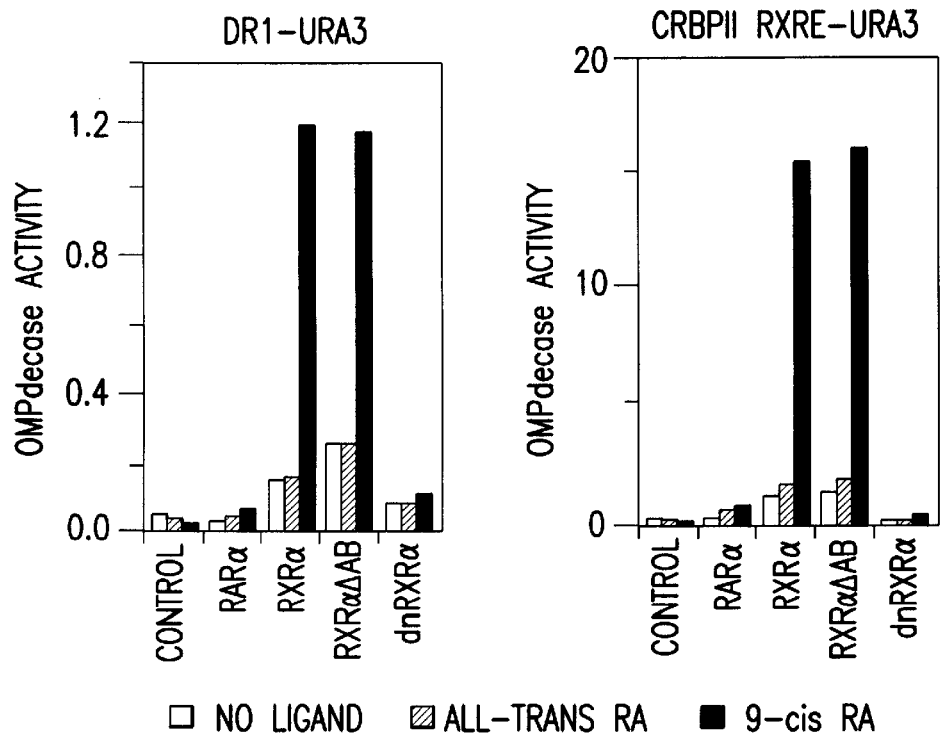

FIG. 14A, Ligand dose responses of DR1 reporter activity in the presence of RXRα and RARα/RXRα heterodimers. Activation of the DR1-URA3 reporter measured as OMPdecase activities in cell-free extracts of yeast expressing RXRα, or RARα and RXRα together, grown in the presence of all-trans RA (empty circles) and 9-cis RA (filled circles) at the indicated concentrations, as described previously (Heery, D. M. et al., *Proc. Natl. Acad. Sci. USA* 90:4281–4285 (1993)). FIG. 14B, Activation of DR1-URA3 and CRBPII RXRE-URA3 reporters in yeast expressing RARα, RXRα, RXRαΔB and dnRXRα or no receptor (control) in the presence or absence of ligand.

DETAILED DESCRIPTION OF THE INVENTION

The present invention is based in part on the isolation of a DNA sequence encoding members of the RXR receptor family.

The present invention is additionally based on the novel observation that three types of nuclear receptors, RAR, RXR and TR, can form heterodimers at physiological conditions. The heterodimers thus formed are able to bind to a RE with a much greater efficiency than the respective homodimers.

Based on these observations, the present invention provides previously unknown DNA sequences as well as heterodimeric proteins.

The present invention discloses DNA sequences which encode 1 isoform of mRXR-β (Sequence ID No. 1), 1 isoform of hRXR-β (Sequence ID No. 3), 1 isoform of mRXR-α (Sequence ID No. 5), and 1 isoform of mRXR-γ (Sequence ID No. 7). Using these sequences, or fragments thereof, as a probe, in conjunction with procedures known in the art, such as anchored PCR or blotting, it is now possible to isolate DNA sequences encoding homologous RXR receptors from other organisms, as well as isolating other subtypes of RXR, and other isotypes of the various subtypes of RXR.

As used herein, a "subtype" of RXR is identified by the presence of a subtype specific sequence which occurs within the A, B and/or D regions of the receptor. All isotypes from a given organism of a specific RXR family, for example all isoforms of human RXR-β, possess a conserved sequence which defines the subtype within these regions.

As used herein, an "isoform" of a particular subtype of RXR receptor is identified by sequence heterogeneity which is present in the A region of the RXR receptor. Various isoforms of a RXR receptor from a given organism will possess differing A region sequences.

For example, one skilled in the art can use: the A, B, and/or D region of Sequence ID No. 10, which encodes mouse RXR-γ specific regions of RXR, to isolate monkey RXR-γ sequences, or the B and/or D regions of this sequence to isolate other isoforms of mouse (or any other organism) RXR-γ.

The present invention further includes cells or organisms transformed with the above sequences. One skilled in the art can readily transform prokaryotes, such as *E. coli* and *B. subtilis,* as well as eukaryotes, such as human cells, insect cells and yeast with the above sequences.

The present invention additionally discloses heterodimeric proteins comprised of two non-identical subunits. One of the subunits is either a RAR or TR, and the other subunit is a RXR.

The heterodimeric proteins of the present invention include, but are not limited to, proteins wherein the first subunit is a RAR selected from the group consisting of the isotypes of the RAR-α, RAR-β, RAR-γ, TR-α or TR-62 receptor families, and the second subunit is a RXR selected from the group consisting of the isotypes of the RXRα, RXR-β, or RXR-γ receptor families.

The heterodimers of the present invention include, but are not limited to, proteins comprised of one subunit selected from the group consisting of: RAR-α1, RAR-α2, RAR-α3, RAR-α4, RAR-α5, RAR-α6, RAR-α7, RAR-β1, RAR-β2, RAR-β3, RAR-β4, RAR-γ1, RAR-γ2, RAR-γ3, RAR-γ4, RAR-γ5, RAR-γ6, RAR-γ7, TR-α1, TR-α2, TR-β1, TR-β2; and the other subunit being selected from the group consisting of mRXR-α (Sequence ID No. 9), hRXR-β (Sequence ID No. 4), mRXR-β (Sequence ID No. 2), or mRXR-γ (Sequence ID No. 8).

The present invention further provides highly purified subtypes and isoforms of RXR. Such purified RXR can exist as a monomer or a homodimer. As used herein, a protein is said to be highly purified if the protein possesses a specific activity that is greater than that found in whole cell extracts (WCE) containing the protein. For example, the specific activity commonly observed with WCE of HeLa cells is 156 cpm/ug (see Examples for assay conditions). The highly purified forms of RXR have a specific activity from about 1461 to 7,750,000 cpm/ug. Examples of the amino acid sequences of various highly purified RXR's of the present invention are depicted in Sequence ID No. 2 (mRXR-β), Sequence ID No. 4 (hRXR-β), Sequence ID No. 6 (mRXR-α), and Sequence ID No. 8 (mRXR-γ).

Any eukaryotic organism can be used as a source for the dimeric subunits, or the genes encoding same, as long as the source organism naturally contains such a subunit. As used herein, "source organism" refers to the original organism from which the amino acid or DNA sequence of the subunit is derived, regardless of the organism the subunit is expressed in or ultimately isolated from. For example, a human is said to be the "source organism" of RAR-α1 expressed in yeast as long as the amino acid sequence is that of human RAR-α1. The most preferred source organisms are human, mouse, and chicken.

A variety of methodologies known in the art can be utilized to obtain the subunits of the dimeric proteins of the present invention. In one embodiment, the subunits are purified from tissues or cells which naturally produce the given subunit. One skilled in the art can readily follow known methods for isolating proteins in order to obtain the desired subunit. These include, but are not limited to, immunochromotography, HPLC, size-exclusion chromatography, ion-exchange chromatography, and affinity chromatography.

The present invention further provides methods of purifying subtypes and isoforms of RXR. In detail, RXR's can be purified by:

a) contacting a sample containing a RXR protein with a DEAE chromatography column in the presence of a buffer containing from about 50 mM KCl;

b) retrieving the RXR in the flow through fraction from the column;

c) contacting the flow through fraction (b) with a HEP-UG column;

d) eluting the RXR from the column using from about 290 mM KCl;

e) contacting the KCl eluted RXR (d) with a phenyl-5PW column;

f) eluting the RXR from the column using from about 250 mM ammonium sulfate;

g) contacting the ammonium sulfate eluted RXR (f) with a HEP-TSK column;

h) eluting the RXR from the column using from about 250 mM KCl;

i) contacting the KCl eluted RXR (h) with a HAP-TSK column; and j) eluting the RXR from the column using from about 150 mM potassium phosphate.

The RXR's obtained by the above method can be either monomeric or dimeric. One skilled in the art can readily adapt the above purification scheme to delete some or incorporate other purification steps.

In another embodiment, the subunits are purified from cells which have been altered to express the desired subunit. As used herein, a cell is said to be "altered to express a desired subunit" when the cell, through genetic manipulation, is made to produce a protein which it normally does not produce, or which the cell normally produces at low levels. One skilled in the art can readily adapt procedures for introducing and expressing either genomic or cDNA sequences into either eukaryotic or prokaryotic cells, in order to generate a cell which produces a desired subunit.

There are a variety of source organisms for DNA encoding the desired subunit, including those subunits whose DNA sequence have been identified, such as the sequences found in Ruberte et al., *Development* 111:45–60 (1991), Chambon et al., *Seminars in Dev. Biol.* 2:153–159 (1991), Koelle et al., *Cell* 67:59–77 (1991), Mangelsdorf et al., *Nature* 345:224–229 (1990), Hamada et al., *Proc. Natl. Acad. Sci. USA* 86:8289–8293 (1989), Oro et al., *Nature* 347:298–301 (1990).

Alternatively, since probes are available which are capable of hybridizing to the various distinct subtypes and isoforms of RAR, RXR, and TR, DNA sequences encoding the desired subunits can be obtained by routine hybridization and selection from any host which possesses these receptors.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal the initiation of RXR synthesis. Such regions will normally include those 5'-non-coding sequences involved with initiation of transcription and translation, such as the TATA box, capping sequence, CAAT sequence, and the like.

If desired, the non-coding region 3' to the gene sequence encoding RXR may be obtained by the above-described methods. This region may be retained for its transcriptional termination regulatory sequences, such as termination and polyadenylation. Thus, by retaining the 3'-region naturally contiguous to the DNA sequence encoding RXR, the transcriptional termination signals may be provided. Where the transcriptional termination signals are not satisfactorily functional in the expression host cell, then a 3' region functional in the host cell may be substituted.

Two DNA sequences (such as a promoter region sequence and the RXR encoding sequence) are said to be operably linked if the nature of the linkage between the two DNA sequences does not (1) result in the introduction of a frame-shift mutation, (2) interfere with the ability of the promoter region sequence to direct the transcription of the RXR gene sequence, or (3) interfere with the ability of the RXR gene sequence to be transcribed by the promoter region sequence. Thus, a promoter region would be operably linked to a DNA sequence if the promoter were capable of effecting transcription of that DNA sequence.

Thus, to express the RXR, transcriptional and translational signals recognized by an appropriate host are necessary.

The present invention encompasses the expression of the RXR proteins (or a functional derivative thereof) and the dimeric proteins of the present invention in either prokaryotic or eukaryotic cells. Preferred prokaryotic hosts include bacteria such as *E. coli,* Bacillus, Streptomyces, Pseudomonas, Salmonella, Serratia, etc. The most preferred prokaryotic host is *E. coli.* Bacterial hosts of particular interest include *E. coli* K12 strain 294 (ATCC 31446), *E. coli* X1776 (ATCC 31537), *E. coli* W3110 (F$^-$, lambda$^-$, prototrophic (ATCC 27325)), and other enterobacterium such as *Salmonella typhimurium* or *Serratia marcescens,* and various Pseudomonas species. Under such conditions, the RXR will not be glycosylated. The procaryotic host must be compatible with the replicon and control sequences in the expression plasmid.

To express RXR (or a functional derivative thereof) in a prokaryotic cell (such as, for example, *E. coli, B. subtilis,* Pseudomonas, Streptomyces, etc.), it is necessary to operably link the RXR coding sequence to a functional prokaryotic promoter. Such promoters may be either constitutive or, more preferably, regulatable (i e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, etc. Examples of inducible prokaryotic promoters include the major right and left promoters of bacteriophage λ ($P_L$ and $P_R$), the trp, recA, lacZ, lac1, and gal promoters of *E. coli*, the α-amylase (Ulmanen, I. et al., *J. Bacteriol.* 162:176–182 (1985)) and the ç-28-specific promoters of *B. subtilis* (Gilman, M. Z. et al., *Gene sequence* 32:11–20 (1984)), the promoters of the bacteriophages of Bacillus (Gryczan, T. J., In: *The Molecular Biology of the Bacilli,* Academic Press, Inc., NY (1982)), and Streptomyces promoters (Ward, J. M. et al., *Mol. Gen. Genet.* 203:468–478 (1986)).

Prokaryotic promoters are reviewed by Glick, B. R., (*J. Ind. Microbiol.* 1:277–282 (1987)); Cenatiempo, Y. (*Biochimie* 68:505–516 (1986)); and Gottesman, S. (*Ann. Rev. Genet.* 18:415–442 (1984)).

Proper expression in a prokaryotic cell also requires the presence of a ribosome binding site upstream of the gene sequence-encoding sequence. Such ribosome binding sites are disclosed, for example, by Gold, L. et al. (*Ann. Rev. Microbiol.* 35:365–404 (1981)).

Preferred eukaryotic hosts include yeast, fungi, insect cells, mammalian cells either in vivo, or in tissue culture. Mammalian cells which may be useful as hosts include HeLa cells, cells of fibroblast origin such as VERO or CHO-K1, or cells of lymphoid origin, such as the hybridoma SP2/0-AG14 or the myeloma P3x63Sg8, and their derivatives. Preferred mammalian host cells include SP2/0 and J558L, as well as neuroblastoma cell lines such as IMR 332 that may provide better capacities for correct post-translational processing.

For a mammalian host, several possible vector systems are available for the expression of the RXR proteins or the dimers herein described. A wide variety of transcriptional and translational regulatory sequences may be employed, depending upon the nature of the host. The transcriptional and translational regulatory signals may be derived from viral sources, such as adenovirus, bovine papilloma virus, Simian virus, or the like, where the regulatory signals are associated with a particular gene sequence which has a high level of expression. Alternatively, promoters from mammalian expression products, such as actin, collagen, myosin, etc., may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides).

Any of a series of yeast gene sequence expression systems incorporating promoter and termination elements from the actively expressed gene sequences coding for glycolytic enzymes produced in large quantities when yeast are grown in media rich in glucose can be utilized. Known glycolytic gene sequences can also provide very efficient transcriptional control signals. For example, the promoter and terminator signals of the phosphoglycerate kinase gene sequence can be utilized. Yeast is an especially preferred host since yeast cells do not contain RA receptors.

Another preferred host is insect cells, for example the Drosophila larvae. Using insect cells as hosts, the Drosophila alcohol dehydrogenase promoter can be used (Rubin, G. M., *Science* 240:1453–1459 (1988)). Alternatively, baculovirus vectors can be engineered to express large amounts of the RXR in insects cells (Jasny, B. R., *Science* 238:1653 (1987); Miller, D. W. et al., in *Genetic Engineering* (1986), Setlow, J. K. et al., eds., *Plenum,* Vol. 8, pp. 277–297).

As discussed above, expression of RXR in eukaryotic hosts requires the use of eukaryotic regulatory regions. Such regions will, in general, include a promoter region sufficient to direct the initiation of RNA synthesis. Preferred eukaryotic promoters include the promoter of the mouse metallothionein I gene sequence (Hamer, D. et al., *J. Mol. Appl. Gen.* 1:273–288 (1982)); the TK promoter of Herpes virus (McKnight, S., *Cell* 31:355–365 (1982)); the SV40 early promoter (Benoist, C. et al., *Nature* (London) 290:304–310 (1981)); the yeast gal4 gene sequence promoter (Johnston, S. A. et al., *Proc. Natl. Acad. Sci.* (*USA*) 79:6971–6975 (1982); Silver, P. A. et al., *Proc. Natl. Acad. Sci.* (*USA*) 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes the RXR (or a functional derivative thereof) does not contain any intervening codons which are capable of encoding a methionine (i.e., AUG). The presence of such codons results either in a formation of a fusion protein (if the AUG codon is in the same reading frame as the RXR coding sequence) or a frame-shift mutation (if the AUG codon is not in the same reading frame as the RXR coding sequence).

The RXR coding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the RXR may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain protein-binding mRNA. These elements may include splice signals, as well as transcription promoters, enhancers, and termination signals. cDNA expression vectors incorporating such elements include those described by Okayama, H., *Molec. Cell. Biol.* 3:280 (1983).

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, πVX. Such plasmids are, for example, disclosed by Maniatis, T. et al. (In: *Molecular Cloning, A Laboratory Manual*, Cold Spring Harbor Press, Cold Spring Harbor, N.Y. (1982)). Bacillus plasmids include pC194, pC221, pT127, etc. Such plasmids are disclosed by Gryczan, T. (In: *The Molecular Biology of the Bacilli*, Academic Press, NY (1982), pp. 307–329). Suitable Streptomyces plasmids include pIJ101 (Kendall, K. J. et al., *J. Bacteriol.* 169:4177–4183 (1987)), and streptomyces bacteriophages such as φC31 (Chater, K. F. et al., In: *Sixth International Symposium on Actinomycetales Biology*, Akademiai Kaido, Budapest, Hungary (1986), pp. 45–54). Pseudomonas plasmids are reviewed by John, J. F. et al. (*Rev. Infect. Dis.* 8:693–704 (1986)), and Izaki, K. (*Jpn. J. Bacteriol.* 33:729–742 (1978)).

Preferred eukaryotic plasmids include BPV, vaccinia, SV40, 2-micron circle, etc., or their derivatives. Such plasmids are well known in the art (Botstein, D. et al., *Miami Wntr. Symp.* 19:265–274 (1982); Broach, J. R., In: *The Molecular Biology of the Yeast Saccharomyces:* Life Cycle and Inheritance, Cold Spring Harbor Laboratory, Cold Spring Harbor, N.Y., p. 445–470 (1981); Broach, J. R., *Cell* 28:203–204 (1982); Bollon, D. P. et al., *J. Clin. Hematol. Oncol.* 10:39–48 (1980); Maniatis, T., In: *Cell Biology: A Comprehensive Treatise*, Vol. 3, Gene sequence Expression, Academic Press, NY, pp. 563–608 (1980)).

Once the vector or DNA sequence containing the construct(s) has been prepared for expression, the DNA construct(s) may be introduced into an appropriate host cell by any of a variety of suitable means: transformation, transfection, conjugation, protoplast fusion, electroporation, calcium phosphate-precipitation, direct microinjection, etc. After the introduction of the vector, recipient cells are grown in a selective medium, which selects for the growth of vector-containing cells. Expression of the cloned gene sequence(s) results in the production of RXR, or fragments thereof. This can take place in the transformed cells as such, or following the induction of these cells to differentiate (for example, by administration of bromodeoxyuracil to neuroblastoma cells or the like).

A cell can be altered to express either a single subunit of the dimer, or altered to express both subunits of the dimer. When the cell is altered to express a single subunit, the heterodimers of the present invention are generated by mixing the individual subunits which have isolated from two different transformed hosts while the homodimers are generated by incubating the monomeric subunit under conditions which promote dimerization.

A variety of incubation conditions can be used to form the dimers of the present invention. The most preferred conditions are those which mimic physiological conditions. In the examples provided below, heterodimers were formed in 150 mM KCL.

When the cells are altered to express both subunits, the dimer can be purified from the single host.

The dimeric proteins of the present invention can be used in a variety of procedures and methods, such as for the generation of antibodies, for use in identifying pharmaceutical compositions, and for studying DNA/protein interaction.

In one embodiment, the dimer is used as an immunogen to generate an antibody which is capable of binding to the dimer. In a further aspect of this embodiment, the antibody is additionally incapable of binding to the individual subunit even though it binds to the dimer.

Any of the dimers of the present invention can be used to produce antibodies or hybridomas. One skilled in the art will recognize that if an antibody is desired that will bind to hRAR-α/hRXR-α, such a dimer would be generated as described above and used as an immunogen. The resulting antibodies are then screened for the ability to bind the dimer. Additionally, the antibody can be screened for it's inability to bind the individual subunits.

The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting.

The invention also provides hybridomas which are capable of producing the above-described antibodies. A hybridoma is an immortalized cell line which is capable of secreting a specific monoclonal antibody.

In general, techniques for preparing monoclonal antibodies and hybridomas are well known in the art (Campbell, A. M., "*Monoclonal Antibody Technology: Laboratory Techniques in Biochemistry and Molecular Biology*," Elsevier Science Publishers, Amsterdam, The Netherlands (1984); St. Groth et al., *J. Immunol. Methods* 35:1–21 (1980)).

Any animal (mouse, rabbit, etc.) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)).

Hybridomas secreting the desired antibodies are cloned and the class and subclass is determined using procedures known in the art (Campbell, A. M., *Monoclonal Antibody Technology: Laboratory Techniques in Biochemistry and Molecular Biology*, Elsevier Science Publishers, Amsterdam, The Netherlands (1984)).

For polyclonal antibodies, antibody containing antisera is isolated from the immunized animal and is screened for the presence of antibodies with the desired specificity using one of the above-described procedures.

In another embodiment of the present invention, the above-described antibodies are detectably labelled. Antibodies can be detectably labelled through the use of radioisotopes, affinity labels (such as biotin, avidin, etc.), enzymatic labels (such as horse radish peroxidase, alkaline phosphatase, etc.) fluorescent labels (such as FITC or rhodamine, etc.), paramagnetic atoms, etc. Procedures for accomplishing such labelling are well-known in the art, for example see (Sternberger, L. A. et al., *J. Histochem. Cytochem.* 18:315 (1970); Bayer, E. A. et al., *Meth. Enzym.* 62:308 (1979); Engval, E. et al., *Immunol.* 109:129 (1972); Goding, J. W. *J. Immunol. Meth.* 13:215 (1976)). The labeled antibodies of the present invention can be used for in vitro, in vivo, and in situ assays to identify cells or tissues which express a specific heterodimer.

In another embodiment of the present invention the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir, D. M. et al., "*Handbook of Experimental Immunology*" 4th Ed., Blackwell Scientific Publications, Oxford, England, Chapter 10 (1986); Jacoby, W. D. et al., *Meth. Enzym.* 34 Academic Press, N.Y. (1974)). The immobilized antibodies of the present invention can be used for in vitro, in vivo, and in situ assays as well as in immunochromotography.

In another embodiment of the present invention, methods of determining the expression of a specific dimer in a test sample are presented.

In detail, the methods comprise incubating a test sample with one or more of the antibodies of the present invention and assaying whether the antibody binds to the test sample.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, T. "*An Introduction to Radioimmunoassay and Related Techniques*" Elsevier Science Publishers, Amsterdam, The Netherlands (1986); Bullock, G. R. et al., "*Techniques in Immunocytochemistry,*" Academic Press, Orlando, Fla. Vol. 1 (1982), Vol. 2 (1983), Vol. 3 (1985); Tijssen, P., "*Practice and Theory of Enzyme Immunoassays: Laboratory Techniques in Biochemistry and Molecular Biology,*" Elsevier Science Publishers, Amsterdam, The Netherlands (1985).

The test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

In another embodiment of the present invention, methods are provided for identifying agents which are capable of binding to one of the dimeric proteins of the present invention.

In detail, said method comprises:
(a) contacting an agent with one or more of the dimeric proteins of the present invention; and
(b) determining whether the agent binds to the dimer.

In performing such an assay, one skilled in the art will be able to determine which isotype or subtype of a specific nuclear receptor an agent binds to, and hence determine what specific receptor(s) are utilized by the compound.

The agents screened in the above assay can be, but are not limited to, peptides, carbohydrates, and vitamin derivatives. The agent can be selected, and screened at random, rationally selected or rationally designed using protein modeling techniques.

For random screening, agents such as peptides, carbohydrates, or derivatives of RA, are selected at random and are assayed for there ability to bind to one of the heterodimers of the present invention using either direct or indirect methods.

Alternatively, agents may be rationally selected. As used herein, an agent is said to be "rationally selected" when the agent is chosen based on the physical structure of a known ligand of the heterodimer. For example, assaying compounds possessing a retinol like structure would be considered a rational selection since retinol like compounds will bind to a variety of the heterodimers.

Since highly purified dimers are now available, X-ray crystallography and NMR-imaging techniques can be used to identify the structure of the ligand binding site present on the heterodimer. Utilizing such information, computer modeling systems are now available that allows one to "rationally design" an agent capable of binding to a defined structure (Hodgson, *Biotechnology* 8:1245–1247 (1990)), Hodgson, *Biotechnology* 9:609–613 (1991)).

As used herein, an agent is said to be "rationally designed" if it is selected based on a computer model of the ligand binding site of the heterodimer.

In one aspect of the above-described binding assay, the assay is performed in the presence of a segment of DNA which has been identified as a RE. In this fashion agents can be identified which are capable of either stimulating or inhibiting the binding of the dimer to the RE. Any length of DNA can be used in such an assay as long as it contains at least one RE sequence.

In another embodiment, the above assay is performed in the absence of a RE. In this fashion, agents can be identified which bind to the dimer independently of DNA binding.

Further, the above assay can be modified so that it is capable of identifying agents which activated transcription of DNA sequences controlled by a RE.

In detail a cell or organism, such as a yeast cell, is altered using routine methods such that it expresses one or more of the RAR/RXR hetero- or homodimers of the present invention.

In one application, the cell is further altered to contain a RE, such as DR1, operably linked to a reporter sequence, such as luciferase, beta galactosidase, chloramphenicol acyltransferase or a selectable marker such as URA3. An agent is then incubated with the cell or organism and the expression of the reporter sequence or selectable marker activity is then assayed. By utilizing the above procedure, agents capable of stimulating RAR/RXR/RE dependent transcription or inhibiting ligand-induced transcription can be identified.

The present invention further discloses that RAR/RXR heterodimers, and RAR or RXR homodimers when expressed in yeast cells, are capable of transactivating the transcription of a sequence operably linked to an RARE. As described in Example 2, yeast cells do not naturally contain RAR and RXR receptors. Further, unlike most other eukaryotic organisms, yeasts, in general, do not appear to contain enzymes which interconvert different classes of retinoids. For example mammals contain enzymes (RA isomerase activities) which convert all-trans retinoic acid to 9-cis retinoic acid whereas yeast does not. In particular, yeast cells containing a chimeric RXR (RXR-ER.CAS) activate transcription in the presence of 9cis-RA, but not all-trans RA (Heery et al., *PNAS* 90:4281–4285 (1993)), and may be used to clone the mammalian all-trans-9cis isomerase by complementation with cDNA expression libraries made from mammalian cell-derived RNA. Other enzymes involved in RA metabolism might be similarly cloned by complementation, using positive and negative selection techniques. Therefore, yeast cells such as *Saccharomyces cerevisiae* are an especially preferred organism for expressing RAR and RXR receptor proteins and for using such an expression system to further study and identify agents which modulate RAR/RXR/RARE dependent transcription.

In general, a modified yeast cell is generated for use in studying transactivation by modifying the yeast cell, using routine genetic manipulations, such that it contains, and is capable of expressing, one or more subtypes or isoforms of RAR and/or RXR receptors, for example a cell is modified such that it expresses RARα1 and RXRα (see Example 2) or RXR (Example 3). The cell is then further modified so that a gene encoding a selectable marker activity, for example URA3 if the original yeast host is ura3, or a gene encoding an assayable marker activity, for example beta-galactosidase, is placed under the control of a RARE, for example a DR5 sequence.

Such a modified yeast cell is then used to identify agents which are capable of transactivating the particular RAR/RXR/RARE combination. In detail, when the above described modified yeast cell is incubated with an agent which is capable of binding to the RAR/RXR dimer, stimulating the dimer's ability to bind to and activate the transcription of sequences linked to the RARE (transactivation), the cell will be capable of growth in a media not containing uracil, or can be identified as expressing the marker activity. By generating a variety of modified yeast cells, each one expressing a different RAR/RXR heterodimer or RAR or RXR homodimer and each containing one or more selectable markers linked to various RAREs, dimer isoform and subtype specific as well as RARE specific activating agents can be identified.

In other applications, the yeast system described above and herein, can be further utilized to 1) identify RARE sequences, 2) identify antagonists and agonist of transcription which is controlled by RAR/RXR heterodimers or RAR or RXR homodimers, 3) identify and clone genes encoding enzymes capable of metabolising retinoids (i.e., enzymes with RA isomerase activity), and 4) to identify and clone genes encoding novel dimeric partners of RXRs by complementation with mammalian RNA-derived yeast expression vectors.

Specifically, to identify DNA sequences which act as an RARE, for example sequences such as DR1, DR2 and DR5, a yeast cell is modified as such that the cell expresses one or more RAR/RXR hetero- or homodimers. The cell is further modified such that the cell contains the DNA sequence which is to be tested. The sequence which is to be tested for RARE activity is placed 5' to a gene encoding selectable marker activity, for example, URA3 in a ura3 host cell, or a gene encoding an assayable marker activity. The cell is then incubated in the presence of an agent which is known to activate RAR/RXR, RAR or RXR dependent transactivation. Cells in which the DNA sequence placed upstream to the selectable marker contain an RARE activity will be capable of growing in a selection media devoid of uracil or will express the assayable activity encoded by the marker gene. Such a procedure can be utilized for screening randomly cloned DNA sequences, a shot-gun type approach, or can be used to test DNA sequences which are rationally designed based on the sequence of known RAREs.

To identify antagonists of a specific RAR/RXR hetero- or homodimer, a yeast cell is modified such that the cell expresses one or more RAR/RXR hetero- or homodimers. The cell is further modified such that the cell contains a RARE placed 5' to a lethal marker, the expression of such a marker leads to cell death. The modified yeast cell is then incubated in the presence of 2 agents, the first agent being a compound which is known to transactivate the specific RAR/RXR/RARE combination contained in the yeast cell, the second agent being the compound which is being tested for antagonistic activity. Agents which act as a antagonist will prevent the expression of the lethal gene.

To identify DNA sequences which encode enzymes capable of metabolising various retinoids, for example the enzyme responsible for isomerisation of all-trans retinoic acid to 9 cis-retinoic acid in a mammal, a yeast cell is modified such that it expresses one or more RAR/RXR hetero- or homodimers. The cell is further modified such that it contains a RARE placed 5' to a gene encoding a selectable marker activity, for example, URA3 in a ura3 host cell, or gene encoding an assayable marker activity. The cell is then used as a host for expressing cDNA's which have been isolated from a mammal (or other source) which is known or suspected of being capable of interconverting a specific class of retinoids, for example a human skin cDNA library.

After transformation with the cDNA library, the yeast cell is then incubated with an agent which does not transactivate the specific RAR/RXR/RARE combination contained within the cell unless the agent is first converted into an active form. Cells capable of growth in a selection media, or cells which express the assayable marker, are supposed to contain gene sequences encoding an enzyme which converts the retinoid into an active form. Alternatively, the cell can be incubated with a retinoid which is capable of transactivating the RAR/RXR/RARE combination contained in the cell but is incapable of transactivation once the agent has been converted into an inactive form.

The above procedure can be modified to use nuclear and/or cytosolic extracts from the altered cell containing the hetero- or homodimer, as opposed to using the intact cells. In such an application an extract of a cell expressing a RAR/RXR heterodimer, or a RAR or RXR homodimer, is mixed with an expression module containing an RARE operably linked to a reporter sequence. The extract/expression module is then incubated with an agent and the expression of the reporter sequence is assayed.

In another embodiment of the present invention, kits are provided which contain the necessary reagents to carry out the previously described assays.

Specifically, the invention provides a compartmentalized kit to receive, in close confinement, one or more containers which comprises: (a) a first container comprising one of the antibodies of the present invention, one or more of the dimers of the present invention, or one or more of the modified cells of the present invention; and (b) one or more other containers comprising one or more of the following: wash reagents, reagents capable of detecting presence of bound antibodies or heterodimers from the first container, RE sequences, or antagonist on agonists RAR/RXR/RARE transactivation.

In detail, a compartmentalized kit includes any kit in which reagents are contained in separate containers. Such containers include small glass containers, plastic containers or strips of plastic or paper. Such containers allow one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody.

Types of detection reagents include labelled secondary antibodies, or in the alternative, if the primary antibody is labelled, the chromophoric, enzymatic, or antibody binding reagents which are capable of reacting with the labelled antibody. One skilled in the art will readily recognize that the disclosed antibodies of the present invention can readily be incorporated into one of the established kit formats which are well known in the art.

The present invention further provides methods of identifying and isolating DNA sequences which bind to the dimers of the present invention. Specifically, the dimers of the present invention can be used to isolate or screen given sequences for the ability to be bound by the dimer or act as an RARE.

There are a variety of methods known in the art for isolating sequences which are bound by a protein. In one such method, the dimer is immobilized on a solid support and used as an affinity matrix to isolate sequences which bind to it (Arcangioli et al., *Eur. J. Biochem.* 179:3459–364 (1989)).

For example, a hRAR-α1/hRXR-β heterodimer, or a RXRα homodimer, is immobilized on sepharose and sheared human DNA (most preferably 20bp–2kb in length) is washed over the column. Sequences which bind to the dimer will stick to the column whereas sequences which don't will be removed in the washes. Additionally, the bound sequences can be amplified using PCR prior to cloning.

Alternatively, the dimeric protein can be used to screen a genomic library whose DNA has been immobilized on a solid support such as nitrocellulose. (Sharp et al., *Biochem. Biophys Acta* 1048:306–309 (1990); Walker et al., *Nuc. Acid. Res.* 18:1159–1166 (1990)).

The present invention further provides methods of regulating gene expression in a cell.

In detail, a cell can be altered such that it contains a DNA sequence operably linked to an RE. Additionally, the cell can be altered to express various subunits which form the dimeric proteins of the present invention. By selecting the appropriate subunit/RE combination, one skilled in the art can generate a cell which expresses a given sequence in response to a particular agent.

Having now been generally described in the invention, the agents and methods of obtaining same will be more readily understood through reference to the following examples which are provided by way of illustration, they are not intended to be limiting of the present invention unless specified.

EXAMPLE 1
Presence in HeLa and Insect Cells of Factors Required for Efficient RAR/RARE Complex Formation in vitro The requirement of cellular binding factors (RAR binding factors or RBFs) for efficient RAR/RARE formation was initially investigated with hRAR-γ produced by using several over-expression systems (similar results were obtained with hRAR-α and β, data not shown and see below). hRAR-γ was first over-expressed by infection of HeLa cells with recombinant vaccinia virus (rVV) harboring the cDNA-coding sequence of the receptor (Nicholson et al., *EMBO J.* 9:4443–4454 (1990)). The binding of hRAR-γ present in nuclear extracts (NE) of these cells to the RAR-β RARE (β-RARE, de Thé et al., *Nature* 343:177–180 (1990), see FIG. 4) was assessed by gel shift (FIG. 1A, lane 1, arrow), and its specificity was verified by using an anti-RAR-γ antibody in supershift experiments (Nicholson et al., *EMBO J.* 9:4443–4454 (1990); Smith et al., *EMBO J.* 10:2223–2230 (1991)), as well as by competition experiments employing wild type and mutated β-RAREs (Smith et al., *EMBO J.* 10:2223–2230 (1991)) (data not shown). Furthermore, no complex was formed with extracts of wild-type VV-infected cells (data not shown). Addition of increasing amounts of non-infected HeLa cell NE stimulated complex formation (FIG. 1A, lanes 2–4), suggesting the existence of a limiting factor which enhanced RAR binding.

Figure 1A:
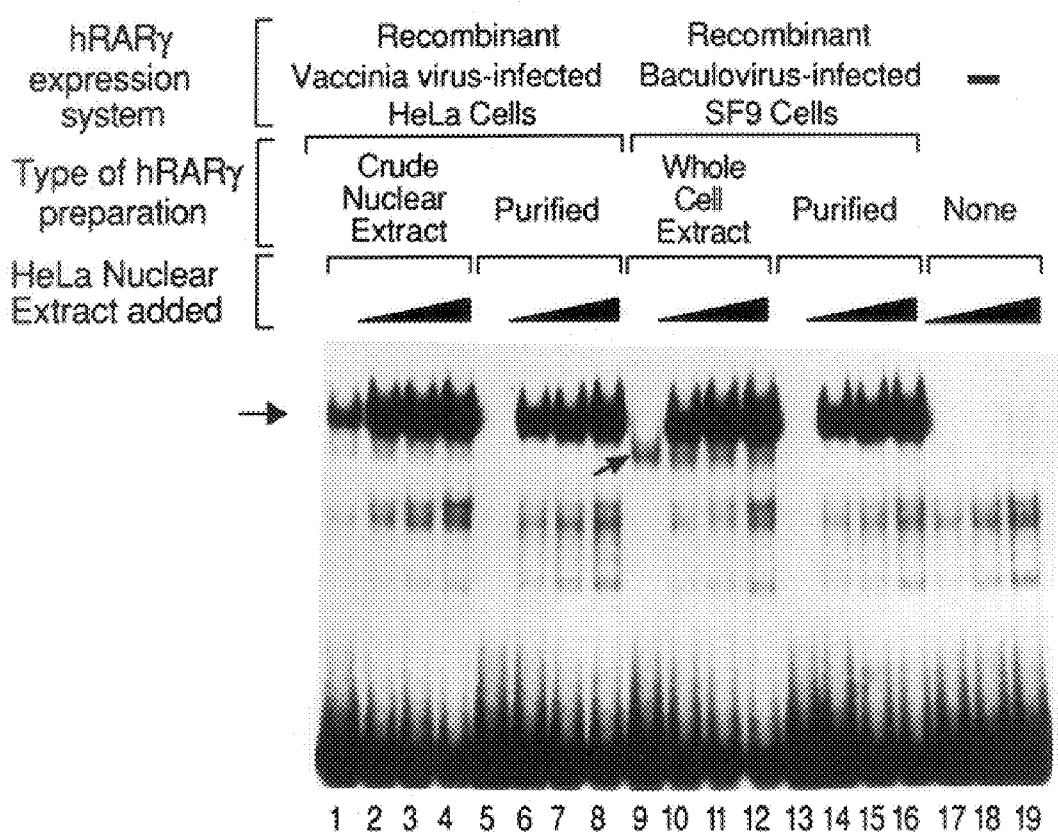
FIGS. 1A/B, C, D, and E. Dependence of hRAR-γ DNA binding on HeLa and insect cell RBF(s); Purification of a HeLa cell RBF FIGS. 1A and 1B. Gel retardation assays in which increasing amounts of HeLa NE (0, 1.5, 3 and 6 mg of protein) were added to incubations containing the β-RARE probe and crude (lanes 1–4) or purified (lanes 5–8) rVV-expressed hRAR-γ, crude (lanes 9–12) or purified (lanes 13–16) rBV-expressed hRAR-γ in-vitro translated receptor (lanes 20–23) and bacterially-expressed hRAR-γ (lanes 24–27). Arrows indicate positions of HeLa- and Sf9-cell specific complexes. The binding of two independent preparations of HeLa nuclear extract in the absence of hRAR-γ is shown in lanes 17–19 and 28–30.
Figure 1B:
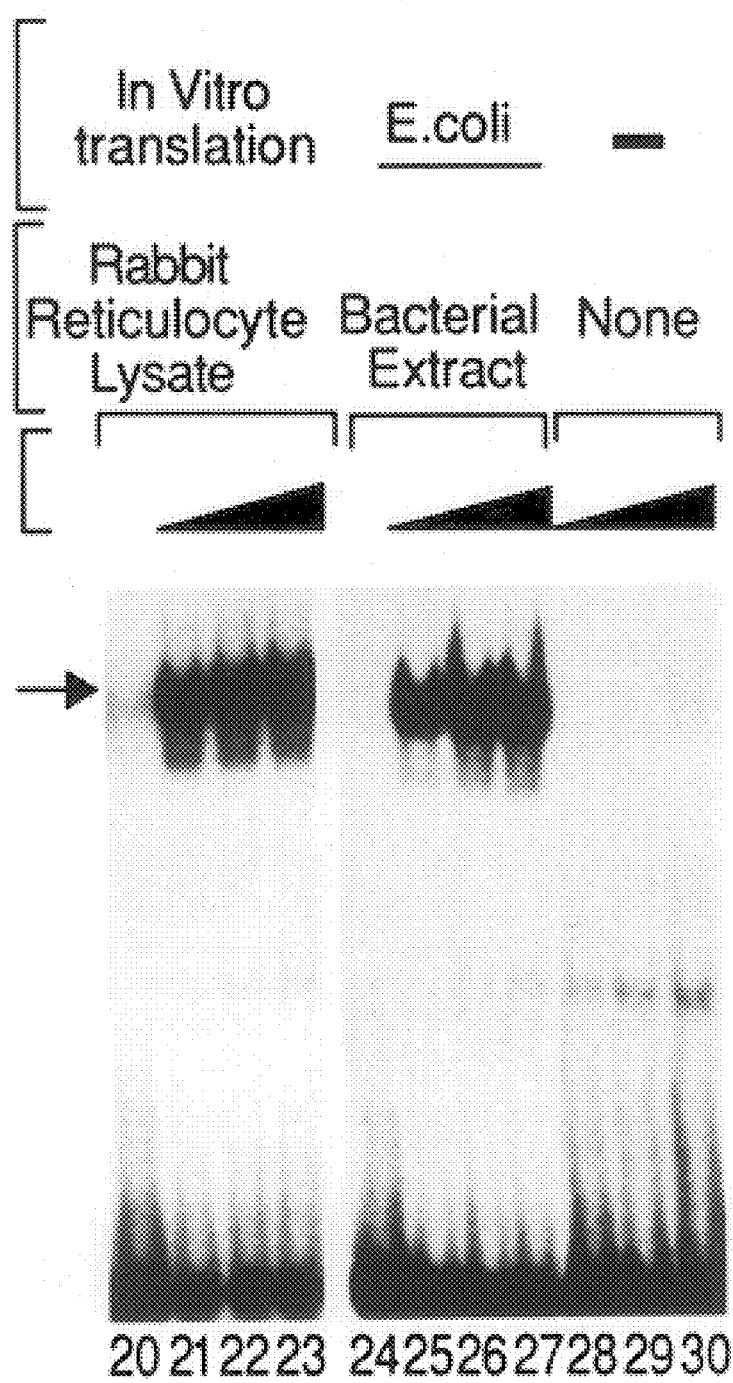
FIG. 1C. Gel retardation assays in which bacterially-expressed hRAR-γ (10 fmols) was incubated with extracts prepared from HeLa (3 µg of protein), Sf9 (5 µg) and Drosophilia S2 (5 µg) cells as indicated. Lanes 5–7 represent binding of these extracts in the absence of hRAR-γ.
FIG. 1D. Silver stained gel representing each step of HeLa cell RBF purification. The amounts of protein (in µg) loaded in each lane is: WCE, 1.5; DEAE FT, 1.1; HEP-UG, 2; Phenyl-5PW, 5; HEP-TSK, 1.3 and HAP-TSK, 0.05 (estimate). The migration of molecular weight standards (BioRad) is indicated.
FIG. 1E. Gel retardation assay representing each step of HeLa cell RBF purification. HeLa NE (4 µg of protein) was included as a positive control (lane 2). The amount of HeLa cell protein (in µg) used in each lane is: WCE, 10; DEAE FT, 0.5; HEP-UG, 0.18; Phenyl-5PW, 0.12; HEP-TSK, 0.03 and HAP-TSK 0.001 (estimate). Lanes contain the stated amounts of protein from each purification step and ~10 fmols of bacterially-expressed hRAR-γ where indicated.

Interestingly, under identical binding conditions, no complex was observed with purified rW-expressed receptor (FIG. 1A, lane 5), even though the amount of receptor protein used (as determined by Western blotting, data not shown) was the same as in the assay with crude extracts (lane 1). However, hRAR-γ binding was fully restored by addition of HeLa cell NE (FIG. 1A, lanes 6–8, compare with lanes 2–4), indicating that no intrinsic DNA binding capability of hRAR-γ was lost during receptor purification. Note that the formation of the specific complex was fully dependent on the presence of purified hRAR-γ (FIG. 1A, lanes 17–19 and 10, lanes 28–30). Crude preparations of hRAR-γ expressed in *E. coli* (FIG. 1B, lanes 24–27), as an ubiquitin fusion protein in yeast (data not shown), or hRAR-γ translated in a rabbit reticulocyte lysate in vitro (lanes 20–23) behaved similarly, in that specific complex formation was dependent upon addition of HeLa cell NE. In no case was the formation of the complex affected by the presence of RA. Addition of *E. coli*, non-yeast extracts, non-specific proteins (e.g. serum albumin), the estrogen receptor DNA binding stimulatory factor (Mukherjee et al., *Nucl. Acids Res.* 18:5713–5716 (1990)), or concentrations of DTT up to 50 mM (Abate et al., *Science* 249:1157–1161 (1990)) did not enhance hRAR-γ binding (data not shown).

Similar results were observed when the source of receptor was a baculovirus (rBV) expression system (FIG. 1A, lanes 9–12). However, a complex of higher electrophoretic mobility (relative to that seen with nuclear extracts prepared from rVV-infected HeLa cells) was observed using crude extracts of rBV-infected *Spodoptera frugiperda* Sf9 cells (FIG. 1A, compare lanes 1 and 9). This complex contained hRAR-γ as shown by antibody supershifting (data not shown). The Sf9 cell-specific complex was not observed using hRAR-γ purified from extracts of these cells (FIG. 1A, lane 13). However, the receptor/DNA complex of lower electrophoretic mobility could be formed by addition of HeLa cell NE (FIG. 1A, lanes 14–16). Similarly, addition of Sf9 cell extracts to hRAR-γ purified from rVV or rBV extracts reconstituted the Sf9-specific complex of higher electrophoretic mobility (data not shown). In contrast, Drosophila Schneider S2 cells contained a RBF which stimulated formation of RAR/β-RARE complexes that migrated reproducibly slower than those formed with either Sf9 or HeLa cell RBFs (FIG. 1C, compare lanes 2–4). Note that, in the absence of hRAR-γ, Sf9 or S2 cell proteins bound weakly, if at all, to the β-RARE (FIG. 1C, lanes 6 and 7, and data not shown).

We conclude from the above data that hRAR-γ does not bind efficiently on its own to the β-RARE, irrespective of the source of over-expressed receptor. It appears that efficient hRAR-γ binding to β-RARE requires the presence of factor (s) (RBFs) which are present in either HeLa or insect cells, but not in yeast and E. coli. Moreover, our data suggest that HeLa and insect cell RBFs are distinct from each other and bind to β-RARE, together with hRAR-γ, since the complexes formed in the presence of HeLa, Sf9 and S2 cell extracts have different electrophoretic mobilities (see FIG. 1A and 1C). Finally, these RBF activities were inactivated by heating (65° C. for 10 min) or trypsin treatment (data not shown), thus indicating that they were protein aceous.

HeLa Cell RBF is a Human RXR-β

Figure 1E:
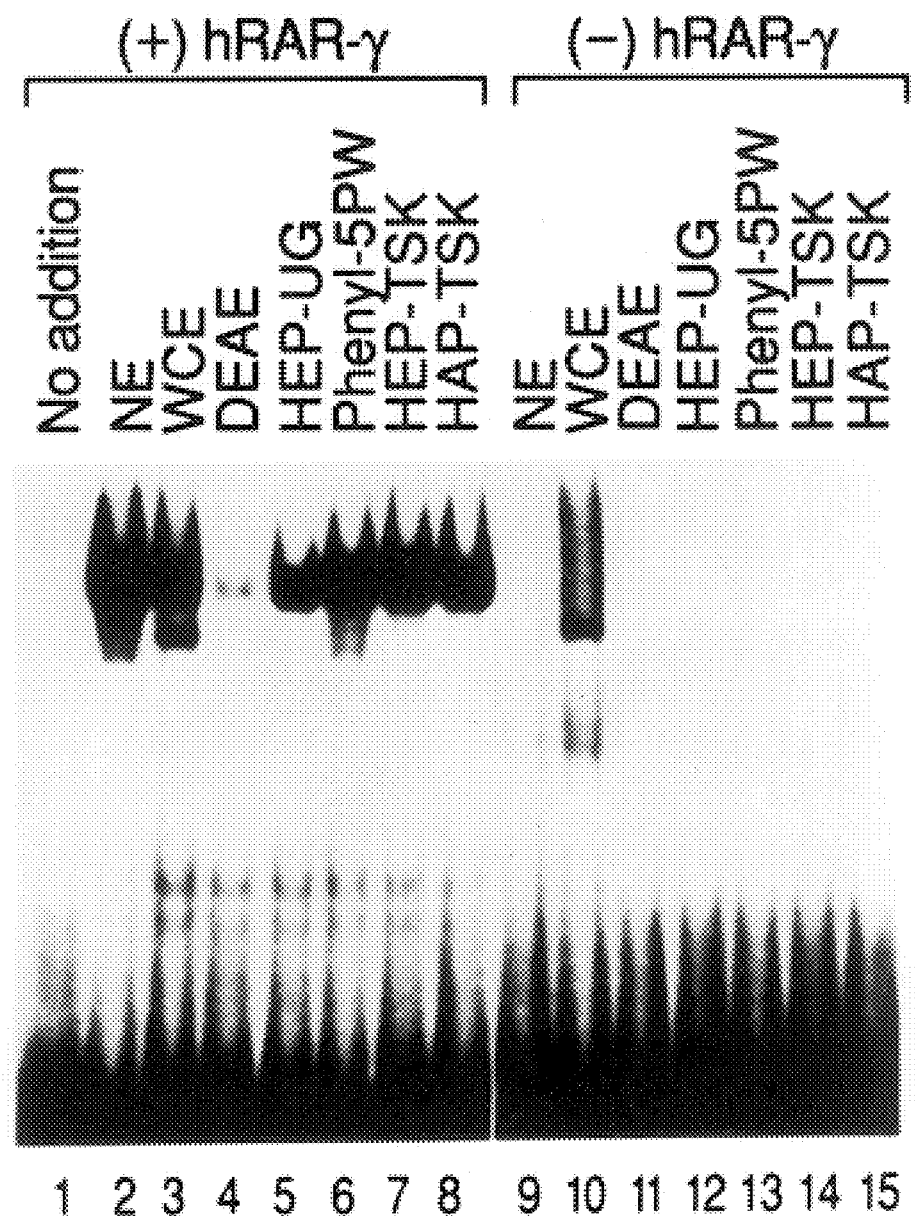

A fractionation of HeLa whole cell extract (WCE) was performed in an attempt to purify and clone the human RBF required for efficient RAR/RARE complex formation. Sequential chromatography on DEAE-BioGel A, Heparin-Ultrogel, Phenyl-SPW, Heparin-TSK and Hydroxylapatite-TSK columns yielded an apparently homogenous polypeptide of ~64 kDa (FIG. 1D), which strongly stimulated β-RARE binding by RAR-γ (FIG. 1E). The specific activity of hydroxylapatite column-purified RBF (FIG. 1D, lane 6) was approximately 49,000 fold greater than that of HeLa WCE (Table 1). The polypeptide of 64 kDa and the RBF activity precisely coeluted during the final three chromatography steps (data not shown), indicating that this polypeptide could correspond to HeLa cell RBF activity. Moreover, the purified RBF sedimented as a ~60 kDa species in a glycerol gradient (data not shown).

The sequences of seven peptides obtained from a tryptic digestion of the HeLa cell 64 kDa protein were determined and compared to a data base. All seven peptides (shaded in FIG. 2) were very similar to sequences deduced from the cDNA of the human retinoid X receptor-alpha (hRXR-α, Mangelsdorf et al., Nature 345:224–229 (1990)). Since we had cloned the cDNAs encoding three members of the murine RXR family, namely mRXR-α, mRXR-β and mRXr-γ (FIG. 2, and our unpublished results), we looked for sequence similarities among the family of RXRs in order to identify which RXR subtype may correspond to HeLa cell RBF. Only one peptide (p28, see FIG. 2) allowed complete discrimination between the members of the RXR family and the sequence of this peptide suggested that HeLa cell RBF could be human RXR-β (called hereafter hRXR-β) or a closely related member of the family (in addition, peptide p25 allowed partial discrimination, see FIG. 2). This suggestion was further supported by PCR-assisted cloning and sequencing the portion of the putative hRXR-β cDNA located between peptides p24 and p27 (FIG. 2). The deduced amino acid sequence of 4 clones proved to be nearly identical to that of mRXR-β (see FIG. 2), indicating that hRXR-β might be the major HeLa cell RXR subtype. Therefore, mRXR-β was used to screen a HeLa cDNA library in order to clone the human homolog of this receptor. Of ~$10^5$ colonies screened, seven overlapping clones were obtained which were then subcloned and sequenced (FIG. 2 gives the deduced amino acid sequence of hRXR-β). The longest open reading frame corresponds to a 526 amino acid long polypeptide which is highly similar to mRXR-β and has a predicted MW of 55,821 daltons (FIG. 2 and see below).

The sequence of hRXR-α (Mangelsdorf et al., Nature 345:224–229 (1990)) is strikingly similar (98% identity) in its entirety to that given here for the 466 amino acid long mRXR-α (FIG. 2, and data not shown). The present mRXR-γ 463 amino acid-long sequence is highly similar (83.5%) to that of the chicken RXR reported by Rowe et al., (Development 111:771–778 (1991)). All three RXRs are clearly different from each other, particularly in the A/B and D regions. However, the DNA binding domain (region C) and the putative ligand binding domain (region E) are highly conserved (~90% for each) between all three RXR subtypes. The amino acid sequence of mRXR-β has been previously reported and referred to as H-2RIIBP (Hamada et al., Proc. Natl. Acad. Sci. USA 86:8289–8293 (1989)). The present sequence is longer by 38 amino acid residues (FIG. 2), since our longer cDNA sequence contained an in frame CTG leucine initiator codon (located within a favorable Kozak motif) from which translation could be readily initiated in vitro (our unpublished results). Interestingly, the amino acid sequences of hRXR-β and mRXR-β appear to be highly conserved from the C-terminal to the N-terminal end of mRXR-β, but hRXR-β has an extra 75 amino acid long N-terminal region (FIG. 2). This reflects the existence of RXR isoforms differing in amino terminal sequences which arise from alternative splicing and/or differential promoter usage, as previously reported for RAR-α (Leroy et al., EMBO J. 10:59–69 (1991b)), RAR-β (Zelent et al., EMBO J. 10:71–81 (1991)) and RAR-γ (Kastner et al., Proc. Natl. Acad. Sci. USA 87:2700–2704 (1990)) isoforms (our unpublished results).

As observed for the three RAR types (Zelent et al., Nature 339:714–717 (1989)), there is a higher degree of amino acid sequence conservation for a given RXR type across species (e.g. RXR-α or RXR-β in human and mouse, and RXR-γ in mouse and chicken) than for the three types within a given species, which suggests that the three RXRs perform specific functions. As in the case of RARs, it is particularly striking that the central D region, which is not well conserved between the three RXRs in a given species, is highly conserved for a given RXR type (α, β or γ) across species (FIG. 2 and data not shown).

All Three Cloned RXRs Substitute for Purified HeLa Cell RBF in Promoting DNA Binding of all Three RARs Murine RXRs were translated in vitro with rabbit reticulocyte lysate (RRL) and used to investigate whether cloned RXRs could substitute for the purified HeLa cell RBF in RAR/RARE binding assays. Specific binding of bacterially-expressed hRAR-γ to the β-RARE was observed upon addition of either mRXR-α, β or γ (FIG. 3A, lanes 2–4), whereas binding was not observed in the absence of RXRs (lanes 1 and 5 in FIG. 3A). However, RXRs did not form a specific complex with the β-RARE probe in the absence of hRAR-γ (FIG. 3A, lanes 6–8). All three mRXRs, as well as hRXR-β, translated in vitro could efficiently substitute for HeLa cell RBF in promoting the binding of any one of the three in vitro translated RARs to β-RARE (FIG. 3B; compare lanes 2 and 3, 5 and 6, 8 and 9 and data not shown). Similar results were obtained with mRXR-α expressed in E. coli (our unpublished results). Very little binding was seen with hRAR-α, β or γ in the absence of mRXRs (see lanes 1,4 and 7 in FIG. 3B). mRXR-α was used in most of the experiments described below, but similar results could be obtained with mRXR-β and -γ, or hRXR-β (data not shown).

RAR/RXR Heterodimers Bind Cooperatively to RAREs Much More Efficiently than Isolated RAR or RXR The results displayed in FIGS. 1 and 3 suggested that RAR and RXR may bind cooperatively to β-RARE in vitro. To examine this possibility, experiments were designed to determine if both RAR and RXR were present in the complex formed with β-RARE. We then asked whether the cooperative binding reflected the heterodimeric association of RAR and RXR in solution. We also further investigated whether isolated RAR or RXR could bind to RAREs.

At the concentrations of hRAR-γ used in FIG. 4 (~10 fmoles of receptor per assay), no detectable complex was formed with the β-RARE probe in the absence of HeLa cell RBF or mRXR-α (FIG. 4B, lane 1; see also FIG. 4A, lanes 8 and 17). However, partially purified (FIG. 4B, lane 2) or purified (lane 3) HeLa cell RBF and in vitro translated mRXR-α (lane 5) strongly promoted complex formation. In the absence of hRAR-γ, neither HeLa cell RBF (FIG. 4A, lanes 1 and 2) nor mRXR-α (FIG. 4A, lanes 3 and 12) bound efficiently to the β-RARE probe. To show that RXR was a component of the retarded complex, we constructed an antigen-tagged fusion protein, mRXRαER(F), containing the F region of the human estrogen receptor (ER) (Krust et al., *EMBO J.* 5:891–897 (1986)) fused to the carboxyl terminal amino acid of mRXR-α. This fusion protein contains the epitope for, and can be used in supershift assays with, an anti-ER(F) antibody (AbF3, Ali, S. et al., *Hybridoma* 12:391–405 (1993)). mRXRαER(F) was as efficient as mRXR-α in promoting the binding of RAR-γ to the γ-RARE (compare lanes 5 and 6 of FIG. 4B), but did not bind efficiently to this element on its own (FIG. 4A, lane 4 and 13). The complex formed in the presence of RAR-γ and mRXRαER(F) could be supershifted by either anti-RAR-γ (Ab4γ, FIG. 4B, lane 7) or anti-ER(F) (AbF3, lane 8) antibodies. This indicates that both receptor proteins were present in the heteromeric complex. In contrast, much fainter supershifted complexes were seen when β-RARE was incubated with either isolated mRXRαER(F) (FIG. 4A, lanes 6 and 15) or hRAR-γ (FIG. 4A, lanes 9 and 18) and cognate antibodies. All of these data clearly demonstrate that RAR and RXR bind cooperatively to β-RARE, presumably as heterodimers. In addition, it appears that homomeric complexes can be formed with a low efficiency between β-RARE and either RAR or RXR. However, under the present assay conditions, the visualization of these "low affinity" complexes requires the "stabilizing" effect of receptor antibodies which is most probably due to the bivalent nature of the antibodies.

The above results raise the question as to whether RAR and RXR interact in solution to form heterodimers or whether the observed cooperativity in DNA binding reflects an interaction which occurs once these proteins are bound to the DNA. Crosslinking and coimmunoprecipitation of both proteins with an antibody to one of them was used to investigate these possibilities. A crosslinked product of ~130 kDa was observed when [$^{35}$S]hRAR-γ and unlabeled mRXRαER(F) were incubated in the absence (FIG. 5A lanes 3 and 7) or presence (lanes 5 and 9) of β-RARE prior to chemical crosslinking and immunoprecipitation with either anti-RAR-γ or anti-mRXRαER(F) antibodies. The crosslinked product (upper arrow) was immunoprecipitated by either Ab4γ (FIG. 5A, lanes 3 and 5) or AbF3 (lanes 7 and 9), suggesting the presence of both receptor proteins in the complex. Inclusion of the β-RARE slightly increased formation of this complex (compare FIG. 5A, lane 3 with lane 5 and lane 7 with lane 9), whereas efficient co-immunoprecipitation of non-crosslinked [$^{35}$S]hRAR-γ and unlabeled mRXRαFR(F) by AbF3 required the presence of the βRARE (compare lanes 6 and 8 of FIG. 5A; the position of [$^{35}$S]hRAR-γ monomer is indicated by the lower arrow). No crosslinked product was observed when [$^{35}$S] Met-labeled and unlabeled hRAR-γ were incubated in the absence (FIG. 5A, lane 11) or presence (lane 13) of the β-RARE prior to crosslinking and immunoprecipitation. This finding is consistent with our inability to demonstrate hRAR-γ homodimers using a gel shift assay (FIG. 4B) or by conventional coimmunoprecipitation (data not shown).

Qualitatively similar results were obtained when [$^{35}$S] mRXRaER(F) and unlabeled hRAR-γ were crosslinked in vitro in that the crosslinked complex was evident in the absence of β-RARE (FIG. 5B lanes 3 and 7) and was immunoprecipitated by either. Ab4γ or AbF3 (lanes 3,5 and 7,9, respectively; the migration of the crosslinked complex is indicated by the upper arrow). Moreover, [$^{35}$S] mRXRαER(F) was efficiently co-immunoprecipitated with hRAR-γ by Ab4γ without prior crosslinking, but only in the presence of the β-RARE (compare lanes 6 and 8 of FIG. 5B). A faint crosslinked complex was observed when [$^{35}$S] Met-labeled and unlabeled mRXRαER(F) were incubated in the presence of β-RARE prior to crosslinking and immunoprecipitation (FIG. 5B lane 13, see weak complex slightly above the upper arrow). This finding is consistent with gel shift experiments (FIG. 4A, lanes 12 and 13) which demonstrated that in vitro translated RXR bound weakly to the β-RARE, presumably as a homodimer. Taken together, these results indicate that neither RXR nor RAR homodimerize efficiently in solution or on the β-RARE probe under the present conditions. In contrast, RAR and RXR heterodimerize in solution and this interaction is stabilized by the presence of the β-RARE probe.

Cooperative RAR/RXR Binding is not Restricted to the RAR-β Response Element

Bacterially-expressed hRAR-γ and in vitro translated mRXR-α were used to address the question as to whether the RAR/RXR binding cooperativity could be generalized to other RAR response elements, such as the synthetic TREpal (Glass et al., *Cell* 59:697–708 (1989)) which contains two inverted motifs instead of the directly repeated motifs of β-RARE (see FIG. 4A). hRAR-γ did not bind to TREpal in the absence of either HeLa cell RBF or mRXR-α (FIG. 4B, lane 18, see also FIG. 4A, lanes 25 and 33). However, RAR-γ bound strongly to this element in the presence of partially purified (FIG. 4B, lane 19) or purified (lane 20) HeLa cell RBF, mRXR-α (lane 22) or mRXRαER(F) (lane 23). As expected, the latter complex was shifted by both anti-hRAR-γ (lane 24) and anti-ER(F) (lane 25) antibodies confirming the presence of both receptor proteins in the retarded complex. Interestingly, both mRXR-α and mRXRαER(F) bound more strongly to the palindromic TRE than to the β-RARE probe in the absence of RAR-γ (compare FIG. 4A, lanes 12 and 13 with lanes 29 and 30). In contrast, isolated hRAR-γ formed only a faint complex with TREpal even in the presence of Ab4γ antibody (lanes 26 hand 34). These results suggest that unstable RXR homodimers, but not their possible RAR counterparts, may be better stabilized by binding to palindromic rather than to directly repeated motifs.

The recent results of (Mangelsdorf et al., *Cell* 66:555–561 (1991)) and our unpublished data (Mader et al., *J. Biol. Chem.* 268:591–600 (1993)) indicated that isolated RXR may preferentially bind to, and transactivate from, directly repeated motifs spaced by 1 bp. Therefore, we investigated whether RXR/RAR homo and hetero-complexes would be formed more efficiently on an element consisting of directly repeated motifs spaced by 1 bp instead of 5 bp (as it is the case for β-RARE). Using a 1 bp spaced element (β-RARE1, see FIG. 7), very little complex was formed with either mRXR-α or hRAR-γ alone under the present assay conditions, and efficient complex formation required the presence of both receptors (FIG. 7, lanes 9–10). However, the efficiency of formation of heterodimeric complexes was lower with β-RARE1 than with β-RARE (compare lanes 2 and 10 in FIG. 7).

Both the Ligand and DNA Binding Domains are Involved in Cooperative Binding of RAR and RXR to β-RARE Deletion mutants of each protein were used to investigate whether the integrity of the ligand binding domain (LBD, region E) was required for RXR/RAR cooperative binding. Dimerization interfaces have been previously located within this region of the estrogen and progesterone receptors (see Discussion for references), and the possible existence of similar interfaces has been proposed in the case of RARs (Forman et al., *Mol. Endocrinol.* 4:1293–1301 (1990)). Deletion of hRAR-γ region F had no effect on RAR/RXR binding to β-RARE probe (FIG. 6A, compare lanes 1–4), whereas deletion of a fraction (hRAR-γΔ270–454, lanes 5 and 6) or all of region E (hRAR-γΔEF and hRAR-γΔ188–454, lanes 7–10) resulted in a drastic reduction of β-RARE binding. No obvious C-terminal F region could be defined for mRXRs when their sequence was compared to those of other members of the nuclear receptor superfamily (see FIG. 2, and data not shown). Deletion of the 12 (mRXR-αΔ455–466, FIG. 6B, lanes 1–4) or 18 (mRXRαΔ449–466, data not shown) most carboxyl-terminal amino acids of mRXR-α region E did not affect RAR/RXR binding to β-RARE. However, a further 32 amino acid deletion into the putative RXR LBD (mRXR-αΔ423–466) abolished β-RARE binding (FIG. 6B, lanes 5 and 6). Thus, amino acid sequences located within the LBD of both RAR and RXR are clearly required for cooperative binding to β-RARE.

The possible requirement of RAR and RXR DNA binding domains (DBDs) was investigated using mutants which convert the fourth cysteine of the first "recognition" zinc finger (see Schwabe et al., *Trends Biochem. Sci.* 116:291–296 (1991) for a review) of each receptor to alanine. In the case of hRAR-γ (hRAR-γΔC4, FIG. 6A lanes 13 and 14; see also FIG. 7, lane 5) this mutation resulted in no significant β-RARE binding, whereas in the case of mRXR-α (mRXR-αΔC4, FIG. 6B, lanes 7 and 8; see also FIG. 7, lane 3), the corresponding mutation decreased, but did not eliminate, RARE binding. This suggests that the Cys→Ala mutation is more detrimental to the DNA binding of hRAR-γ than to that of mRXR-α. In contrast, both mRXR-αΔC4 (compare lanes 10 and 11 of FIG. 7) and hRAR-γΔC4 (compare lanes 10 and 13) mutations resulted in the complete loss of binding to β-RARE1 in which the two binding motifs are spaced by 1 bp, and also to the palindromic element TREpal (data not shown). Thus, RAR and RXR may interact differently when bound to response elements made up of either directly repeated motifs with different spacer length or inversely repeated motifs. Finally, deletion of the hRAR-γ N-terminal A/B region did not significantly alter β-RARE binding (hRAR-γΔAB, FIG. 6A, lanes 11 and 12).

RXR-β is also a HeLa Cell TRAP

It has been reported that binding of the thyroid hormone receptors alpha and beta (TR-α and β) to TREs is stimulated by TR binding proteins (also called TR auxiliary proteins. TRAP) present in a variety of cell and tissue extracts (Murray et al., *Mol. Endocrinol.* 3:1434–1442 (1989); Burnside et al., *J. Biol. Chem.* 265:2500–2504 (1990); Lazar et al., *Mol. Endocrinol.* 4:1627–1635 (1990); Spanjaard et al., *Proc. Natl. Acad. Sci. USA* 88:8587–8591 (1991); and references therein). The apparent MWs of these TRAPs ranges from 42–66 kDa as determined by size-exclusion chromatography (Burnside et al., *J. Biol. Chem.* 265:2500–2504 (1990)) and chemical crosslinking to TR (O'Donnell et al., *Mol. Endocrinol.* 5:94–99 (1991); Lazar et al., *Mol. Cell. Biol.* 11:5005–5015 (1991); Naar et al., *Cell* 65:1267–1279 (1991)). Since the purified HeLa cell RBF migrated as a ~64 kDa polypeptide on SDS-PAGE, we performed experiments to determine if this protein could act as a TRAP in gel retardation assays. In vitro translated c-erbA (chicken TR-α1 or cTR-α1) formed a strong complex on β-RARE with either partially purified (FIG. 4B, lane 11) or purified (lane 12) HeLa cell RBF, as well as with in vitro translated mRXR-α (lane 14) or mRXRαER(F) (lane 15). The latter complex could be supershifted by AbF3 (lane 16), indicating the presence of RXRαER(F) in the complex. Stronger c-erbA/RXR complexes were formed on the TREpal than on the β-RARE probe (compare FIG. 4B, lanes 11–16 and 28–33), whereas the converse was true in the case of RAR/RXR complexes (compare FIG. 4B, lane 2–8 and 19–25). In contrast to RARs and RXRs, c-erbA appeared to bind as a monomer to TREpal (FIG. 4B, lane 27), but not to β-RARE (lane 10). Furthermore, this putative c-erbA monomeric complex could be fully shifted into a presumably heterodimeric complex upon addition of either partially purified (FIG. 4B, lane 28) or purified (lane 29) HeLa cell RBF, in vitro translated mRXR-α (lane 31) or RXRαER(F) (lane 32). The latter complex was supershifted by AbF3 (lane 33), confirming the presence of mRXRαER(F) in the complex. Taken all together, these results strongly suggest that hRXR-β is a HeLa cell TRAP. To determine if hRXR-β is indeed the major TRAP present in HeLa cells, we carried out a HeLa cell extract purification, simultaneously monitoring RBF and TRAP activity by using gel shift assays. These two activities co-eluted during each chromatographic step, and we found no evidence to suggest the existence of significant additional TRAP activities in HeLa cells (data not shown). Therefore, it appears that HeLa cell TRAP and RBF activities corresponds to the same entity, i.e., predominantly hRXR-β.

Glass et al., *Cell* 59:697–708 (1989) reported that hRAR-α and hTR-β may heterodimerize in vitro and in vivo. We, therefore, assumed that c-erbA might be able to substitute for RXR in cooperative binding with hRAR-γ to β-RARE. Surprisingly, c-erbA did not bind cooperatively with hRAR-γ to either β-RARE (FIG. 4B, lanes 4 and 13) or TREpal (lanes 21 and 30) probes. Therefore, if c-erbA and RAR-γ heterodimerize, this interaction is too weak to be seen using the present gel shift assay conditions. In contrast, under identical conditions, RXR strongly heterodimerizes with either c-erbA or RAR on both β-RARE and TREpal probes (FIG. 4B).

mRXR Over Expressed in Cells in Culture Enhances the Binding of Endogenous RARs

To demonstrate that RXR expressed in vivo binds cooperatively with endogenous RARs, we performed supershift gel retardation experiments using the β-RARE probe and extracts prepared from Cos cells transfected with a mRXR-α expression vector. As a control, extracts were also prepared from cells transfected with the parental expression vector pSG5 (Green et al., *Nucl. Acid. Res.* 16:369 (1988)). No β-RARE specific complex could be observed using extracts prepared from pSG5-transfected cells either in the absence (FIG. 8, lane 1) or presence of antibodies specific for hRAR-α (Ab9α, lane 2), hRAR-β (Ab7β, lane 3) or hRAR-γ (Ab4γ, lane 4). However, when extracts prepared from mRXR-α-transfected cells were used in similar assays, a specifically retarded complex was observed (FIG. 8, lane 5, lower arrow). Interestingly, this complex was partially supershifted by Ab9α (lane 6) and Ab4γ (lane 8) antibodies (upper arrow) but not by the antibody Ab7β (lane 7). Simultaneous addition of Ab9α and Ab-4γ (lane 10), or of all three antibodies (lane 12), resulted in a complete supershift of the complex. Similar results were obtained by transfecting mRXR-β or mRXR-γ expression vectors into Cos cells (data not shown). These findings are consistent with Northern blot data which indicate the presence of RAR-α and -γ, but not RAR-β, mRNAs in Cos cells grown in the absence of retinoic acid (P. Leroy, unpublished results). Thus, over expressed RXRs can promote the cooperative binding of endogenous Cos cell RAR-α and -γ to β-RARE in vitro. Moreover, these results directly implicate endogenous RAR-α and -γ in the DNA binding activity of transfected RXR, and indicate that, under the present conditions, RAR-α and RAR-γ were the only Cos cell proteins which could form stable heterodimers with RXR. Similar observations were made with extracts of HeLa and CV1 cells transfected with a mRXR-α expression vector (data not shown).

Discussion

RXRs Correspond to the Protein Activities Required for Efficient Binding of BAR and TR to Response Elements in vitro The present purification and cDNA cloning demonstrate that the HeLa cell protein responsible for enhanced binding of RARs and TRs to response elements (REs) is predominantly hRXR-β. hRXR-α and γ may also be present in HeLa cells, since low levels of the corresponding transcripts could be detected (data not shown) and, in fact, all three RXRs are able to enhance RAR or TR binding. Moreover, our results clearly show that the enhancing activity of the three RXR types is not restricted to RARs overproduced in various expression systems or translated in vitro, since RXRs produced in Cos, HeLa and CV1 cells efficiently stimulate the binding of RARs (α and γ) present in these cells. Our data also indicate that these endogenous RARs are the only proteins which can form stable heterodimeric complexes on β-RARE with over expressed RXR (FIG. 8, and data not shown). This does not rule out the likely possibility that RXRs could also correspond to the factor which is required for efficient binding of vitamin D3 receptor (VDR) to its target sequence (Liao et al., *Proc. Natl. Acad. Sci. USA* 87:9751–9755 (1990); Darling et al., *Mol. Endocrinol.* 5:73–84 (1991)).

Crosslinking experiments have indicated the possible presence of an additional minor 55 kDa RBF species in HeLa cells (which may correspond to another RXR, such as RXR-α or -γ, see above) and of a major RBF species with an apparent MW of 45 kDa in HL60 nuclear extracts (Glass et al., *Cell* 63:729–738 (1990)). Lazar et al., *Mol. Cell. Biol.* 11:5005–5015 (1991) have also described a 42 kDa liver protein which enhances TR DNA binding. It seems unlikely that this protein and the 45 kDa HL60 cell protein correspond to RXRs, since the MWs of all described RXRs range from ~48–56 kDa, and all migrate with an even larger apparent MW on protein gels (our unpublished results). The use of antibodies against RXRs will be necessary to determine whether these smaller proteins belong to another class of RAR/TR binding proteins or correspond to truncated RXR forms resulting from alternative splicing events similar to those occurring for RARs (Kastner et al., *Proc. Natl. Acad. Sci. USA* 87:2700–2704 (1990); Leroy et al., *EMBO J.* 10:59–69 (1991b); Zelent et al., *EMBO J.* 10:71–81 (1991)) or artefactual proteolysis.

Surprisingly, we found strong RBF activities in extracts of both *Spodoptera frugiperda* Sf9 and Drosophila Schneider S2 cells (FIG. 1C). These extracts similarly enhanced TR binding (data not shown), thus suggesting that functional homologs of RXR may be conserved from insects to humans. (Yang et al., *Proc. Natl. Acad. Sci. USA* 88:3559–3563 (1991)) have also mentioned a RBF activity in S2 cell extracts. The Drosophila ultraspiracle (usp) protein (Oro et al., *Nature* 347:298–301 (1990)) is related to RXR (86% and 49% sequence similarities in DNA and ligand binding domains, respectively). Whether the S2 and Sf9 cell RBF and TR binding activities correspond to the usp protein and its Sf9 homolog, remains to be established. However, our results raise the possibility that a Drosophila member(s) of the nuclear receptor superfamily (e.g. the ecdysone receptor, EcR, for references see (Koelle et al., *Cell* 67:59–77 (1991); Segraves, *Cell* 67:225–228 (1991)) could be the partner of the S2-cell RBF. It is therefore possible that interactions between members of the nuclear receptor family predate the divergence of insects and vertebrates. RAR/RXR and TR/RXR heterodimers bind more strongly to RARE and TRE than the corresponding homodimers. Under the present gel shift assay conditions (150 mM KCl, room temperature, limiting concentration of receptors), we observed very little DNA binding of isolated RAR or RXR even in the presence of "stabilizing" antibodies, and in all cases, RAR/RXR and TR/RXR combinations bound much more efficiently to RARE and TREpal than the individual receptors. Crosslinking and co-immunoprecipitation experiments indicated that RAR and RXR were bound as heterodimers (FIG. 5). Since RAR/RXR-RE and TR/RXR-RE complexes migrated similarly in gel shift assays, we infer that TR and RXR were also bound as heterodimers.

Our results apparently contradict those of several groups who have reported the formation of RAR-RARE complexes in vitro (Glass et al., *Cell* 59:697–708 (1989); Glass et al., *Cell* 63:729–738 (1990); Darling et al., *Mol. Endocrinol.* 5:73–84 (1991)). This discrepancy can be attributed, at least in part, to the use by these groups of the avidin-biotin complex DNA binding (ABCD) assay which can certainly detect weaker protein DNA interactions than the gel shift assay, since the conditions for separating free and complexed DNA are much less drastic in the former. In addition, the ABCD assay is usually carried out at 50 mM NaCl, rather than at the more physiological condition of 150 mM KCl used in the present study. In fact, formation of RAR and RXR homodimeric complexes on the β-RARE or TREpal probes could also be detected by gel shift assay provided a much higher concentration of receptor was used, and the ionic strength lowered during the binding reaction (Mader et al., *J. Biol. Chem.* 268:591–600 (1993); see also Mangelsdorf et al., *Cell* 66:555–561 (1991) and Yang et al., *Proc. Natl. Acad. Sci. USA* 88:3559–3563 (1991) for RAR binding, and Beebe et al., *Mol. Endocrinol.* 5:85–93 (1991) for TR binding). The gel shift and ABCD assays nevertheless yield qualitatively similar results since, using the ABCD assay at 50 mM NaCl, (Glass et al., *Cell* 63:729–738 (1990)) found that the affinity of isolated RAR was much higher for β-RARE than for TREpal, which is in agreement with our gel shift assay displayed in FIG. 4A (compare lanes 18 and 34). Moreover, these authors reported that the addition of HeLa cell nuclear extracts increased the relative affinity of RAR for β-RARE by ~15-fold, whereas we found an ~40–50-fold increase in affinity using the gel shift assay in the presence of RXR (data not shown).

In contrast to steroid hormone receptors, notably the oestrogen receptor (ER), which are present as dimers in solution (Linstedt et al., *J. Steroid Biochem.* 24:677–686 (1986); Skafar, *Biochem.* 30:6148–6154 (1991)), RAR, TR and RXR have been shown to exist as monomers in solution, by using either size exclusion chromatography or velocity centrifugation (Perlman et al., *J. Biol. Chem.* 257:930–938 (1982); Nervi et al., *Proc. Natl. Acad. Sci. USA* 86:5854–5858 (1989); and our present and unpublished results). Therefore, the observed cooperative binding of RXR with either RAR or TR could occur by two distinct mechanisms. Monomers could bind independently to each motif of the RE (as apparently the TR does, see Lazar et al. (*Mol. Cell. Biol.* 11:5005–5015 (1991); Forman et al., *Gene* 105:9–15 (1991); and FIG. 4B), and this binding could be stabilized by heterodimeric interactions which would be more stable than homodimeric interactions. Alternatively, unstable heterodimers, but not homodimers, may be formed in solution, and this interaction may be further stabilized by DNA binding. The latter possibility is supported by our observations that RAR/RXR heterodimers could be crosslinked in solution under conditions where no significant crosslinked homodimers were detected (FIG. 5). Moreover, the presence of a RE resulted in a slight increase of crosslinked heterodimers, whereas crosslinked homodimers were still poorly formed. Thus, unstable RXR/RAR dimers (and presumably also RXR/TR dimers) are present in solution, and the heterodimeric interaction is further stabilized by binding to the RE. In this respect Lazar et al. (*Mol. Cell. Biol.* 11:5005–5015 (1991)) have reported that TR may form an heterodimer with the 42 kDa liver protein, under conditions where no TR homodimer could be observed. Similarly, Glass et al. (*Cell* 63:729–738 (1990)) have shown that RAR may form an heterodimer with the 65 kDa HeLa cell protein, under conditions where RAR homodimers could not be detected.

Dimertization Interfaces and Binding Efficiency of Homo- and Heterodimers to Different Response Elements Dimerization domains are known to be associated with the ligand binding domain (LBD, region E) of the oestrogen (Kumar et al., *Cell* 55:145–156 (1988)) and progesterone (Guiochon-Mantel et al., *Nature* 336:695–698 (1988)) receptors. Amino acids critical for dimerization have been identified in the C-terminal region of the ER LBD (Fawell et al., *Cell* 60:953–962 (1990); see FIG. 9). Forman et al. (*Mol. Endocrinol.* 4:1293–1301 (1990)) have proposed that the LBD of TR, RAR and VDR may contain a dimerization domain consisting of nine heptad repeats, in which hydrophobic amino acids are present at positions 1 and 8 of the repeat, and hydrophobic amino acids or charged amino acids with hydrophobic side chains (Arg, Glu) in the fifth position, thus generating a dimerization interface on one side of an α-helix. Deletion of RXR heptad 9 (Forman et al., *Mol. Endocrinol.* 4:1293–1301 (1990)) abolished the formation of RAR/RXR heterodimers (mRXR-α$\Delta$423–466 in FIG. 6B; see FIGS. 2 and 9 for sequences). A larger truncation in RAR which also deleted heptad 9 (hRAR-γ$\Delta$270–454 in FIG. 6A), as well as point mutations within this heptad (M.S., unpublished results), similarly abolished RAR/RXR heterodimer formation. Point mutagenesis in the corresponding ER heptad also eliminated ER dimerization (Fawell et al., *Cell* 60:953–962 (1990); see FIG. 9). Whether heptads 1–8 also contribute to the RAR/RXR dimerization interface remains to be investigated.

Clearly, even though the heptad repeats of RAR, TR and RXR are related, there must be differences in the dimerization interfaces of these receptors, which result in much stronger RAR/RXR and TR/RXR heterodimers than either RAR, TR and RXR homodimers or RAR/TR heterodimers. Note the presence of a proline residue in the putative heptad repeat 9 of RXRs, instead of a threonine residue in RAR, TR and EcR (FIG. 9). Therefore, it is more likely that the RXR heptad repeat 9 corresponds to the residues located at positions 420–427 in RXR-α and/or at positions 435–442 (FIG. 9). In this respect, RXRs are similar to a number of mammalian and Drosophila orphan receptors (FIG. 9). Interestingly, a mutation which affects the Pro residue preceding cTR-α1 heptad 9 abolishes the ability of this receptor to dimerize in vitro (Selmi et al., *J. Biol. Chem.* 266:11589–11593 (1991)). The above similarities raise the possibility of the existence of separate classes of nuclear receptors with members of one class forming heterodimers more efficiently with members of another class than amongst themselves.

The DNA binding domain (DBD) of steroid hormone receptors contains an additional weaker dimerization domain (Kumar et al., *Cell* 55:145–156 (1988)), which has been localized in the second DNA binding zinc finger by NMR and X-ray crystallography studies (Schwabe et al., *Trends Biochem. Sci.* 116:291–296 (1991); Luisi et al., *Nature* 352:497–505 (1991); and references therein). A similar domain may also exist in the case of RAR, since RAR DBDs expressed in *E. coli* do bind at low ionic strength to wild type β-RARE as dimers, and also as monomers to a β-RARE mutated in one of the directly repeated motifs, albeit with a much lower affinity (Mader et al., *J. Biol. Chem.* 268:591–600 (1993)). However, the stability of the resulting DBD dimeric complex is much lower than that of full length RAR/RXR heterodimers. Whether a weak dimerization domain could also be present in the RXR DBD, and interactions between the second zinc fingers of RAR and RXR be involved in the formation of RAR/RXR heterodimers, remains to be seen.

Several of our observations indicate that the efficiency of RAR, TR and RXR homo- and heterodimer binding is dependent on the precise arrangement (orientation and spacing) of the repeated motifs which constitute the RE. This is dramatically illustrated in the case of RAR and RXR mutated in their first zinc finger (FIGS. 6 and 7). The integrity of this RXR finger was required for RAR/RXR cooperative binding to TREpal and also to an element in which the motifs are spaced by 1 bp (β-RARE1), but not β-RARE where they are spaced by 5 bp. In marked contrast, a mutation in the first RAR finger eliminated binding to all three elements. Thus, the same mutation in the first finger completely abolishes the ability of RAR, but not RXR, to bind DNA. The residual RXR DNA binding, in conjunction with the RAR/RXR dimeric interaction, may be sufficient to allow the visualization of a RAR/RXR complex with β-RARE, but not with REs in which the two motifs are either spaced by 1 bp or inverted (TREpal), presumably because these latter motif arrangements decrease the interaction between the dimerization interfaces of RAR and RXR. In keeping with this interpretation, we note that wild-type RAR/RXR dimers cooperatively bind less efficiently to both β-RARE1 (FIG. 7) and TREpal (FIG. 4B) than to β-RARE. It will be interesting to investigate whether the same heptad repeats of the LBD (and therefore the same dimerization interfaces) are involved in RXR/RAR dimerization on motifs arranged in different manners, and also to determine, in each case, the possible contribution of the dimerization interface which may possibly result from DBD interactions. Similar studies may also reveal why, in contrast to RAR/RXR heterodimers, TR/RXR heterodimers bound better to TREpal than to β-RARE (FIG. 4B).

The weaker specific DNA binding of RAR, RXR and TR homodimers is also modulated by the nature of the REs (see FIGS. 4 and 7). Future studies will establish whether, and how, the DBD and LBD dimerization domains are involved in these differential homodimer bindings and also whether, on some as yet uncharacterized target sequences, the binding efficiency of RAR and RXR homodimers could reach the levels presently achieved with RAR/RXR heterodimers Implications for the Generation of Highly Pleiotropic Effects by Convergence of Nuclear Receptor Signaling Pathways The finding that both the RAR (Ruberte et al., *Seminars in Dev. Biol.* 2:153–159 (1991a) and references therein) and TR (Yaoita et al., *Proc. Natl. Acad. Sci. USA* 87:7090–7094 (1990)) families comprise multiple members (types), each being encoded by a separate gene whose primary transcripts can be differentially spliced to generate multiple evolutionarily conserved isoforms, has led to the speculation that the highly pleiotropic effects of the corresponding ligands, particularly of RA, could be accounted for, at least in part, by the functional specificity of the multiple receptor types and of their isoforms. Moreover, it is increasingly clear that the formation of heterodimers between transcription factors is crucial for generating increased diversity of transcriptional controls with a limited number of regulatory proteins (for a review see Lamb et al., *Trends in Biochem. Sci.* 16:417–422 (1991)). For example, in the leucine zipper class of transregulators, multiple members of the Jun/Fos and ATF/CREB families can homodimerize and heterodimerize, and the resulting homodimers and heterodimers may exhibit different transcriptional activity (reviewed in (Abate et al., *Seminars in Cancer Biol.* 1:19–26 (1990); Nakabeppu et al., *Cell* 64:751–759 (1991); Hai et al., *Proc. Natl. Acad. Sci. USA* 88:3720–3724 (1991); and references therein). The importance of heterodimerization for the generation of transregulator diversity is also remarkably illustrated in the case of basic helix-loop-helix (bHLH) proteins, most notably in the case of myogenic HLH factors (Weintraub et al., *Science* 251:761–766(1991); Lassar et al., *Cell* 66:305–315 (1991); Sun et al., *Cell* 64:459–470 (1991); Benezra et al., *Cell* 61:49–59 (1990); Sun et al., *Mol. Cell. Biol.* 11:5603–5611 (1991) and references therein). Could the formation of RAR/RXR and TR/RXR heterodimers be similarly responsible for generating an increase diversity in the transcriptional response to RA and thyroid hormones? For the sake of simplicity, and also because TR appears to be able to bind as monomer much more efficiently than either RAR or RXR, the following discussion is mainly restricted to the RAR/RXR couple. The possible combination of each isoform of RAR-α, β and γ with any of RXR isoforms would obviously generate a large number of heterodimers, which may potentially exert specific functions at the various levels of the transcriptional activation process. At the level of DNA binding, even though we did not observe any preferential binding of different sets of RAR/RXR heterodimers to various target sequences under the present assay conditions, it is possible that a particular RAR/RXR heterodimer may have a higher affinity for a particular target sequence within the context of the other proteins bound to a particular promoter. In this respect, it is noteworthy that RA response elements appear to be increasingly diverse in the actual sequence, orientation and spacing of the repeated motifs (see Vasios et al., *EMBO J.* 10:1149–1158 (1991) and Leroy et al., *Proc. Natl. Acad. Sci. USA* 88:10138–10142 (1991a)), and also that the multiple RAR and RXR types and isoforms are individually highly conserved across species.

At the level of the transcriptional activation process, the combination of the RAR and RXR trans-activation functions (TAFs) in the heterodimers may generate a greater diversity in the multiple protein interactions which are responsible for triggering initiation of RNA synthesis from a particular promoter. Ligand-dependent TAFs have been shown to be located in the LBDs (E regions) of both RARs and RXRs (M. S. and P. C., unpublished results). In addition, the N-terminal A/B regions of RARs, which are isoform-specific, appear to contain a modulating function which is required for efficient transcriptional activation from some RA-responsive promoters (Nagpal et al., *Cell* 70:1007–1019 (1992); as yet, no data are available concerning the possible role of RXR A/B regions). Thus, the multiple RAR and RXR types and isoforms conceptually allow the formation of a large number of specific heterodimers, which may each have specific transcriptional properties. Interestingly, the natural ligand (RX) which activates RXR TAFs appears to be a new stereoisomer of RA (J. F. Grippo and A. A. Levin, personal communication). Thus, the contribution of RAR/RXR heterodimers to activation of transcription from a particular responsive promoter within a given cell, may depend on the actual concentration of RAR, RXR, RA and RX, and of the cell-specific transcriptional intermediary factors, responsible for coupling RAR and RXR TAFs to the transcription machinery (see Tasset et al., *Cell* 62:1177–1187 (1990), and references therein). Combined small variations in the concentration of some of these molecules may result in significant differences in transcriptional activity which may be particularly important for pattern formation during development. By analogy to what has been recently observed in the case of Fos/Jun homo- and heterodimers (Kerppola et al., *Cell* 66:317–326 (1991a); Kerppola et al., *Cell* 66:317–326 (1991b)), it is tempting to speculate that a given RAR/RXR heterodimer bound to a specific target sequence may bend DNA in a specific orientation, dictating the interactions which can occur by DNA looping (see Ptashne et al., *Nature* 346:329–331 (1990) for a review) between the RAR/RXR heterodimer and factors bound to the corresponding promoter. Such possibilities may account for the opposite transcriptional effects (activation or repression) which have been observed on different response elements (Naär et al., *Cell* 65:1267–1279 (1991), and references therein). That the ligand binding, transactivation and dimerization domains overlap in the same region, may also explain why, depending on the response element, one can paradoxically observe with the same receptor either a ligand-independent activation or a ligand-dependent repression of transcription (Naär et al., *Cell* 65:1267–1279 (1991)). Indeed, the heptad repeat dimerization interface, and therefore both DNA bending and the conformation of the trans-activating domain, may be different on different target sequences.

The wide distribution of RXRs at low levels in mouse embryos at various stages of development and in adult tissues (Mangelsdorf et al., *Nature* 345:224–229 (1990) and our unpublished results), and the more restricted patterns of expression of the three RARs (Ruberte et al., *Development* 111:45–60 (1991b)), raises the interesting possibility that RXRs play a role analogous to that of E47 and E12 proteins in the case of the bHLH factors. As proposed by Weintraub and collaborators Lassar et al. (Lassar et al., *Cell* 66:305–315 (1991)) such a heterodimeric partnership, and the competition for a limiting commonly required DNA-binding partner, may provide mechanisms both for making mutually exclusive "decisions" during development and for generating threshold transcriptional responses which may be particularly important at early stages of embryogenesis. In this respect, competition between RARs, TRs and possibly other members of the same subclass of nuclear receptors such as VDR or peroxisome proliferator activated receptor (Issemann et al., *Nature* 347:645–650 (1990)) for limiting RXR, may prevent the functioning of the least abundant receptors and modulate cellular responsiveness to particular ligands. Indeed, that high levels of TR expression can repress RAR activity (Graupner et al., *Nature* 340:653–656 (1989); Hudson et al., *Cell* 62:1165–1175 (1990)) may correspond to a competition for RXR. Similarly, we have observed that RXRs can enhance the binding of v-erbA to TREpal (unpublished results), and this may account, at least in part, for the negative trans-dominant effect of v-erbA on activation of transcription by TR (Damm et al., *Nature* 339:593–597 (1989); Sap et al., *Nature* 340:242–244 (1989); Disela et al., *Genes Dev.* 5:2033–2047 (1991)), and also suggests that, by sequestering RXRs, v-erbA may possibly exert a similar negative effect on RAR function (see Sharif et al., *Cell* 66:885–893 (1991) and Desbois et al., *Oncogene* 6:2129–2135 (1991)). Similarly, one may consider the possibility that the block in promyelocyte differentiation which occurs in the acute promyelocytic leukemia (APL) characterized by the accumulation of the chimeric fusion MylRAR protein resulting from a t(15;17) translocation (Kakizuka et al., *Cell* 66:668–674 (1991); Kastner et al., *EMBO J.* 11:629–682 (1992) Pandolfi et al., *Oncogene* 6:1285–1292 (1991); de The et al., *Cell* 66:675–684 (1991)), could be related to a sequestration of RXR by MylRAR. It is also tempting to speculate that the early ecdysone response gene E75, which belongs to the same receptor subclass as EcR (Koelle et al., *Cell* 67:59–77 (1991); Segraves, *Cell* 67:225–228 (1991)), may dimerize with the same partner as EcR and thereby inactivate the first ecdysone response while simultaneously triggering the late response.

Genetic studies abolishing the expression of the multiple RAR and RXR genes in cultured cells and in the mouse (e.g. by homologous recombination in ES cells) will be necessary to investigate to what extent the heterodimeric interactions that we have observed in the present in vitro study correspond to a combinatorial convergence of the two retinoid signalling pathways on the promoters of target genes in vivo. Similar studies will also reveal to what extent the retinoid and thyroid hormone signaling pathways are converging in vivo and, more generally, whether similar heterodimeric interactions between other members of the nuclear receptor superfamily (including the numerous orphan receptors) are involved in the control of gene expression by the nuclear receptor signaling pathways.

Experimental Procedures

Expression of Recombinant Proteins

Construction of recombinant vaccinia virus expression vectors, infection of HeLa cells with these vectors and preparation of nuclear extracts from these cells have been previously described (Nicholson et al., *EMBO J.* 9:4443–4454 (1990)).

Construction of the rBV expression vector and preparation of WCE from rBV-infected SF9 cells is being described elsewhere (Chen et al., manuscript in preparation).

A BamHI fragment of hRAR-γ (Nicholson et al., *EMBO J.* 9:4443–4454 (1990)) was inserted into the BamHI site of pEt3a (a gift from W. Studier (Studier et al., *Methods in Enzymol.* 185:60–89 (1991)), to make pEtRARγ. This IPTG-inducible prokaryotic expression vector encodes a fusion protein composed of 14 amino acids from the parental vector fused to the amino terminal amino acid of full length hRAR-γ. For production of bacterially-expressed hRAR-γ, 10 ng of pEtRARγ was used to transform the BL21 (DE3) plysS strain of *E. coli* and the transformants were grown overnight at 37° C. in media containing 0.1 μg/ml ampicillin and 33 μg/ml chloramphenicol. The culture was then diluted 10-fold and grown to an $OD_{600}$ of 0.6–1.0, at which time IPTG was added to a final concentration of 0.4 mM and the cells were allowed to grow for an additional two hours. The cells were then harvested by centrifugation and resuspended in 2% of the original culture volume in lysis buffer (50 mM Tris-HCl pH 7.8, 1 mM EDTA, 1 mM DTT, 10 μM $ZnCl_2$, 400 mM KCl and 10% glycerol) and lysed by two freeze-thaw cycles followed by a brief pulse of sonication to sheer DNA. The bacterial homogenate was centrifuged in a Beckman Ultracentrifuge (SW60 rotor, 55,000 pm for 1 hour at 2° C.), the supernatant was collected, aliquoted, frozen in liquid nitrogen and stored at –80° C.

For production of proteins translated in vitro, full length RAR (Brand et al., *Nature* 332:850–853 (1988); Krust et al., *Proc. Natl. Acad. Sci. USA* 86:5310–5314 (1989)), RXR (see below) and c-erbA (a gift from B. Vennström (Sap et al., *Nature* 34:635–640 (1986)) expression vectors were linearized 3' of the termination codons with appropriate restriction enzymes. Linearized cDNAs were then transcribed and translated using rabbit reticulocyte lysate according to the manufacturer's (Promega) instructions.

Construction of RAR and RXR Mutants

All 3' deletion mutants of RAR and RXR were constructed by PCR introduction of premature termination codons. However, two RAR deletion mutants, hRAR-γΔ270-454 and hRAR-γΔ188-454, were produced by in vitro transcription and translation of the hRAR-γ expression vector linearized at EcoRV and SacI sites, respectively. hRAR-γΔAB was constructed by PCR amplification of a fragment corresponding to hRAR-γ domains C through F and containing a BamHI site, favorable translational initiation sequence and an ATG at the 5' end of the fragment (5' sequence is GGATCCACC<u>ATG</u>TGC . . . ). This fragment was then subcloned into the BamHI site of pSG5 (Green et al., *Nucl. Acids Res.* 16:369 (1988)).

Cysteine point mutations were created in hRAR-γ and mRXR-α by production of single strand DNA and standard procedures. In hRAR-γΔC4 and mRXR-αΔC4, the TGC codon encoding the fourth cysteine of the first zinc finger was changed to GCC for alanine. In all cases, the authenticity of RAR and RXR mutants was verified by sequence analysis, Western blotting (RAR mutants), in vitro translation in the presence of [$^{35}$S]methionine, and, in the case of some PCR mutants, by isolation and testing of multiple clones.

Gel Retardation Experiments

Gel retardation experiments, including antibody supershift assays, were as previously described (Nicholson et al., *EMBO J.* 9:4443–4454 (1990); and Smith et al., *EMBO J.* 10:2223–2230 (1991)). The anti-hRAR-γ antibody (Ab4γ) has been previously described (Rochette-Egly et al., *J. Cell Biol.* 115:535–545 (1991)). Anti-hRAR-α (Ab9α) and anti-hRAR-β (Ab7β) antibodies have been described elsewhere (Gaub et al., *Exp. Cell. Res.* 201:335–346 (1992); Rochette-Egly et al., *Molec. Endochrinol.* 6:2197–2209 (1992, respectively). The description of the anti-hER(F) antibody (AbF3) has also been published elsewhere (Ali et al., *Hybridoma* 12:391–405 (1993)). For experiments in which RARγ obtained from different sources was used (i.e., rVV, rBV, *E. coli*, in vitro translation), receptor levels were normalized to that of rVV by Western blot. This amount of RARγ corresponded to approximately 10 fmols of receptor per assay (as determined by [$^3$H] retinoic acid binding) in these and all other experiments described in this report. For gel retardation experiments comparing RAR and RXR subtypes and deletion mutants, all proteins were produced by in vitro translation in the presence of [$^{35}$S]methionine. Radiolabeled proteins were analyzed by SDS-PAGE and these data were used to normalize the amount of each unlabeled receptor (which were translated in parallel) used in gel retardation assays. A similar approach was used to estimate that the amount of c-erbA used in gel retardation experiments was approximately 5–10 fmols.

Protein Purification

Purification of rVV- and rBV-expressed hRAR-γ is being described elsewhere (Chen et al., manuscript in preparation). For purification of HeLa cell RBF, HeLa WCE was prepared as previously described (Moncollin et al., *EMBO J.* 5:2577–2584 (1986)). All steps were carried out at 4° C. and RBF activity was monitored through all purification steps by a complementation gel retardation assay using bacterially-expressed hRAR-γ as described above. HeLa WCE (from 90 liters of cells grown in suspension and corresponding to $9 \times 10^9$ cells) was dialyzed overnight against buffer A (50 mM Tris-HCl pH 7.8, 0.1 mM EDTA, 0.5 mM DTT and 10% glycerol) containing 50 mM KCl and loaded (100 ml/hr) onto a 350 ml DEAE-Biogel A column (BioRad) equilibrated in the same buffer. The column was washed with equilibration buffer until the $A_{280}$ of the eluent returned to baseline. The flow-through fraction (DEAE FT, 1350 ml, 112 mg of protein) was made 150 mM in KCl and loaded (80 ml/hr) onto an 80 ml Heparin-Ultragel column (IBF) equilibrated in buffer A containing 150 mM KCl. The column was washed with equilibration buffer to remove unbound proteins and eluted (65 ml/hr) with a 320 ml linear gradient from 150–450 mM KCl in buffer A. RBF activity eluted from this column as a sharp peak centered at 290 mM KCl. Fractions containing RBF activity were pooled (65 ml, 1.95 mg of protein), made 0.9 M in ammonium sulfate and loaded onto a phenyl-5PW column (Beckman, 0.75×7.5 cm, 0.4 ml/min), equilibrated in buffer A containing 0.9 M ammonium sulfate and 50 mM KCl. The column was washed with equilibration buffer until the $A_{280}$ of the eluent returned to baseline and then with 4 column volumes of buffer A containing 0.45 M ammonium sulfate and 50 mM KCl. The column was then eluted with an 18 ml linear gradient from 0.45 to 0 M ammonium sulfate in buffer A containing 50 mM KCl. Fractions containing RBF activity (which eluted from this column at 250 mM ammonium sulfate) were pooled (6 ml, 120 μg protein), dialyzed against buffer A containing 50 mM KCl and applied to a TSK-Heparin 5PW column (Toso-Haas, 0.75×7.5 cm, 0.3 ml/min) equilibrated in the same buffer. This column was washed with equilibration buffer followed by 6 column volumes of buffer A containing 150 mM KCl and then eluted with a 20 ml linear gradient from 150 to 400 mM KCl in buffer A. RBF containing fractions were pooled (7.5 ml, 19 μg of protein, peak at 250 mM KCl), dialyzed against buffer B (10 mM potassium phosphate pH 7.5, 0.01 mM $CaCl_2$, 0.5 mM DTT and 10% glycerol) and loaded onto TSK-HA1000 hydroxylapatite column (Toso-Haas, 0.75×7.5 cm, 0.3 ml/min) equilibrated in buffer B. After washing the column with buffer B and 3 column volumes of buffer B containing 75 mM potassium phosphate, the column was eluted with an 18 ml linear gradient from 75 to 250 mM potassium phosphate in buffer B. The peak of RBF activity eluted from this column at approximately 150 mM potassium phosphate and was estimated to contain approximately 0.2 μg of RBF purified to apparent homogeneity.

Peptide Sequencing of RBF

Multiple preparations of purified RBF were pooled (estimated to contain 5–6 μg of RBF), dialyzed against buffer C (0.5 mM Tris-HCl pH 7.8, 1 μM EDTA, 5 μM DTT, 0.5 mM NaCl, 0.05% SDS) and lyophilized in a speed-vac. The lyophilized material was resuspended in water, electrophoresed on a 7.5 % SDS-PAGE gel and blotted to a PVDF membrane (Millipore). The RBF band was excised and digested with sequencing grade trypsin (Boehringer Mannheim) using standard procedures. Tryptic peptides were separated by reverse-phase HPLC and sequenced by automated Edman degradation on an Applied Biosystems sequencer.

Cloning of mRXRs and HRXR-β

To clone mouse RXR-α, we first employed degenerate PCR primers deduced from the hRXR-α sequence (Mangelsdorf et al., *Nature* 345:224–229 (1990)) to amplify, from mouse liver cDNA, a fragment corresponding to the region encoding amino acid 14–360. Perfectly matching primers were deduced from the sequence of that fragment and used to clone the 5' and 3' sequences of mRXR-α, by performing anchored PCR on liver cDNA (5' end) and PCR on total DNA from a mouse 11.5d embryo λgt10 cDNA library (3' end). The 1883 nucleotide long sequence is accessible in the Genbank data bank under the accession number M84817. The first ATG occurs at position 98, is surrounded by a sequence favorable for translation initiation and preceded by an in frame termination codon (nucl. 6–9).

Mouse RXR-β is the sequence previously designated H-2RIIBP (Hamada et al., *Proc. Natl. Acad. Sci. USA* 86:8289–8293 (1989)). We obtained additional 5' sequence by anchored PCR (performed on 14.5 d embryo cDNA) (Genbank accession number M84818). The first AUG is at position 190 [109 in Hamada et al., *Proc. Natl. Acad. Sci. USA* 86:8289–8293 (1989)) and is preceded by an in frame termination codon (nucl. 64). The sequences surrounding this AUG are not matching the consensus sequence required for efficient initiation of translation. An upstream CUG codon (nucl. 76–78) is partially used for translation initiation when in vitro synthesized mRXR-β RNA containing the entire cloned 5' sequence of mRXR-β is translated in vitro with rabbit reticulocyte lysate (~10% of the produced RXR-β protein; our unpublished results) and may also be used in vivo since the deduced amino acid sequence is conserved upstream of the first methionine between mouse and man.

A partial sequence of mRXR-β was obtained from PCR amplification of mouse heart cDNA with degenerate oligonucleotide primers corresponding to amino acid sequences in the C region conserved between RXR-α and RXR-β (CAICGD and YQKCL for the 5' and 3' primers, respectively). This cDNA fragment was then used to screen a randomly primed mouse heart cDNA library (established in λZAP-II), yielding 2 overlapping clones. The resulting cloned mRXR-r cDNA is 1517 nucleotides long (Genbank accession number M84819). The first AUG (nucl. 35) is surrounded by a sequence favorable for translation initiation and is preceded by an in frame termination codon (nucl. 18).

To clone hRXR-β, a full length [α-$^{32}$P]CTP-labeled mRXR-β probe was used to screen a λZAP-II HeLa cDNA library (Xiao et al., *Cell* 65:551–568 (1991)). The 1738 nucleotide-long sequence is accessible in the Genbank data bank under accession number M84820. The first ATG is situated at position 118–120 and is preceded by an in-frame termination codon (nucl. 52–54).

Construction of Mouse RXR Expression Vectors

The mouse RXR-α expression vector (deposited on Jan. 27, 2003 with American Type Culture Collection, 10801 University Boulevard, Manassas, Va. 20110-2209, accession no. PTA-4958) has been constructed in the pSG5 vector from the fusion of two fragments: EcoRI-NarI, containing sequences between nucleotides 79–1137 and obtained by PCR from mouse liver cDNA and NarI-BamHI, derived from a 11.5d λgt10 library clone containing the end of the coding sequence (from nucleotide 1138) and ~600bp of 3' untranslated sequence. Note the presence of EcoRI, PstI and SmaI sites upstream of the BamHI site in this vector which originate from the Bluescript SK polylinker. mRXRαER(F) is cloned between the EcoRI and BamHI sites of pSG5 and contains the mRXR-α coding sequence (nucleotides 79–1496) fused to the sequences encoding the F region of the human estrogen receptor (nucleotides 1869–2020, (Green et al., *Nature* 320:134–139 (1986)), with an XbaI site created at the junction. The nucleotide sequence at RXR-ER junction is GCCACCCCTTCTAGAACTAGC, encoding ATPSRTS. Note that a proline residue has been introduced to allow for flexibility between RXR-α and ER sequences.

The mRXR-β expression vector (deposited on Jan. 27, 2003 with American Type Culture Collection, 10801 University Boulevard, Manassas, Va. 20110-2209, accession no. PTA-4958) contains the mRXR-β coding sequence (nucleotides 76 to 1439) which is inserted between the EcoRI and HindIII sites of pTL1 (a gift from T. Lufkin, pTL1 is the same as pSG5 but with a EcoRI/BamHI/HindIII/XhoI/NotI/SmaI/PstI/SacI/KpnI/BglII polylinker as a cloning site). The initiation CTG has been transformed into an ATG and placed downstream of a "perfect" Kozak initiation sequence. The 5' sequence in the mRXR-β expression vector is thus GAATTCCACCATGGGACCGGAT . . .

The mRXR-γ expression vector (deposited on Jan. 27, 2003 with American Type Culture Collection, 10801 University Boulevard, Manassas, Va. 20110-2209, accession no. PTA-4958) contains the mRXR-γ nucleotides 35–1517 inserted into the EcoRI site of pSG5. A "perfect" Kozak sequence has been created upstream of the initiation ATG (sequence GAATTCCACCATG).

Crosslinking and Co-Immunoprecipitation Experiments

Disuccinimidyl suberate (DSS, Pierce) was used to chemically crosslink in vitro translated RAR and RXR. Crosslinking and co-immunoprecipitation experiments were performed similarly to gel retardation assays except on a larger scale. For example, ~50 fmols of unlabeled receptor (bacterially-expressed or translated in vitro) were incubated with an equal molar amount of [$^{35}$S]methionine-labeled receptor which was translated in vitro. The incubation was carried out in 50 µl of gel retardation buffer (Nicholson et al., *EMBO J*. 9:4443–4454 (1990)) containing 150 mM KCl and Hepes-NaOH (10 mM, pH 7.5) instead of Tris-HCl. Where indicated, 500 fmols of unlabeled β-RARE were also included in the incubation (note that gel retardation assays were generally carried out using ~10 fmols of hot probe). After the 20 min room temperature incubation, DSS (dissolved in DMSO) was added to a final concentration of 1 mM and 2% DMSO. Control tubes received DMSO only. The crosslinking reaction was performed at 22° C. for 15 minutes and then quenched by addition of lysine (final concentration of 25 mM). After increasing the volume of each reaction to 500 µl with gel retardation buffer, samples were immunoprecipitated as previously described (Rochette-Egly et al., *J. Cell Biol*. 115:535–545 (1991)). Immunoprecipitated proteins were run on SDS gels and [$^{35}$S] labeled proteins were visualized by autoradiography after incorporation of PPO into the gels to enhance the [$^{35}$S] signal.

COS Cell Transfections and Extract Preparation

COS-1 cells (60% confluent, grown on 75 mm plates) were transfected with 10 µg per plate of mRXR-α expression vector and 10 µg of carrier DNA (BSM) and grown for an additional 48 hours in Dulbecco's medium containing 5% delipidated fetal calf serum. Cells were washed and collected in cold PBS and, after centrifugation, resuspended in 100 µl per plate of lysis buffer (identical to *E. coli* lysis buffer described above without $ZnCl_2$). Cells were lysed by three cycles of freeze-thawing (thawing on ice) and the insoluble material removed by centrifugation. The supernatant (Cos WCE) was aliquoted, frozen in liquid nitrogen and stored at −80° C.

TABLE 1

| Step | Protein (µg) | Activity (cpm) | Specific Activity (cpm/µg) | Fold Purification | % Recovery |
| --- | --- | --- | --- | --- | --- |
| WCE | $1.2 \times 10^6$ | $187.2 \times 10^6$ | 156 | 1 | 100 |
| DEAE | $1.1 \times 10^5$ | $160.8 \times 10^6$ | 1461 | 9.4 | 86 |
| HEP-UG | $2.0 \times 10^3$ | $44 \times 10^6$ | 22,000 | 15 (141) | 27 (33) |
| PHENYL-5PW | $1.2 \times 10^2$ | $9.4 \times 10^6$ | 78,333 | 3.5 (508) | 21 (5) |
| HEP-TSK | 19 | $6.0 \times 10^6$ | 315,789 | 4.0 (2030) | 64 (3) |
| HAP-TSK | 0.2* | $1.55 \times 10^6$ | 7,750,000 | 24.5 (49,000) | 26 (0.8) |

Purification of HeLa cell RBF from 90 liters of HeLa cells grown in suspension ($9 \times 10^9$ cells). Fold purification and percent recovery refer to that achieved for a given step followed, in parentheses, by the overall fold purification and percent recovery.
*The amount of HAP-TSK purified protein was estimated from a silver-stained gel.

EXAMPLE 2
Efficient Transactivation by RAR in Yeast Requires RXR

All-trans retinoic acid and 9-cis retinoic acid are natural derivatives of vitamin A which modulate gene expression as a consequence of binding to nuclear retinoic acid (RAR) and retinoid X (RXR) receptors (Chambon, P. et al,. in *Retinoids: 10 Years On*, J. H. Saurat, ed., Basel:Karger (1991); Leid, M. et al., *Trends Biochem*. 17:427–433 (1992); Heyman, R. A. et al., *Cell* 68:397–406 (1992); Levin, A. A. et al., *Nature* 355:359–361 (1992); and additional references cited therein). RXRs form heterodimers with RARs in vitro, and such complexes display enhanced binding affinities for cognate DNA response elements (Yu, V. C. et al., *Cell* 67:1251–1266 (1991); Leid, M. et al., *Cell* 68:377–395 (1992); Zhang, X. K. et al., *Nature* 355:441–446 (1992); Kliewer, S. A. et al., *Nature* 355:446–449 (1992)). As nuclear receptors function in yeast cells (Metzger, D. et al., *Nature* 334:31–36 (1988); Schena and Yamamoto, *Science* 241:965–967 (1988); Mak, P. et al., *J. Biol. Chem*. 264:21613–21618(1989); Purvis, I. J. et al., *Gene* 106:35–42 (1991); Pierrat, B. et al., *Gene* 119:237–245 (1992)). which are devoid of endogenous RARs and RXRs, we used this-organism to investigate whether-transactivation in vivo requires RAR/RXR heterodimers. Using the domain swapping approach (Green and Chambon, *Nature* 324:615–617 (1986)), we demonstrate that chimeric RARα1 and RXRα receptors containing the DNA-binding domain of the oestrogen receptor activate transcription of a cognate reporter gene in yeast, independently of each other. These activities result from an inducible transcription Activation Function (AF-2) in the ligand binding domains of RARα1 and RXRα, and a constitutive activation function (AF-1) in the A/B region of RARα1. The AF-2 of RXRα was induced exclusively by 9-cis derivatives of retinoic acid (RA). Transactivation of a reporter gene containing a retinoic acid response element (RARE) by the natural RARα was strongly increased by coexpression of RXRα, even in the absence of ligand. Optimal induction was achieved with 9-cis retinoic acid which stimulates the activity of both receptors. This study illustrates the utility of yeast to investigate signal transduction by retinoids in the absence of endogenous RARs, RXRs and observable ligand isomerization.

In order to investigate whether the human RARαI and mouse RXRα receptors (hereafter referred to as RARα and RXRα) contain intrinsic abilities to activate transcription, chimeric receptors were constructed in which the native DNA-binding domains (DBDs) were replaced with the DBD of the human oestrogen receptor (ER).

Chimeric receptors were constructed as follows; PCR and site-directed mutagenesis were used to generate EcoR1 fragments containing human RARα1 (Leroy et al., *EMBO J.* 10:59–69 (1991); Petkovich, M. et al., *Nature* 330:444–450 (1987); Giguere, V. et al., *Nature* 330:624–629 (1987)) (RARα) and mouse RXRα (Leid, M. et al., *Cell* 68:377–395 (1992)) (RXRα) cDNAs in which all non-coding flanking sequences are removed. The 5' prime flank of each construct contains a mammalian Kozak's sequence sandwiched between the EcoR1 and the translation start codon (5'-GAATTCCACCATG-3'). The fragments were cloned into the EcoR1 site of the plasmid pSG5 (Green, S. et al., *Nucl. Acids Res.* 16:369 (1988)), and an internal Kpn1 site in the RARα cDNA was destroyed by site directed mutagenesis using the oligonucleotide 5'-GGGCACCTCAATGGATACC-CGGTGCCTCCC-3' to introduce a silent mutation. The sequences encoding the DBDs of RARα (a.a. 88–153) and RXRα (a.a. 140–204) were deleted and replaced with unique Kpn1 and Xho1 sites in a similar way to that described for HE28 (Green and Chambon, *Nature* 324:615–617 (1986)), thus allowing the ER.CAS or ER(C) fragments to be inserted in phase. These are Kpn1-Xho1 fragments encoding the DNA-binding domain of the human oestrogen receptor (ER) gene and were derived from either HE28 (a.a. 185–250; designated "ER-CAS"; Heery et al., *PNAS USA* 90:4281–4285 (1993)) or HE81 (a.a. 176–282; designated "ER(C)"; S. Mader and P. C. unpublished). PCR and site-directed mutagenesis were used to create RARα(DEF)-ER.CAS, RARα1(AB)-ER(C), RXRα(DE)-ER.CAS and RXRα(AB)-ER(C) as shown in FIG. 10a. All sequences generated by PCR or site directed mutagenesis were verified by sequencing. The chimeric receptors were subcloned into the EcoR1 site of the PGK promoter/terminator cassette in the 2μ-derived yeast multicopy plasmids YEp10 and YEp90 (Pierrat, B. et al., *Gene* 119:237–245 (1992)), which carry TRP1 and HIS3 selectable markers, respectively, and orientations were verified by sequencing. Plasmids were transformed into the yeast reporter strain PL3 (MATα, ura3-Δ1, his3-Δ200, leu2-Δ1, trp1::3ERE-URA3) (Pierrat, B. et al., *Gene* 119:237–245 (1992)) by electroporation, and expression of the receptors was verified by Western analysis (our unpublished results). For transactivation experiments, transformants were grown exponentially for approximately 5 generations in selective medium containing uracil in the presence or absence of ligand, in conditions of diffuse light. Preparation of yeast cell-free extracts (Loison, G. et al., *Curr. Genet.* 2:39–44 (1980)), and OMPdecase assays were as described previously (Wolcott and Ross, *Biochem. Biophys. Acta.* 122:532–534 (1966)).

These chimeric receptors (designated RARα1-ER.CAS and RXRα-ER(C) were expressed in a reporter strain containing a chromosomally integrated URA3 reporter gene regulated by three oestrogen response elements (EREs) (Pierrat, B. et al., *Gene* 119:237–245 (1992)).

Induction of the reporter was determined by measuring the specific activity of the URA3 gene product OMPdecase (see above). Ligand dose response experiments (FIG. 10b) showed that both RARα1-ER.CAS and RXRα-ER(C) activate transcription in a ligand-inducible and dose-dependent manner in yeast. Transactivation by RARα1-ER.CAS was comparably stimulated by all-trans retinoic acid (T-RA), 9-cis retinoic acid (9C-RA) (FIG. 10b) or several other derivatives of RA (FIG. 10c), while activation by RXRα-ER(C) was induced only by 9C-RA or 9-cis -3,4-didehydroretinoic acid (9C-ddRA) at the concentrations used (FIGS. 10b and c). This is consistent with recent data on the binding affinities of RARs and RXRs for RA derivatives (Heyman, R. A. et al., *Cell* 68:397–406 (1992); Allenby et al., *Proc. Natl. Acad. Sci USA* 89:30–34 (1993)) and demonstrates the specificity of RXRα for 9-cis derivatives of RA in vivo. In addition, our results show that T-RA, or T-ddRA are not significantly converted to 9-cis stereoisomers in yeast. In contrast, studies in mammalian and Drosophila cells which showed stimulation of RXR activity by high concentrations of T-RA (Heyman, R. A. et al., *Cell* 68:397–406 (1992); Levin, A. A. et al., *Nature* 355:359–361 (1992); Mangelsdorf, D. J. et al., *Cell* 66:555–561 (1991); Mangelsdorf, D. J. et al., *Genes Dev.* 6:329–344 (1992)) suggest that a RA isomerase activity exists in higher eucaryotes, which is apparently absent in yeast.

To identify transcription activation functions (AFs) in RARα and RXRα, we constructed chimeric receptors expressing the A/B or hormone binding domains linked to the DBD of ER. RARα(DEF)-ER.CAS (FIG. 10a), increased the OMPdecase activity 10-fold in the presence of 9C-RA or T-RA (Table 2) indicating that RARE contains an inducible AF (AF-2) in the ligand binding domain which is functional in yeast, as has been found for nuclear receptors (Pierrat, B. et al., *Gene* 119:237–245 (1992); Wright, A. P. H. et al., *J. Biol. Chem.* 265:14763–14769 (1990); Meyer et al., *J. Biol. Chem.* 267:10882–10887 (1992)). RARα1(AB)-ER(C) (FIG. 10a) increased the activity of the reporter (approx. 150-fold above background) in a ligand-independent manner (Table 2). Thus we conclude that the A/B region of human RARα1 contains an autonomous AF (designated AF-1), in keeping with recent results from our laboratory showing that the transactivation properties of RARs and RXRs in mammalian cells are modulated by their A/B domains, depending on the promoter environment (Nagpal, S. et al., *Cell* 70:1007–1019(1992)). Interestingly, RARα1-ER.CAS exhibited some ligand-independent activation (Table 2), in contrast to the ER receptor expressed in the same reporter strain (Pierrat, B. et al., *Gene* 119:237–245 (1992)), which suggests that the chimeric RARα does not require ligand to bind EREs. RXRα was also found to contain an inducible AF-2 in its ligand binding domain, as RXRα(DE)-ER.CAS stimulated the reporter activity 5-fold in the presence of 9C-RA (Table 2). In contrast to the corresponding RARα receptors, RXRα.ER.(C) and RXRα (DE)-ER.CAS displayed similar degrees of induction (5-fold) in response to 9C-RA (Table 2), suggesting that the A/B domain of RXRα does not contribute significantly to transcriptional activation of this reporter. Indeed, we did not observe any URA3-reporter activation by RXRα(AB)-ER (C) in yeast (Table 2). However, the possibility that this construct may activate transcription from other promoters cannot be excluded. It is unclear why the constitutive and induced activities of RXRα(DE)-ER.CAS are 10-fold higher than those observed for RXRα-ER(C) in these experiments (Table 2). Note, however, that RARα-ER(C) was expressed at a much lower level than RXRα(DE)-ER.CAS (as determined by immunoblots), while RARα1-ER.CAS and RARα(DEF)-ER.CAS were expressed at similar levels (data not shown). The above results demonstrate the presence of activation functions in RARα (AF-1 and AF-2) and RXRα (AF-2) which can activate transcription autonomously in yeast cells.

To investigate if these functions were sufficient to achieve RA-enhanced transcription with the natural receptor(s) in vivo, we constructed a URA3 reporter gene containing a synthetic RARE element (FIG. 11a).

To construct the reporter gene, a HindIII-Pst1 fragment from the plasmid pFL39-1ERE-URA3 (Pierrat, B. et al., *Gene* 119:237–245 (1992)) containing a single oestrogen response element (ERE) and part of the URA3 promoter was cloned into pBLUESCRIPT SK- (Stratagene). By site directed mutagenesis, the ERE sequence (position −139 relative to the translational start site) was removed and restriction sites for BglII and Nhe1 were generated; these sites were used to insert an oligonucleotide containing the DR5 sequence shown in FIG. 11a. The HindIII-Pst1 DR5-URA3 promoter fragment was recloned into the parent vector to yield pFL39-DR5-URA3. The complete URA3 coding sequence with its DR5-URA3 promoter was excised by XmaI digestion and recloned into the XmaI site of the LEU2 containing centromeric plasmid pRS315 (Sikorski and Hieter, *Genetics* 122:19–27 (1989)). Human RARα1 (Leroy et al., *EMBO J.* 10:59–69 (1991); Petkovich, M. et al., *Nature* 330:444–450 (1987); Giguere, V. et al., *Nature* 330:624–629 (1987)) (a.a. 1 to 462), mouse RXRα (Leid, M. et al., *Cell* 68:377–395 (1992)) (a.a. 1 to 467), mouse RXRαdn (Durand, B. et al., *Cell* 71:73–85 (1992))) (a.a. 1 to 448), human RARαdnΔAB (a.a. 88 to 396; gift of S. Nagpal) and mouse RXRαdnΔAB (a.a.s 140 to 448; gift of S. Nagpal) cDNAs were inserted into the EcoR1 sites of the yeast expression vectors YEp10 and YEp90 according to standard procedures. Transactivation assays were as described above. Plasmids were introduced into the yeast strain YPH250 (MATa, ura3–52, lys2-801, ade2-101, trp1-Δ1, his3-Δ200, leu2-Δ1) (Sikorski and Hieter, *Genetics* 122:19–27 (1989)) by sequential transformation. Coexpression of two different receptors had no observable effect on the level of proteins detectable in yeast cell-free extracts by Western analysis (data not shown). Reporter activity was measured as described above and is given as specific activity (b) or fold induction over basal activity (c) as indicated.

This response element is a direct repeat of the motif 5'-AGGTCA-3' separated by a spacer of 5 base pairs (DR5), which is derived from the RARE of the RARβ$_2$ gene previously shown to function as a RA-inducible enhancer in mammalian cells (Mangelsdorf, D. J. et al., *Cell* 66:555–561 (1991); de Thé, H. et al., *Nature* 343:177–180 (1990); Mader, S. et al., *J. Biol. Chem.* 268:591–600 (1993)). Receptors were expressed in an appropriate yeast strain carrying the DR5-URA3 reporter gene on a single copy vector. In transformants expressing either of the receptors alone, no increase was observed in reporter basal activity (i.e. control without receptors) in the absence of ligand (measured as OMPdecase activity, FIG. 11b). In clones expressing RARα alone, T-RA or 9C-RA ($5 \times 10^{-7}$ M) both induced the OMPdecase activity approx. 5-fold, showing that RARα can activate transcription of a DR5 element in vivo, albeit weakly, in a ligand-dependent manner in the absence of RXR. Clones expressing RXRα alone showed an even weaker (2-fold) increase in reporter activity in response to 9C-RA, but not T-RA. Remarkably, however, coexpression of RARα and RXRα strongly increased both the constitutive and induced levels of reporter gene activity. The constitutive activity was 18-fold above that of the control, while the T-RA and 9C-RA -induced activities increased to approx. 30-fold and 60-fold above the control, respectively (FIG. 11b). Thus, the T-RA and 9C-RA-induced activities of the reporter in transformants expressing both receptors were 6-fold and 12-fold higher, respectively, than in those expressing RARα alone. These results clearly demonstrate that RARα and RXRα cooperate to transactivate a DR5 element in yeast, even in the absence of ligand. Dose-responses to T-RA and 9C-RA in transformants expressing both RARα and RXRα confirmed that 9C-RA is the more potent inducer in this system (FIG. 11c).

Previous studies have shown that the formation of heterodimers in solution results in cooperative DNA binding by RARs and RXRs in vitro (Yu, V. C. et al., *Cell* 67:1251–1266 (1991); Leid, M. et al., *Cell* 68:377–395 (1992); Zhang, X. K. et al., *Nature* 355:441–446 (1992); Kliewer, S. A. et al., *Nature* 355:446–449 (1992)). Gel retardation experiments confirmed that only extracts from yeast expressing both receptors could efficiently retard the mobility of a synthetic DR5 probe (FIG. 12, lane 7).

Receptors were expressed in the yeast strain YPH250 as described above. Cell-free extracts were prepared from late log phase cultures of transformants grown in selective media as follows: cells were grown overnight in selective medium (20 ml), washed once and lysed in 0. 15 ml of high salt buffer (20 mM Tris-HCl pH 7.5, 0.4M KCl, 2 mM DTT, 20% glycerol, containing protease inhibitors) using the glass bead disruption method. After clearing at $10,000 \times G$ for 15 min, 20 μg (approx. 2.5 μl) of the supernatant was diluted with 7 μl of low salt buffer (same as above but containing 0.05M KCl), 1 μl poly(dI-dC). poly(dI-dC) at 10 mg/ml was added and the mixture was incubated for 15 min at 4° C. Gel retardations (using 50,000 cpm of labelled probe) and antibody supershifts were performed as previously described (Nicholson, R. C. et al., *EMBO J.* 9:4443–4454 (1990)).

The presence of both receptors in the retarded complex was verified by supershifting the complex with anti-RARα (FIG. 12, lane 8) or anti-RXRα (data not shown) monoclonal antibodies. Thus, RARs and RXRs produced in yeast form heterodimers in vitro, as has been observed for receptors produced in other systems.

While this result supports the idea that cooperative DNA binding is an important requirement in activation of a RARE-regulated reporter in vivo, it does not explain the differential responses to 9C-RA and T-RA observed in the transactivation experiments (FIG. 11c). Therefore, to investigate the individual contributions of RARα and RXRα to heterodimer-mediated transcription, we used a dominant negative receptor mutant (RXRαdn) (Durand, B. et al., *Cell* 71:73–85 (1992)), which has lost its ligand inducible activity, while retaining its ability to enhance the DNA-binding of RARα in vitro (FIG. 12, lanes 9 and 10). Transactivation experiments showed that coexpression of RARα and RXRαdn resulted in a loss of the differential response to T-RA and 9C-RA (FIG. 11c). This indicates that RXRα not only enhances the binding of RARα to a DR5, but also mediates, at least in part, the 9C-RA stimulation of the DR5 reporter. To investigate the origin of the ligand-independent activity of the heterodimer, we constructed transcriptionally compromised mutants of RARα (RARαdnΔAB) and RXRα (RXRαdnΔAB) which bear deletions of their entire A/B regions, in addition to C-terminal truncations. Note that deletion of the A/B region does not affect the ability of these receptors to bind DNA cooperatively in vitro (unpublished results from our laboratory). Coexpression of RARαdnΔAB and RXRα strongly reduced the constitutive activity and abolished the response to T-RA observed using full length receptors, while some induction occurred in the presence of 9C-RA (FIG. 11b). In contrast, no reduction in the constitutive activity was observed when RARα and RXRαdnΔAB were coexpressed, indicating that RARα is largely responsible for the ligand-independent activation. This is consistent with the presence of a strong constitutive activation function (AF-1) in RARα, but not RXRα, as shown above. Furthermore, as observed for RARα/RXRαdn (FIG. 11c), the differential response to T-RA and 9C-RA was lost when RARα and RXRαdnΔAB were coexpressed. In summary, our results show that RAR/RXR heterodimers possess a constitutive activity in vivo. However, target gene expression is further inducible by T-RA (through RARα) and 9C-RA (through RARα and RXRα).

In conclusion, this study provides compelling evidence that heterodimers of RARα and RXRα are required for efficient activation of a DR5-regulated reporter in vivo. Moreover, it demonstrates that heterodimers of RARs and RXRs bind to a RARE and stimulate gene transcription in the absence of ligand. This distinguishes RARs and RXRs from those nuclear receptors whose activities appear to be entirely dependent on ligand. The experimental advantages over mammalian systems, namely the absence of endogenous RARs, RXRs and RA isomerase activities, make yeast an excellent model to investigate the molecular mechanisms underlying retinoid signal transduction.

TABLE 2

| RECEPTOR | OMP decase activity units | | |
|---|---|---|---|
| | (-) | (T-RA) | (9C-RA) |
| None | 0.02 | 0.02 (1) | 0.02 (1) |
| RARα1-ER.CAS | 0.65 | 14.70 (23) | 12.90 (20) |
| RARα(DEF)-ER.CAS | 0.09 | 0.82 (9) | 0.94 (10) |
| RARα1(AB)-ER(C) | 3.12 | 3.03 (1) | 3.09 (1) |
| RXRα-ER(C) | 0.22 | 0.20 (1) | 1.05 (5) |
| RXRα(DE)-ER.CAS | 2.01 | 1.85 (1) | 9.92 (5) |
| RXRα(AB)-ER(C) | 0.02 | 0.02 (1) | 0.02 (1) |

Characterization of autonomous activation functions (AFs) in RARα and RXRα. The chimeric receptors illustrated in FIG. 10a were tested for their ability to activate the 3ERE-URA3 reporter gene in yeast strain PL3 in the presence or absence of T-RA and 9C-RA as indicated. Vector without insert was used as a control ("None"). Transactivation data are expressed as OMPdecase activities; the mean values shown in the table were determined from duplicate assays with three individual transformants for each clone. The numbers in parentheses indicate the fold induction over the activity observed for each receptor in the absence of ligand.

EXAMPLE 3

Retinoic acid (RA) signalling involves at least two classes of proteins, the retinoic acid receptors (RARα, RARβ, RARγ) and retinoid X receptors (RXRα, RXRβ, RXRγ) (Reviewed in Green and Chambon, Trends Genet. 4:309–314 (1988); Evans, R. M., Science 240:889–895 (1988); DeLuca, L. M., FASEB J. 5:2924–2933 (1991); Linney, E., In Current Topics in Developmental Biology, Vol. 27, Academic Press (1992); and Leid, M. et al., Trends Biochem. Sci. 17:427–433 (1992)). RARs and RXRs are members of the steroid/thyroid hormone receptor superfamily, and exhibit the modular protein structure typical to this group, including domains which function in DNA binding, dimerisation, ligand binding and transactivation. Ligand competition experiments and binding studies revealed that, while the three RAR types show strong affinities for both the all-trans and 9-cis isoforms of RA, the RXRs showed a marked specificity for the latter molecule (Heyman, R. A. et al., Cell 68:397–406 (1992); Levin, A. A. et al., Nature (London) 355:359–361 (1992); and Allenby, G. et al., Proc. Natl. Acad. Sci. USA 89:30–34 (1992)). Ligand binding appears to be required to induce transactivation functions (AFs) which overlap the N-terminal and ligand binding domains of these proteins (Nagpal, S. et al., Cell 70:1007–1019 (1992); Heery, D. M. et al., Proc. Natl. Acad. Sci. USA 90:4281–4285 (1993); and Nagpal, S. et al., EMBO J. 12:2349–2360 (1993)). It has recently been shown that the affinities of RARs for their target sequences is strongly increased when they are complexed as heterodimers with RXRs (Leid, M. et al., Cell 68:377–395 (1992); Yu, V. C. et al., Cell 67:1251–1266 (1991); Kliewer, S. A. et al., Nature (London) 355:446–449 (1992); Zhang, X. K. et al., Nature (London) 355:441–446 (1992); Marks, M. S. et al., EMBO J. 11: 1419–1435 (1992); Bugge, T. H. et al., EMBO J. 11:1409–1418 (1992); and Berrodin, T. J. et al., Mol. Endocrinol. 6:1468–1478 (1992)), and a series of heptad repeats present in the E domains of both receptors, are largely responsible for heterodimer formation in solution (Forman and Samuels, The New Biologist 2:587–594 (1990) for review). RXRs exhibit promiscuous heterodimerisation properties in vitro, forming complexes with other factors including the thyroid receptor (TR), Vitamin D receptor (VDR), peroxisome proliferator activated receptor (PPAR), the COUP-TF receptor, which stimulates their cooperative and selective binding to cognate hormone response elements in vitro (Leid, M. et al., Trends Biochem. Sci. 17:427–433 (1992), Green, S., Nature (London) 361:590–591 (1993) and references therein).

Naturally occurring RA response elements (RAREs) have been identified in the promoters of a number of genes, and generally consist of direct repetitions (DR) of one or more copies of a moderately conserved hexamer sequence, 5'-PuG (G/T)TCA-3'. The length of the spacer sequence between the hexameric motifs is variable, being 5 bp in RAREs found in the genes encoding RARα2 (Leroy, P. et al., Proc. Natl. Acad. Sci. USA 88:10138–10142 (1991)), RARβ2 (de Thé, H. et al., Nature (London) 343:177–180 (1990); and Sucov, H. M. et al., Proc. Natl. Acad. Sci. USA 87:5392–5396 (1990)), RARγ2 (Lehmann, J. M. et al., Mol. Cell. Biol. 12:2976–2985 (1992)) and alcohol dehydrogenase 3 (ADH3; Duester, G. et al., Mol. Cell. Biol. 11:1638–1648 (1991)), 4 bp in the Laminin B1 gene (Vasios, G. et al., EMBO J. 10:1149–1158 (1991)), 2 bp as in the cellular retinol binding protein (CRBPI; Smith, W. C. et al., EMBO J. 10:2223–2230 (1991)) and cellular retinoic acid binding protein (CRABPII; Durand, B. et al., Cell 71:73–85 (1992)) genes, or 1 bp as found in the genes encoding CRABPII (Durand, B. et al., Cell 71:73–85 (1992)), phosphoenolpyruvate carboxykinase (PEPCK; Hall, R. K. et al., Mol. Cell. Biol. 12:5527–5535 (1992)), apolipoprotein A1 (ApoA1; Rottman, J. N. et al., Mol. Cell. Biol. 11:3814–3820 (1991)) and medium chain acyl-CoA dehydrogenase (MCAD; Raisher, B. D. et al., J. Biol. Chem. 267:20264–20269 (1992)). A systematic study by Mader et al., (J. Biol. Chem. 268:591–600 (1993)) showed that the sequences of the half sites, the length and sequence of the spacer between them and the flanking sequences, all influence the capacity of these elements to function as RAREs in transient transfection experiments. In addition, it has been proposed that a distinct signalling pathway governed by RXR homodimers mediated through RXR-specific response elements (RXREs) exists in vivo (Mangelsdorf, D. J. et al., Cell 66:555–561 (1991)). Evidence to support this hypothesis came from transient transfection studies in animal cells where transfection of plasmids expressing RXRs, but not RARs, resulted in RA-dependent activation of reporter genes driven by putative RXREs from the rat CRBPII (Mangelsdorf, D. J. et al., Cell 66:555–561 (1991)), human ApoA1 (Rottman, J. N. et al., Mol. Cell. Biol. 11:3814–3820 (1991)) and mouse CRB-PII (Nakshatri and Chambon, J. Biol. Chem. 269:890–902 (1994)) promoters, and a synthetic RXRE (Mader, S. et al., J. Biol. Chem. 268:591–600 (1993)). These elements share a common arrangement of one or more half sites repeated at single base pair intervals (i.e. DR1-type elements). Additionally, homodimers of RXRs show a preference for binding to DR1-type elements in vitro (Mader, S. et al., *J. Biol. Chem.* 268:591–600 (1993), Nakshatri and Chambon, *J. Biol. Chem.* 269:890–902 (1994)) and Kliewer, S. A. et al., *Proc. Natl. Acad. Sci. USA* 89:1448–1452 (1992)). However, transient transfection studies (even in insect cell-lines) are prone to interference from endogenous factors which may contribute to the apparent RXR-specific activity. For this reason, we have chosen the yeast system to address the questions on the apparent polymorphic nature of RAREs and the possible independent function of RXR in vivo.

Materials and Methods

Yeast strains and expression plasmids

*S. cerevisiae* strain YPH250 (MATa ura3-52 lys2-801 ade2-101 trp1-D1 his3-D200 leu2-D1) (Sikorski and Hieter, *Genetics* 122:19–27 (1989)) was used for all yeast experiments and was a gift from P. Hieter. The human RARα1 (aa 1–462), mouse RXRα (aa 1–467), and mouse dnRXRα (aa 1–448) cDNAs (Heery, D. M. et al., *Proc. Natl. Acad. Sci. USA* 90:4281–4285 (1993)) and the cDNA encoding the mouse RXRαΔAB (aa 140–467) (Nagpal, S. et al., *EMBO J.* 12:2349–2360 (1993)) were cloned into the unique EcoR1 site of the yeast PGK expression cassette present in the yeast expression vectors YEp90, YCp90, YEp10 or YCp10 as required. The construction of the $2\mu$ containing expression vector YEp90, which contains the yeast HIS3 gene as a selectable marker, has been described previously (Pierrat, B. et al., *Gene* 119:237–245 (1992)). The plasmid YEp10 (a gift from D. Metzger) is identical to YEp90 except that the HIS3 marker is replaced by a BglII fragment containing the yeast TRP1 gene. YCp90 and YCp10 are ARS CEN containing vectors which carry HIS3 or TRP1 markers respectively, and which were derived from the plasmids pRS313 and pRS314 (Sikorski and Hieter, *Genetics* 122:19–27 (1989)) as follows. First the unique EcoRI sites in the polylinker sequences of the plasmids pRS313 and pRS314 were destroyed by EcoRI digestion, treatment with Klenow fragment and religation. The yeast PGK expression cassette from the plasmid pTG848 (Loison, G. et al., *Yeast* 5:497–507 (1989)) was then cloned as a ClaI fragment into the unique ClaI site in the polylinkers of both plasmids.

Reporter Plasmids

The URA3 reporter system and the construction of the pRS315-DR5-URA3 reporter plasmid have been described previously (Heery, D. M. et al., *Proc. Natl. Acad. Sci. USA* 90:4281–4285 (1993), Pierrat, B. et al., *Gene* 119:237–245 (1992)). To construct a URA3 reporter series driven by different response elements (DR1-DR4 and IR0), we synthesised a set of adaptors containing single response element sequences as shown in FIG. 13, panel A. All elements were flanked by identical sequences on their 5' (5'-GATCC-3') and 3' (5'-G-3') sides which were designed to generate ends compatible with NheI and BglII. One copy of each adaptor was inserted into the unique NheI and BglII restriction sites present in an engineered URA3 promoter, carried in pBluescript as a HinDIII-PstI fragment (Heery, D. M. et al., *Proc. Natl. Acad. Sci. USA* 90:4281–4285 (1993)). The DRn-URA3 and IR0-URA3 promoters were then excised as HinDIII-PstI fragments and used to replace the corresponding fragment in the pRS315-DR5-URA3 reporter plasmid, to create the new series of URA3 reporter genes. The CRBPII-URA3 reporter was constructed in an identical fashion using an adaptor containing the RXRE sequence from the rat CRBPII gene promoter (Mangelsdorf, D. J. et al., *Cell* 66:555–561 (1991)).

Results

Direct Repeats of the Motif 5'-AGGTCA-3' with Different Spacings and an Inverted Repeat of the Same Motif Function as RAREs in Yeast In a previous study, we demonstrated that efficient RA induction of a reporter gene driven by a RARE sequence (DR5-URA3) in yeast required heterodimers of RARs and RXRs (Heery, D. M. et al., *Proc. Natl. Acad. Sci. USA* 90:4281–4285 (1993)), as observed in animal cells (Durand, B. et al., *Cell* 71:73–85 (1992)). As considerable polymorphism exists in the interval lengths found in sequences which function as RAREs in animal cells (Green, S., *Nature (London)* 361:590–591 (1993); Leroy, P. et al., *Proc. Natl. Acad. Sci. USA* 88:10138–10142 (1991); de Thé, H. et al., *Nature (London)* 343:177–180 (1990); Sucov, H. M. et al., *Proc. Natl. Acad. Sci. USA* 87:5392–5396 (1990); Lehmann, J. M. et al., *Mol. Cell. Biol.* 12:2976–2985 (1992); Duester, G. et al., *Mol. Cell. Biol.* 11:1638–1648 (1991); Vasios, G. et al., *EMBO J.* 10:1149–1158 (1991); Smith, W. C. et al., *EMBO J.* 10:2223–2230 (1991); Durand, B. et al., *Cell* 71:73–85 (1992); Hall, R. K. et al., *Mol. Cell. Biol.* 12:5527–5535 (1992); Rottman, J. N. et al., *Mol. Cell. Biol.* 11:3814–3820 (1991) and Raisher, B. D. et. al., *J. Biol. Chem.* 267:20264–20269 (1992)), a logical extension of this work was to test the effect of varying the distance between the half site motifs in the response element on responsiveness to RARs and RXRs, in yeast. The RARE used previously (Heery, D. M. et al., *Proc. Natl. Acad. Sci. USA* 90:4281–4285 (1993)) consisted of a direct repetition of the motif 5'-AGGTCA-3' separated by a 5 bp sequence identical to that found in the RARE from the RARα2 promoter (Leroy, P. et al., *Proc. Natl. Acad. Sci. USA* 88:10138–10142 (1991), Brand, N. J. et al., *Nuc. Acids Res.* 18:6799–6806 (1990)). Reporters consisting of the yeast URA3 gene preceded by direct repeats of the same motif separated by spacers of 1 to 4 base pairs (DR1-URA3 through DR4-URA3), and also a reporter containing an inverted repeat of the same motif with no spacing (IR0-URA3), were constructed (See Example 2). The sequences of these response elements and the DR5 element are indicated in FIG. 13, panel A. The reporters were cloned into a centromeric plasmid, as previously described (Heery, D. M. et al., *Proc. Natl. Acad. Sci. USA* 90:4281–4285 (1993)), and introduced into a yeast strain expressing RARα, RXRα or both receptors from multicopy ($2\mu$) plasmid vectors (See Example 2). Reporter (orotidine-5'-monophosphate decarboxylase; OMPdecase) activity in cell-free extracts of cultures grown to exponential phase in the presence or absence of 500 nM all-trans RA or 9-cis RA, was determined as previously described (Wolcott and Ross, *Biochem. Biophys. Acta* 122:532–534 (1966)). As shown in FIG. 13, panel B, little or no reporter activities were observed in the absence of RA receptors (control), indicating that endogenous yeast factors were incapable of significant activation of these reporters. In the absence of ligand, coexpression of RARα and RXRα led to a 3-fold constitutive increase in the activities of the DR2, DR3 and DR4 reporters, and 10-fold and 16-fold increases in the activities of the DR1 and DR5 reporters, respectively. Addition of all-trans RA (500 nM) to the growth medium further induced the activities of all reporters (5- to 6-fold above the control for DR2, DR3 and DR4, 18-fold for DR1 and 27-fold for DR5). Addition of 9-cis RA (500 nM) to the growth medium induced the DR2, DR3 and DR4 reporters approximately 10-fold, the DR1 reporter 36-fold and the DR5 reporter 60-fold above their respective control activities. Thus, direct repetitions of the motif 5'-AGGTCA-3' with spacings of 1 to 5 base pairs render a reporter gene inducible by RA in yeast, albeit with different efficacies, which is consistent with similar observations in animal cells (Leid, M. et al., *Trends Biochem. Sci.* 17:427–433 (1992); Leroy, P. et al., *Proc. Natl. Acad. Sci. USA* 88:10138–10142 (1991); de Thé, H. et al., *Nature (London)* 343:177–180 (1990); Sucov, H. M. et al., *Proc. Natl. Acad. Sci. USA* 87:5392–5396 (1990); Lehmann, J. M. et al., *Mol. Cell. Biol.* 12:2976–2985 (1992); Duester, G. et al., *Mol. Cell. Biol.* 11:1638–1648 (1991); Vasios, G. et al., *EMBO J.* 10:1149–1158 (1991); Smith, W. C. et al., *EMBO J.* 10:2223–2230 (1991); Durand, B. et al., *Cell* 71:73–85 (1992); Hall, R. K. et al., *Mol. Cell. Biol.* 12:5527–5535 (1992); Rottman, J. N. et al., *Mol. Cell. Biol.* 11:3814–3820 (1991); Raisher, B. D. et al., *J. Biol. Chem.* 267:20264–20269 (1992); and Mader, S. et al., *J. Biol. Chem.* 268:591–600 (1993)). Coexpression of RARα and RXRα was also found to increase the activity of a reporter containing an inverted repeat of 5'-AGGTCA-3'. The basal activity in the absence of receptors (control) of the IR0-URA3 reporter was increased 15-fold by the heterodimer in the absence of ligand, and induced 20-fold and 40-fold above the control activity in the presence of all-trans RA and 9-cis RA, respectively (FIG. 13, panel B). However, note that despite the apparently high activity in terms of fold stimulation, the actual levels of activity for this reporter are quite low when compared to the DR5 reporter. Other groups have reported RAR/RXR activity on a similar response element (TREpal) in animal cells (Mangelsdorf, D. J. et al., *Cell* 66:555–561 (1991), Umesono, K. et al., *Nature* 345:262–265 (1988)) and in yeast (Hall, B. L. et al., *Proc. Natl. Acad. Sci. USA* 90:6929–6933 (1993)).

To determine how the observed transactivation data correlated with the ability of the receptors to bind to the corresponding sequences, we performed in vitro DNA binding assays. Extracts from yeast cells expressing both receptors efficiently retarded the mobility of the DRI and DR5 probes, and bound more weakly to the DR2, DR3, DR4 probes under identical conditions (FIG. 13, panel C, lanes 1–5). A weak band shift was also observed for the IR0 element (lane 6) after prolonged autoradiography. The presence of RARα and RXRα in these complexes was verified by supershift assays using specific monoclonal antibodies against the receptors (not shown). Thus, the efficiency of reporter activation correlates closely with the capacity of the heterodimer to bind to the corresponding element in vitro. Note that the relatively low affinity of RAR/RXR heterodimers for the DR2 and DR4 probes in vitro, and the weak activation of the corresponding reporter genes in yeast, is a consequence of the spacer and flanking sequences of the elements used in this study. For example, a DR2 probe with different spacer and flanking sequences was bound 6-fold more efficiently by RARs and RXRs produced in yeast, or *E. coli* (not shown). This is consistent with the observations that changes in the spacer, half site motif or the flanking sequences can significantly affect binding and activation by RARs and RXRs produced in mammalian cells (Leroy, P. et al., *Proc. Natl. Acad. Sci. USA* 88:10138–10142 (1991), Mader, S. et al., *J. Biol. Chem.* 268:591–600 (1993)) and in yeast (our unpublished results).

The ability of the isolated receptors to activate the reporter series was also tested. As previously reported (Heery, D. M. et al., *Proc. Natl. Acad. Sci. USA* 90:4281–4285 (1993)) expression of RARα alone in yeast resulted in a 5- to 7-fold activation of DR5 reporter in the presence of either all-trans RA or 9-cis RA (FIG. 13, panel B). However, RARα alone showed little if any ability to stimulate the activity of the DR1, DR2, DR3, DR4 and IR0 reporters, in the presence or absence of ligand. Similarly RXRα had little effect on the DR2, DR3, DR4 and DR5 reporter activities (2–3 fold 9-cis RA-dependent stimulation), but stimulated the activity of the DR1 reporter at least 30-fold in response to 9-cis RA, but not all-trans RA (FIG. 13, panel B). Western blot experiments using specific monoclonal antibodies (gifts from C. Egly and M. P. Gaub) detected similar levels of RARα or RXRα in extracts from cells expressing either one or both receptors (data not shown), thus eliminating the possibility that the observed increases in DNA binding and transactivation by heterodimers were due to altered levels of receptor proteins. RXRα also activated the IR0 reporter 20-fold above background in a ligand dependent manner (FIG. 13, panel B), although as stated above, the absolute value of this activity was low (6-fold lower than the DR1 reporter). Cell-free extracts from transformants expressing no receptor, or either of the receptors alone, failed to retard the DR5 probe (Heery, D. M. et al., *Proc. Natl. Acad. Sci. USA* 90:4281–4285 (1993)) or any of the other DR probes in gel shift experiments under conditions identical to those used in the experiment shown in FIG. 13, panel C (data not shown). However, after prolonged autoradiography, a weak band shift was detected for RXRα homodimers which was specific for the DR1 probe. These results are consistent with the lack of significant constitutive activation of the reporter gene series by homodimers. In our hands, the inclusion of all-trans RA or 9-cis RA (500 nM) in the growth medium, extraction buffer and assay buffer did not further stimulate the binding of either homodimers or heterodimers to any of the probes (data not shown), although we did not determine if the conditions used in the gel shift experiments were optimal for the binding of ligand to the receptors.

9-cis Retinoic Acid Induced Activity of RXRα on Putative RXRE Sequences in Yeast Ligand dose response curves (FIG. 14, panel A) revealed that the concentration of 9-cis RA required for half maximal activity of RXRα on the DR1 reporter in yeast was approximately 100 nM. In contrast, no induction was observed in the presence of all-trans RA, even at a concentration of 1 µM. This is in agreement with our previous data for the chimeric receptors RXRα-ER(C) and RXRα(DEF)-ER.Cas, whose activities were induced exclusively by 9-cis stereoisomers of RA in yeast (Heery, D. M. et al., *Proc. Natl. Acad. Sci. USA* 90:4281–4285 (1993)). The dose response curves in the presence of both RARα and RXRα confirmed the modest stimulation of the DR1 reporter activity by the heterodimer in the presence of all-trans RA (FIG. 14, panel A). In addition, experiments using a transcriptionally inactive dominant negative RXRa (dnRXRaDAB; Heery, D. M. et al., *Proc. Natl. Acad. Sci. USA* 90:4281–4285 (1993), Durand, B. et al., *Cell* 71:73–85 (1992)) confirmed that RARα is responsible for this stimulation by all-trans RA (D.M.H. and B.P., unpublished results). Thus, the DR1 element appears to bind both RAR/RXR heterodimers and RXR alone (presumably as homodimers). This result is in contrast to a recent report by Hall et al., (Hall, B. L. et al., *Proc. Natl. Acad. Sci. USA* 90:6929–6933 (1993)) who were unable to demonstrate significant activity of RXR on a DR1 element. Note that these authors used another receptor isoform (RXRγ), a different reporter (based on the yeast CYC1 promoter), and a different spacer nucleotide in the DR1 sequence as compared to this study. To confirm that the RXRγ activity we observed on DR1 was not simply due to high level expression of the receptor in yeast, we expressed RXRγ from a centromeric expression vector. Significant 9-cis RA induced activation was maintained on the DR1 and IR0 reporters (10- to 15-fold), despite a strong decrease (30- to 50-fold) in the level of receptor detectable in western blot analyses (data not shown).

The rat CRBPII gene promoter contains a sequence consisting of four almost perfect repeats of the hexamer motif 5'-AGGTCA -3' with 1bp spacers, which has been reported to act as a RXRE in animal cells (Mangelsdorf, D. J. et al., *Cell* 66:555–561 (1991); Nakshatri and Chambon, *J. Biol. Chem.* 269:890–902 (1994)). We determined if this element would also function as a target for transactivation by RXRα in yeast. As shown in FIG. 14, panel B, the rat CRBPII RXRE reporter was very efficiently activated (116-fold over the control) by RXRα in the presence of 9-cis RA in yeast, i.e. almost 20-fold higher than that of the DR1 reporter in the same system. This result indicates a synergistic activation by RXRα molecules bound to the multiple binding sites in this promoter. As observed with the DR1 reporter, the activity of the rat CRBPII RXRE reporter was also significantly induced (12-fold) in the presence of 9-cis RA, when RXRα was expressed from a centromeric vector (data not shown). These results indicate a synergistic activation by RXRα molecules bound to the multiple binding sites in this promoter. Coexpression of RARα and RXRα in yeast increased the activity of the rat CRBPII RXRE reporter 14-fold above the control in the absence of ligand, and 21-fold and 70-fold above the control in the presence of all-trans RA and 9-cis RA, respectively (data not shown). Accordingly, gel shift experiments showed that RARα strongly increased the binding of RXRα to the rat CRBPII RXRE element in vitro (not shown), and thus coexpression of both receptors in yeast did not have the same dramatic negative effect on activation of the rat CRBPII RXRE reporter as previously observed in some (Mangelsdorf, D. J. et al., *Cell* 66:555–561 (1991)), but not all (Nakshatri and Chambon *J. Biol. Chem.* 269:890–902 (1998)), animal cells.

Our previous study (Heery, D. M. et al., *Proc. Natl. Acad. Sci. USA* 90:4281–4285 (1993)) established that a 9-cis RA-inducible activation function (AF-2) present in the ligand binding domain is largely responsible for the activity of RXRα in yeast, as we failed to detect a strong activation function in the N-terminal (AB) region of RXRα by linking it to a heterologous DBD. Accordingly, deletion of the A/B region of RXRα (RXRαΔAB) did not adversely affect the levels of activation achieved on either the DR1 or rat CRBPII RXRE reporters, in the presence or absence of ligand (FIG. 14, panel B). In contrast, a truncated receptor in which the 19 most carboxy-terminal amino acids were deleted (dnRXRα), which behaves as a dominant negative receptor in mammalian cells (Durand, B. et al., *Cell* 71:73–85 (1992)), failed to mediate a response of either the DR1 or the rat CRBPII RXRE reporters to 9-cis RA in yeast (FIG. 14, panel B), despite being expressed to a similar level as the full length receptor (not shown). This result indicates that the carboxyl terminal region is required for ligand-induced transcription by RXRα. It is also of note that unliganded RXRα stimulated the rat CRBPII RXRE reporter activity 8- to 10-fold over the activity of the control (FIG. 14, panel B). This constitutive activity was observed even when the A/B domain was deleted, and thus may indicate a weak constitutive activity of AF-2.

Discussion

We have demonstrated that RXRα activates transcription efficiently in a biological system devoid of other members of the nuclear receptor superfamily. This activity of RXRα was found to be specific for elements having a DR1-type structure, so-called "RXREs", and to a lesser extent, an inverted repeat similar to TRE-pal. DR1-type elements have been found in the promoters of genes including the rat CRBPII (Mangelsdorf, D. J. et al., *Cell* 66:555–561 (1991)), human ApoA1 (Rottman, J. N. et al., *Mol. Cell. Biol.* 11:3814–3820 (1991)) and mouse CRABPII (Durand, B. et al., *Cell* 71:73–85 (1992)) genes, which are involved in vitamin A metabolism, and it has been suggested that this may signify the existence of a 9-cis RA autoregulatory network which operates through RXR (Lucas and Granner, *Annu. Rev. Biochem.* 61:1131–1173 (1992)). However, DR1 elements are also recognized by other members of the steroid receptor superfamily, including PPAR, COUP-TF, Arp-1, HNF4, and ear2 (Green, S., *Nature (London)* 361:590–591 (1993), and references therein). Thus it was important to test the ability of RXR to activate transcription from a DR1 element in a system which has no known homologues of nuclear receptors. Transactivation was very potent on the rat CRBPII RXRE reporter, which contains multiple DR1 repeats, suggesting synergistic activation by RXRα molecules bound to the multiple target sites. Our findings that RXRα strongly activates reporter genes driven by DR1 elements in yeast are consistent with the hypothesis that, in addition to their role as heterodimeric partners of RAR, VDR, PPAR and TR, RXRs may also function independently as ligand-dependent transcription factors, in the more classical fashion of steroid receptors, i.e. as homodimers. Similarly, homodimers of RARα were found to activate transcription in yeast (albeit less efficiently than heterodimers) in a ligand-dependent manner, but only on a DR5 reporter. As with steroid receptors such as the ER, transactivation by homodimers of RARs and RXRs appears to be largely ligand-dependent, and in the case of RXRα is due to the presence of an activation function (AF-2) in the ligand-binding domain which is specifically induced by 9-cis stereoisomers of RA. In addition AF-2 may also be responsible for the weak constitutive activity of RXRα observed on the rat CRBPII RXRE and DR1 reporters. While the A/B region of RXR appears to be dispensable for the transcriptional activity of this receptor in these experiments, more recent results suggest that it contains an AF, functional in yeast (not shown).

RA-dependent transactivation in animal cells appears to be mediated through DRs consisting of half-site motifs spaced by 1 to 5 base pairs. Our results in yeast corroborate this observation, showing a strong correlation between the affinity of the heterodimer complex for a sequence and the strength of activation of the corresponding reporter gene in yeast. Although in this report we have only considered the effect of spacer length on DNA binding and activation, additional experiments have confirmed that the sequences of the half sites, spacers and flanking DNA all clearly influence the strength of binding and activation by heterodimers in yeast (our unpublished results), in agreement with the findings of Mader et al., (*J. Biol. Chem.* 268:591–600 (1993)).

What is claimed is:

1. A method of identifying an agent capable of transactivating a sequence operably linked to a DNA response element comprising the steps of:
   (a) incubating with the agent, a host cell, organism, or cell-free extract thereof containing a reporter sequence operably linked to the DNA response element; and
   (b) assaying for expression of the reporter sequence, wherein the host cell, organism, or cell-free extract has been altered to express one or more dimers comprising two subunits, wherein one of the subunits is a retinoic acid receptor (RAR) or a thyroid receptor (TR) and the other subunit is a retinoid X receptor (RXR).

2. The method of claim 1, wherein the RAR is selected from the group consisting of human RAR-α, human RAR-β, human RAR-γ, mouse RAR-α, mouse RAR-β, and mouse RAR-γ.

3. The method of claim 1, wherein the RXR is mouse RXR-β (Sequence ID No. 2 or amino acid sequence encoded by mouse RXR-β vector in ATCC accession no. PTA-4958).

4. The method of claim 3, wherein the amino acid sequence of the RXR is encoded by a nucleotide sequence of Sequence ID No. 1 or mouse RXR-β in ATCC accession no. PTA-4958.

5. The method of claim 1, wherein the TR is selected from the group consisting of human TR-α, human TR-β, mouse TR-α and mouse TR-β.

6. The method of claim 1, wherein the agent is retinoic acid, or a functionally equivalent derivative thereof.

7. The method of claim 7, wherein the DNA response element is synthetic or natural, having a repetitive core motif, which is purine-$G_T{}^G$TCA or a related sequence, in either orientation.

8. The method of claim 1, wherein one of the subunits is the RAR and the other subunit is the RXR.

9. The method of claim 1, wherein one of the subunits is the TR and the other subunit is the RXR.

10. A method of identifying an agent capable of transactivating a sequence operably linked to a DNA response element comprising the steps of:
    (a) incubating with the agent, a host cell, organism, or cell-free extract thereof containing a reporter sequence operably linked to the DNA response element; and
    (b) assaying for expression of the reporter sequence, wherein the host cell, organism, or cell-free extract has been altered to express one or more dimers comprising two subunits, wherein one of the subunits is a first RXR and the other subunit is a second RXR.

11. The method of claim 10, wherein the response element is transcriptionally activated by the agent, when the agent binds to an RXR/RXR dimer.

12. The method of claim 10, wherein the first or second RXR is selected from the group consisting of mouse RXR-β (Sequence ID No. 2 or amino acid sequence encoded by mouse RXR-β vector in ATCC accession no. PTA-4958), mouse RXR-α (Sequence ID No. 6 or amino acid sequence encoded by mouse RXR-α vector in ATCC accession no. PTA-4958), and mouse RXR-γ (Sequence ID No. 8 or amino acid sequence encoded by mouse RXR-γ vector in ATCC accession no. PTA-4958).

13. The method of claim 12, wherein the amino acid sequence of the first or second RXR is encoded by a nucleotide sequence selected from the group consisting of Sequence ID No. 1 or mouse RXR-β in ATCC accession no. PTA-4958, Sequence ID No. 5 or mouse RXR-α in ATCC accession no. PTA-4958, and Sequence ID No. 7 or mouse RXR-γ in ATCC accession no. PTA-4958.

14. The method of claim 10, wherein the first or second RXR has the amino acid sequence of human RXR-β as shown in Sequence ID No:4.

15. The method of claim 14, wherein the amino acid sequence of human RXR-β is encoded by the nucleotide sequence as shown in Sequence ID No:3.

16. The method of claim 10, wherein the agent is retinoic acid, or a functionally equivalent derivative thereof.

17. The method of claim 16, wherein the RXR has a specific activity of from about 1461 to 7,750,000 cpm/μg.

18. The method of claim 10, wherein the RXR has a specific activity of from about 315,789 to 7,750,000 cpm/μg.

19. The method of claim 10, wherein the DNA response element is synthetic or natural, having a repetitive core motif, which is purine-$G_T{}^G$TCA or a related sequence, in either orientation.

20. A method of identifying an agent capable of transactivating a sequence operably linked to a DNA response element comprising the steps of:
    (a) incubating with the agent, a host cell, organism, or cell-free extract thereof containing a reporter sequence operably linked to the DNA response element; and
    (b) assaying for expression of the reporter sequence, wherein the host cell, organism, or cell-free extract has been altered to express one or more dimers comprising two subunits, wherein one of the subunits is a retinoic acid receptor (RAR) or a thyroid receptor (TR) and the other subunit is a retinoid X receptor (RXR), wherein the RXR has the amino acid sequence of mouse RXR-γ as shown in Sequence ID No: 8.

21. The method of claim 20, wherein the amino acid sequence of mouse RXR-γ is encoded by a nucleotide sequence as shown in Sequence ID No: 7 or a nucleotide sequence of mouse RXR-γ in ATCC accession no. PTA-4958.

22. The method of claim 20, wherein the RAR is selected from the group consisting of human RAR-α, human RAR-β, human RAR-γ, mouse RAR-α, mouse RAR-β, and mouse RAR-γ.

23. The method of claim 20, wherein the TR is selected from the group consisting of human TR-α, human TR-β, mouse TR-α and mouse TR-β.

24. The method of claim 20, wherein the agent is retinoic acid, or a functionally equivalent derivative thereof.

25. The method of claim 20, wherein the RXR has a specific activity of from about 1461 to 7,750,000 cpm/μg.

26. The method of claims 20, wherein the RXR has a specific activity of from about 315,789 to 7,750,000 cpm/μg.

27. The method of claim 20, wherein the DNA response element is synthetic or natural, having a repetitive core motif, which is purine-$G_T{}^G$TCA or a related sequence, in either orientation.

28. A method of identifying an agent capable of transactivating a sequence operably linked to a DNA response element comprising the steps of:
    (a) incubating with the agent, a host cell, organism, or cell-free extract thereof containing a reporter sequence operably linked to the DNA response element; and
    (b) assaying for expression of the reporter sequence, wherein the host cell, organism, or cell-free extract has been altered to express one or more dimers comprising two subunits, wherein one of the subunits is a retinoic acid receptor (RAR) or a thyroid receptor (TR) and the other subunit is a retinoid X receptor (RXR), wherein the RXR has the amino acid sequence of mouse RXR-α as shown in Sequence ID No: 6.

29. The method of claim 28, wherein the amino acid sequence of mouse RXR-α is encoded by a nucleotide sequence as shown in Sequence ID No: 5 or a nucleotide sequence of mouse RXR-α in ATCC accession no. PTA-4958.

30. The method of claims 28, wherein the RAR is selected from the group consisting of human RAR-α, human RAR-β, human RAR-γ, mouse RAR-α, mouse RAR-β, and mouse RAR-γ.

31. The method of claim 28, wherein the TR is selected from the group consisting of human TR-α, human TR-β, mouse TR-α and mouse TR-β.

32. The method of claim 28, wherein the agent is retinoic acid, or a functionally equivalent derivative thereof.

33. The method of claim 28, wherein the RXR has a specific activity of from about 1461 to 7,750,000 cpm/μg.

34. The method of claim 28, wherein the DNA response element is synthetic or natural, having a repetitive core motif, which is purine-$G_T{}^G$TCA or a related sequence, in either orientation.

35. A method of identifying an agent capable of transactivating a sequence operably linked to a DNA response element comprising the steps of:

(a) incubating with the agent, a host cell, organism, or cell-free extract thereof containing a reporter sequence operably linked to the DNA response element; and (b) assaying for expression of the reporter sequence, wherein the host cell, organism, or cell-free extract has been altered to express one or more dimers comprising two subunits, wherein one of the subunits is a retinoic acid receptor (RAR) or a thyroid receptor (TR) and the other subunit is a retinoid X receptor (RXR), wherein the RXR has the amino acid sequence of human RXR-β as shown in Sequence ID No:4.

36. The method of claim 35, wherein the amino acid sequence of human RXR-β is encoded by the nucleotide sequence as shown in Sequence ID No:3.

37. The method of claim 35, wherein the RAR is selected from the group consisting of human RAR-60 , human RAR-β, human RAR-γ, mouse RAR-α, mouse RAR-β, and mouse RAR-β.

38. The method of claim 35, wherein the TR is selected from the group consisting of human TR-α, human TR-β, mouse TR-α, and mouse TR-β.

39. The method of claim 35, wherein the agent is retinoic acid, or a functionally equivalent derivative thereof.

40. The method of claim 35, wherein the RXR has a specific activity of from about 1461 to 7,750,000 cpm/μg.

41. The method of claim 35, wherein the RXR has a specific activity of from about 315,789 to 7,750,000 cpm/μg.

42. The method of claim 35, wherein the DNA response element is synthetic or natural, having a repetitive core motif, which is purine-$G_T{}^G$TCA or a related sequence, in either orientation.

* * * * *

Adverse Decision in Interference

Patent No. 6,635,429, Mark Leid, Philippe Kastner, Pierre Chambon, NOVEL HETERODIMERIC NUCLEAR RECEPTORS PROTEINS, GENES ENCODING SAME, AND USAGE THEREOF, Interference No. 105,510, final judgment adverse to the patentees rendered November 30, 2006, as to claims 10-13, 16, and 19.

(*Official Gazette* June 12, 2007)